(12) United States Patent
Chern et al.

(10) Patent No.: US 9,644,214 B2
(45) Date of Patent: May 9, 2017

(54) ENHANCED DISEASE RESISTANCE BY INTRODUCTION OF NH3

(75) Inventors: Mawsheng Chern, Davis, CA (US); Wei Bai, Hohhot (CN); Pamela Ronald, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 527 days.

(21) Appl. No.: 13/640,040

(22) PCT Filed: May 25, 2011

(86) PCT No.: PCT/US2011/037985
§ 371 (c)(1),
(2), (4) Date: Feb. 27, 2013

(87) PCT Pub. No.: WO2011/150117
PCT Pub. Date: Dec. 1, 2011

(65) Prior Publication Data
US 2013/0152227 A1    Jun. 13, 2013

Related U.S. Application Data

(60) Provisional application No. 61/348,618, filed on May 26, 2010.

(51) Int. Cl.
*C12N 15/82* (2006.01)
*C07K 14/415* (2006.01)

(52) U.S. Cl.
CPC ........ *C12N 15/8279* (2013.01); *C07K 14/415* (2013.01); *C12N 15/8263* (2013.01); *C12N 15/8281* (2013.01)

(58) Field of Classification Search
None
See application file for complete search history.

(56) References Cited

U.S. PATENT DOCUMENTS

| 2003/0172411 A1 | 9/2003 | Butler et al. | |
| 2006/0123505 A1* | 6/2006 | Kikuchi et al. | 800/278 |
| 2007/0016976 A1* | 1/2007 | Katagiri et al. | 800/279 |

OTHER PUBLICATIONS

Benfey et al, Science (1990) vol. 250 pp. 959-966.*
Guo et al (2004), Proc. Natl. Acad. Sci. USA vol. 101 pp. 9205-9210.*
Ngo et al. In the Protein Folding Problem and Tertiary Structure Prediction, 1994, Merz et al. (ed.), Birkhauser, Boston, MA, pp. 491-495.*
Kim et al, Plant Molecular Biology (1994) vol. 24 pp. 105-117.*
Donald et al, EMBO J. (1990) vol. 9 pp. 1717-1726.*
Potenza et al, In Vitro Cell. Dev. Biol.-Plant (2004) 40:1-22.*
Yuan et al, Plant Biotechnology Journal (2007) vol. 5, pp. 313-324.*
Buell et al (Jan. 4, 2004) BAC clone OSJNBa0056E06.*
Gurr et al, Trends in Biotechnology (2005) 23:283-290.*
Jorgensen et al, Cold Spring Harb Symp Quant Biol (2006) 71: 481-485.*

(Continued)

*Primary Examiner* — Amjad Abraham
*Assistant Examiner* — Fan Weihua
(74) *Attorney, Agent, or Firm* — Kilpatrick Townsend & Stockton LLP

(57) ABSTRACT

Methods and compositions for improving plant resistance by expression of NPR homolog 3 (NH3) polypeptides are provided.

11 Claims, 8 Drawing Sheets

(56) References Cited

OTHER PUBLICATIONS

Napoli et al, Plant Cell (1990) 2: 279-289.*
Cao et al., "The Arabidopsis npr1 gene that controls systemic acquired resistance encodes a novel protein containing ankyrin repeats," Cell, 1997, vol. 88, pp. 57-63.
Cao et al., "Generation of broad-spectrum disease resistance by overexpression of an essential regulatory gene in systemic acquired resistance," Proc. Natl. Acad. Sci., 1998, vol. 95, pp. 6531-6536.
Chern et al., "Evidence for a disease-resistance pathway in rice similar to the NPR1-mediated signaling pathway in Arabidopsis," Plant J, 2001, vol. 27, pp. 101-113.
Chern et al., "Over-expression of a rice NPR1 homolog leads to constitutive activation of defense response and hypersensitivity to light," Mol. Plant Microbe Interact., 2005, vol. 18, pp. 511-520.
Chern et al., "Rice NRR, a Negative Regulator of Disease Resistance, Interacts with Arabidopsis NPR1 and Rice NH1," Plant J, 2005, vol. 43, pp. 623-635.
Friedrich et al., "NIM1 overepression in Arabidopsis potentiates plant disease resistance and results in enhanced effectiveness of fungicides," Mol. Plant-Microbe Intercact, 2001, vol. 9, pp. 1114-1124.
Jacquemin et al., "A recent duplication revisited: phylogenetic analysis reveals an ancestral duplication highly-conserved throughout the *Oryza* genus and beyond," BMC Plant Biol., 2009, vol. 9, pp. 146.
Jun et al., "Blade-on-Petiolei coordinates organ determinacy and axial polarity in Arabidopsis by directly activating asymmetric leaves2," Plant Cell, 2010, vol. 22, pp. 62-76.
Le Henanff et al., "Characterization of Vitis vinifera NPR1 homologs involved in the regulation of pathogenesis-related gene expression," BMC Plant Biol., 2009, vol. 9(54), pp. 1-14.
Lin et al., "Transgenic tomato plants expressing the Arabidopsis NPR1 gene display enhanced resistance to a spectrum of fungal and bacterial diseases," Transgenic Res., 2004, vol. 13, pp. 567-581.
Liu et al., "An Arabidopsis NPR1-like gene, NPR4, is required for disease resistance," Plant J., 2005, vol. 41, pp. 304-318.
Park et al., "Rice XB15, a Protein Phosphatase 2C, Negatively Regulates Cell Death and XA21-Mediated Innate Immunity," PLoS Biology, 2008, vol. 6(9), pp. e231.
Yuan et al., "Functional analysis of rice NPR1-like genes reveals that OsNPR1/NH1 is the rice orthologue conferring disease resistance with enhanced herbivore susceptibility," Plant Biotechnol. J., 2007, vol. 5, pp. 313-324.
Zhang et al., "Negative regulation of defense response in Arabidopsis by two NPR1 paralogs," Plant J, 2006, vol. 48, pp. 647-656.
International Search Report and Written Opinion, Feb. 9, 2012, PCT app. No. PCT/US2011/037985.

* cited by examiner (a)

(b)

ENHANCED DISEASE RESISTANCE BY INTRODUCTION OF NH3

CROSS-REFERENCE TO RELATED APPLICATIONS

The present patent application claims benefit of priority to U.S. Provisional Patent Application No. 61/348,618, filed May 26, 2010, the contents of which are incorporated by reference herein for all purposes.

STATEMENT AS TO RIGHTS TO INVENTIONS MADE UNDER FEDERALLY SPONSORED RESEARCH AND DEVELOPMENT

This invention was made with Government support under Contract No. 2006-35604-16640 awarded by the United States Department of Agriculture. The Government has certain rights in this invention.

BACKGROUND OF THE INVENTION

Plants survive pathogen attack by employing various defense strategies, including strengthening of cell walls, the accumulation of phytoalexins, synthesis of salicylic acid (SA), and induction of pathogenesis-related (PR) genes. A hypersensitive response (HR) is often associated with the defense response and limits pathogen growth to the infected site. After an initial local infection, Systemic Acquired Resistance (SAR) often occurs which coordinately induces expression of a set of PR genes, leading to a long-lasting enhanced resistance against a broad spectrum of pathogens (Durrant and Dong, 2004). In dicots, like Arabidopsis and tobacco, SA and its synthetic analogs, such as 2,6-dichloroisonicotinic acid (INA), benzothiadiazole (BTH), and probenazole are potent inducers of SAR (Ward et al., 1991; Friedrich et al., 1996; Yoshioka et al., 2001). In monocots, SAR can be induced by BTH in wheat (Gorlach et al., 1996) and by Pseudomonas syringae in rice (Smith and Metraux, 1991). BTH can also induce disease resistance in rice (Schweizer et al., 1999; Rohilla et al., 2002; Shimono et al., 2007) and maize (Morris et al., 1998).

The NPR1 (also known as NIM1 and SAI1) gene is a key regulator of SA-mediated SAR in Arabidopsis (Cao et al., 1994; Delaney et al., 1995; Glazebrook et al., 1996; Ryals et al. 1997; Shah et al., 1997). Upon induction by SA, INA, or BTH, NPR1 expression levels are elevated (Cao et al., 1997). NPR1 affects the SAR pathway downstream of the SA signal. Arabidopsis npr1/nim1 mutants are impaired in their ability to induce PR gene expression and mount a SAR response even after treatment with SA or INA. NPR1 encodes a protein with a bipartite nuclear localization sequence and two protein-protein interaction domains: an ankyrin repeat domain and a BTB/POZ domain (Cao et al., 1997). Nuclear localization of NPR1 protein is essential for its function (Kinkema et al., 2000). The ankyrin domain is required for interaction with TGA transcription factors (Zhang et al., 1999; Despres et al., 2000) and the BTB/POZ domain interacts with the repression domain of TGA2 to negate its function (Boyle et al., 2009). During non-induced states, NPR1 protein forms an oligomer and is excluded from the nucleus. Upon SAR induction, monomeric NPR1 emerges through redox changes, accumulates in the nucleus, and activates PR gene expression (Mou et al. 2003). NPR1 also appears to modulate the cross-talk between SA- and JA-dependent pathways; the antagonistic effect of SA on JA signaling requires NPR1, but not nuclear localization of the NPR1 protein (Spoel et al., 2003).

Overexpression of NPR1 in Arabidopsis leads to enhanced disease resistance to both bacterial and oomycete pathogens in a dose-dependent manner (Cao et al., 1998). Similarly, overexpression of Arabidopsis NPR1 or the rice NPR1 ortholog, NH1, in rice results in enhanced resistance to rice bacterial blight pathogen Xanthomonas oryzae pv. oryzae (Xoo) and blast pathogen Magnaporthe grisea (Chern et al. 2001; Yuan et al., 2007), indicating the presence of a similar defense pathway in rice. Although transgenic Arabidopsis plants over-expressing NPR1 acquire enhanced sensitivity to SA and BTH (Freidrich et al., 2001), they display no obvious detrimental morphological changes and do not have elevated PR gene expression until activated by inducers or by infection of pathogens (Cao et al., 1998). However, in rice, overexpression of rice NH1 results in a development- and environment-dependent lesion-mimic phenotype, which can be further enhanced by application of BTH (Chern et al., 2005a). These results suggest that overexpression of NH1 in rice activates the defense response in the absence of inducer treatment or pathogen challenge, an undesirable consequence in terms of practical application. Thus, although rice possesses a pathway similar to the NPR1-mediated one in Arabidopsis, there may be significant differences in their regulation.

There are six NPR1-like genes in Arabidopsis (Liu et al., 2005; Zhang et al., 2006) and five NPR1-like genes in rice (Yuan et al., 2007). Despite extensive investigations done on NPR1, very little is known concerning the NPR1-like genes with regards to their possible involvement in plant defense. Arabidopsis NPR5 and NPR6 have recently been named BOP2 (Blade-On-Petiole2) and BOP1 (Blade-On-Petiole1), respectively. BOP1 and BOP2 regulate Arabidopsis leaf formation. Like NPR1, these proteins function as transcriptional coactivators targeting the AS2 (Asymmetric Leaves2) gene (Jun et al., 2010). Thus, NPR5 (BOP2) and NPR6 (BOP1) are mainly involved in regulating plant development rather than defense. Contradictory results concerning the function of Arabidopsis NPR4 have been reported. Liu et al. (2005) reported that Arabidopsis NPR4 is required for basal resistance to Pseudomonas syringae pv. tomato (Pst) DC3000 and Erysiphe cichoracearum because the npr4-1 mutant is more susceptible to these two pathogens. This group suggested that NPR4 may be also involved in the cross-talk between SA- and JA-dependent signaling pathways since expression of the JA-dependent marker gene PDF1.2 is compromised in npr4-1 leaves following application of methyl-JA. However, Zhang et al. (2006) reported that Arabidopsis NPR3 and NPR4 are negative regulators of PR gene expression and disease resistance. They showed that npr3 mutants have slightly increased basal PR-1 expression and the npr3npr4 double mutant shows even higher PR-1, PR-2, and PR-5 expression. The double mutant plants display enhanced resistance against virulent bacterial (including Pst DC3000) and oomycete pathogens (Zhang et al., 2006). Thus, the roles of NPR4 in disease resistance from these two reports contradict each other. In rice, Yuan et al. (2007) have overexpressed OsNPR1/NH1, OsNPR2, and OsNPR3 in rice and tested for enhanced resistance to Xoo and rice blast. These authors found that only OsNPR1 (but not OsNPR2 or OsNPR3) overexpression conferred enhanced resistance, leaving in doubt whether any rice NPR1 paralogs are involved in defense against pathogens.

BRIEF SUMMARY OF THE INVENTION

The present invention provides for plants (or a plant cell, seed, flower, leaf, fruit, or other plant part from such plants or processed food or food ingredient from such plants) comprising a heterologous expression cassette, the expression cassette comprising a promoter operably linked to a polynucleotide encoding a NPR1 homolog 3 (NH3) polypeptide, wherein the plant expresses the NH3 polypeptide at a higher level than a plant lacking the expression cassette and wherein the plant has enhanced disease resistance compared to the plant lacking the expression cassette.

In some embodiments, the promoter is substantially similar (e.g., has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity) to a native NH3 promoter of the plant. In some embodiments, the promoter is substantially similar (e.g., has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity) to SEQ ID NO:3. In some embodiments, the promoter is tissue-specific, organ-specific, or inducible.

In some embodiments, the polynucleotide encoding the NH3 polypeptide is substantially similar (e.g., has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity) to SEQ ID NO:1. In some embodiments, the polynucleotide encoding the NH3 polypeptide comprises SEQ ID NO:1.

In some embodiments, the polynucleotide encodes a NH3 polypeptide that is substantially similar (e.g., has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity) to any of SEQ ID NOs:2 or 4-19 (i.e., any of SEQ ID NOs:2, 4, 5, 6, 7, 8, 9, 10, 11, 12, 13, 14, 15, 16, 17, 18, or 19). In some embodiments, the polynucleotide encodes a NH3 polypeptide comprising any of SEQ ID NOs:2 or 4-19 (i.e., any of SEQ ID NOs:2, 4, 5, 6, 7, 8, 9, 10, 11, 12, 13, 14, 15, 16, 17, 18, or 19).

In some embodiments, the plant comprising an expression cassette as described herein expresses the NH3 polypeptide at a level from about two-fold higher to about ten-fold higher (e.g., about two-fold, about three-fold, about four-fold, about five-fold, about six-fold, about seven-fold, about eight-fold, about nine-fold, or about ten-fold higher) than the plant lacking the expression cassette.

In some embodiments, the plant (or plant cell, seed, flower, leaf, fruit, or other plant part from such plant or processed food or food ingredient from such plant) comprising an expression cassette as described herein is selected from the group consisting of rice, maize, wheat, soybeans, cotton, canola, turfgrass, and alfalfa. In some embodiments, the plant (or plant cell, seed, flower, leaf, fruit, or other plant part from such plant or processed food or food ingredient from such plant) comprising an expression cassette as described herein is rice.

The present invention also provides for expression cassettes comprising a promoter operably linked to an isolated polynucleotide encoding a NPR1 homolog 3 (NH3) polypeptide, wherein expression of the expression cassette in a plant increases the level of NH3 polypeptide expression of the plant and enhances disease resistance of the plant as compared to a plant in which the expression cassette is not expressed.

In some embodiments, the expression cassette comprises a promoter operably linked to an isolated polynucleotide encoding a NH3 polypeptide, wherein the polynucleotide encoding the NH3 polypeptide is substantially similar (e.g., has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity) to SEQ ID NO:1. In some embodiments, the polynucleotide encoding the NH3 polypeptide comprises SEQ ID NO:1. In some embodiments, the polynucleotide encodes a NH3 polypeptide that is substantially similar (e.g., has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity) to any of SEQ ID NOs:2 or 4-19 (i.e., any of SEQ ID NOs:2, 4, 5, 6, 7, 8, 9, 10, 11, 12, 13, 14, 15, 16, 17, 18, or 19). In some embodiments, the polynucleotide encodes a NH3 polypeptide comprising any of SEQ ID NOs:2 or 4-19 (i.e., any of SEQ ID NOs:2, 4, 5, 6, 7, 8, 9, 10, 11, 12, 13, 14, 15, 16, 17, 18, or 19).

In some embodiments, the expression cassette comprises a promoter operably linked to an isolated polynucleotide encoding a NH3 polypeptide, wherein the promoter is substantially similar (e.g., has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity) to a native NH3 promoter of a wild-type plant. In some embodiments, the promoter is substantially similar (e.g., has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity) to SEQ ID NO:3. In some embodiments, the promoter is tissue-specific, organ-specific, or inducible.

In another aspect, the present invention provides for expression vectors comprising an expression cassette as described herein.

In yet another aspect, the present invention provides for methods of enhancing plant resistance to a pathogen. In some embodiments, the method comprises:
  introducing a nucleic acid comprising a expression cassette into a plant, wherein the expression cassette comprises a promoter operably linked to a polynucleotide encoding a NPR1 homolog 3 (NH3) polypeptide; and
  from the one or more plants into which the nucleic acid comprising the expression cassette has been introduced, selecting a plant with increased resistance to a pathogen or pathogens as compared to resistance of a plant lacking the expression cassette.

In some embodiments, the expression cassette of the method comprises a polynucleotide encoding the NH3 polypeptide that is substantially similar (e.g., has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity) to SEQ ID NO:1. In some embodiments, the polynucleotide encoding the NH3 polypeptide comprises SEQ ID NO:1. In some embodiments, the polynucleotide encodes a NH3 polypeptide that is substantially similar (e.g., has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity) to any of SEQ ID NOs:2 or 4-19 (i.e., any of SEQ ID NOs:2, 4, 5, 6, 7, 8, 9, 10, 11, 12, 13, 14, 15, 16, 17, 18, or 19). In some embodiments, the polynucleotide encodes a NH3 polypeptide comprising any of SEQ ID NOs:2 or 4-19 (i.e., any of SEQ ID NOs:2, 4, 5, 6, 7, 8, 9, 10, 11, 12, 13, 14, 15, 16, 17, 18, or 19).

In some embodiments, the expression cassette of the method comprises a promoter that is substantially similar (e.g., has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity) to a native NH3 promoter of a wild-type plant. In some embodiments, the promoter is substantially similar (e.g., has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity) to SEQ ID NO:3. In some embodiments, the promoter is tissue-specific, organ-specific, or inducible.

DEFINITIONS

Figure 1:
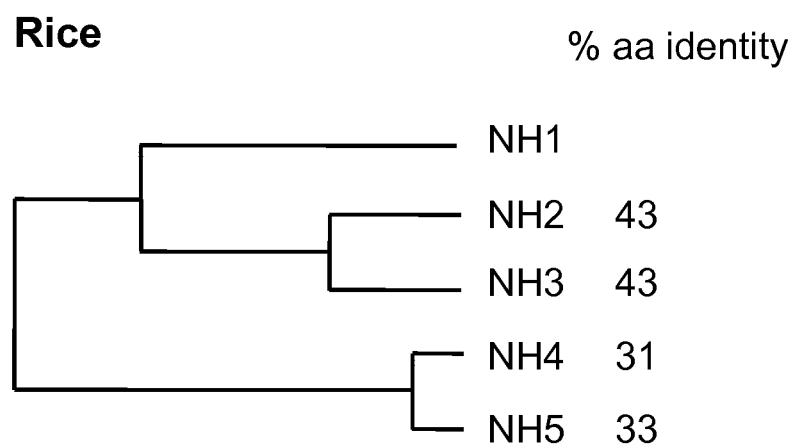
FIG. 1. A phylogenic tree of rice NPR 1-like proteins. Sequences of the five rice NPR1-like proteins are based on TIGR annotations and confirmed by isolated cDNA clones. Sequences are aligned using BlastP. The percentage of amino acid (aa) identity was calculated by comparing individual protein to NH1.

The term "enhanced disease resistance" refers to an increase in the ability of a plant to prevent pathogen infection or pathogen-induced symptoms. Enhanced resistance can be increased resistance relative to a particular pathogen species or genus or can be increased resistance to all pathogens (e.g., systemic acquired resistance).

The terms "NPR1 homolog 3 polypeptide," "OsNPR3 polypeptide," and "NH3 polypeptide" refer to a protein characterized in part by the presence of a bipartite nuclear localization sequence and two protein-protein interaction domains, an ankyrin repeat domain and a BTB/POZ domain, and which, when introduced into a plant, results in enhanced disease resistance. In some embodiments, a NH3 polypeptide comprises a rice NH3 polypeptide (e.g., SEQ ID NO:2) or a polypeptide that is substantially similar to SEQ ID NO:2. In some embodiments, a NH3 polypeptide comprises an ortholog of rice NH3, for example a polypeptide that is identical or substantially similar to any of SEQ ID NOs:4-19.

The term "nucleic acid" or "polynucleotide" refers to a single or double-stranded polymer of deoxyribonucleotide or ribonucleotide bases read from the 5' to the 3' end. Nucleic acids may also include modified nucleotides that permit correct read through by a polymerase and do not significantly alter expression of a polypeptide encoded by that nucleic acid.

The phrase "nucleic acid encoding" or "polynucleotide encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length sequences. It should be further understood that the sequence includes the degenerate codons of the native sequence or sequences which may be introduced to provide codon preference in a specific host cell.

The phrase "host cell" refers to a cell from any organism. Exemplary host cells are derived from plants, bacteria, yeast, fungi, insects or other animals. Methods for introducing polynucleotide sequences into various types of host cells are well known in the art.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

The phrase "substantially similar" or "substantially identical," used in the context of two nucleic acids or polypeptides, refers to a sequence that has at least 50% sequence identity with a reference sequence. Alternatively, percent identity can be any integer from 50% to 100%. Some embodiments include at least: 50%, 55%, 60%, 65%, 70%, 75%, 80%, 85%, 90%, 91%, 92%, 93%, 94% 95%, 96%, 97%, 98%, or 99%, compared to a reference sequence using the programs described herein, e.g., BLAST using standard parameters, as described below. Embodiments of the present invention provide for nucleic acids comprising a sequence that is substantially similar to SEQ ID NOs:1 or 3 across the entire length of the sequence, or polypeptides comprising a sequence that is substantially similar to SEQ ID NOs:2 or 4-19 across the entire length of the sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
(see, e.g., Creighton, Proteins (1984)).

A polynucleotide sequence is "heterologous" to an organism or a second polynucleotide sequence if it originates from a foreign species, or, if from the same species, is modified from its original form. For example, when a promoter is said to be operably linked to a heterologous coding sequence, it means that the coding sequence is derived from one species whereas the promoter sequence is derived another, different species; or, if both are derived from the same species, the coding sequence is not naturally associated with the promoter (e.g., is a genetically engineered coding sequence, e.g., from a different gene in the same species, or an allele from a different ecotype or variety).

An "expression cassette" refers to a nucleic acid construct that, when introduced into a host cell, results in transcription and/or translation of an RNA or polypeptide, respectively. Antisense or sense constructs that are not or cannot be translated are expressly included by this definition. In the case of both expression of transgenes and suppression of endogenous genes (e.g., by antisense, or sense suppression) one of skill will recognize that the inserted polynucleotide sequence need not be identical, but may be only substantially similar to a sequence of the gene from which it was derived. As explained herein, these substantially similar variants are specifically covered by reference to a specific nucleic acid sequence.

The term "promoter," as used herein, refers to a polynucleotide sequence capable of driving transcription of a coding sequence in a cell. Thus, promoters used in the polynucleotide constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. A "plant promoter" is a promoter capable of initiating transcription in plant cells. A "constitutive promoter" is one that is capable of initiating transcription in nearly all tissue types, whereas a "tissue-specific promoter" initiates transcription only in one or a few particular tissue types.

The term "plant" includes whole plants, shoot vegetative organs and/or structures (e.g., leaves, stems and tubers), roots, flowers and floral organs (e.g., bracts, sepals, petals, stamens, carpels, anthers), ovules (including egg and central cells), seed (including zygote, embryo, endosperm, and seed coat), fruit (e.g., the mature ovary), seedlings, plant tissue (e.g., vascular tissue, ground tissue, and the like), cells (e.g., guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid, and hemizygous.

"Pathogens" include, but are not limited to, viruses, bacteria, nematodes, fungi or insects (see, e.g., Agrios, *Plant Pathology* (Academic Press, San Diego, Calif. (1988)).

DETAILED DESCRIPTION OF THE INVENTION

I. Introduction

As described in the Examples section, the inventors have surprisingly discovered that introduction of an extra copy of NPR homolog 3 (NH3) driven by its own promoter into plants results in plants with enhanced disease resistance. Generally, the plants of the invention express NH3 at a higher level, in some cases two-fold, three-fold, or four-fold, higher, than plants into which the extra copy of NH3 has not been introduced.

II. NH3 Proteins

In rice, there are five NPR1-like proteins, namely NH1, NH2, NH3, NH4, and NH5 (NPR1 homologs 1-5), encoded by six genes (TIGR gene ID Os01g09800, Os01g56200, Os03g46440, Os01g72020, Os11g04600, and Os12g04410) in the genome. Protein NH5 is encoded by two duplicate genes, Os11g04600 and Os12g04410, which are recently duplicated genes due to chromosomal segmental duplication (Jacquemin et al., 2009). In *Arabidopsis*, the six NPR1-like proteins are divided into three groups with each group containing two proteins (Liu et al., 2005). As depicted in FIG. 1, the five rice NPR1-like proteins can also be divided into three groups based on BLAST search results: NH1 in group 1, NH2 and NH3 in group 2, and NH4 and NH5 in group 3. Thus, unlike in *Arabidopsis*, rice NH1 is most unique in sequence among rice NPR1-like proteins.

The identity levels across different groups of rice NPR1-like proteins are higher than those in *Arabidopsis*. For example, in *Arabidopsis* NPR1 shares about 35% identity with group 2 and 20% identity with group 3, while in rice NH1 shares 43% identity with group 2 and 31% identity with group 3. These data indicate that the five rice NPR1-like proteins are closer in identity to each other than the six *Arabidopsis* NPR1-like proteins are to each other. Within groups, rice NH2 shares 54% identity with NH3 while NH4 shares 62% identity with NH5. Between rice and *Arabidopsis*, rice NH1 shares the highest homology with *Arabidopsis* NPR1 and NPR2, carrying 46% identity and 66% similarity with NPR1 and 46% identity and 64% similarity with NPR2. NH2 has the highest homology to *Arabidopsis* NPR3 and NPR4, sharing 51% identity and 69% similarity with NPR3 and 51% identity and 70% similarity with NPR4; NH3 also shares the highest homology with *Arabidopsis* NPR3 and NPR4, carrying 48% identity and 65% similarity with NPR3 and 46% identity and 65% similarity with NPR4. NH4 is most homologous to *Arabidopsis* BOP2 (NPR5), sharing 70% identity and 78% similarity; NH5 is most homologous to *Arabidopsis* BOP1 (NPR6), sharing 65% identity and 78% similarity.

In some embodiments, the NH3 protein comprises SEQ ID NO:2, the rice NH3 protein sequence. Those of skill in the art will appreciate that variants of the rice NH3 protein sequence can be obtained either by identifying additional NH3 ortholog sequences from other plants, or by generating directed or random mutations in the sequences. In some embodiments, the NH3 protein is substantially similar to (e.g., at least 50%, 55%, 60%, 65%, 70%, 75%, 80%, 85%, 90%, 91%, 92%, 93%, 94% 95%, 96%, 97%, 98%, or 99% identical to) SEQ ID NO:2. In some embodiments, the NH3 protein is identical or substantially similar to any of SEQ ID NOs:4, 5, 6, 7, 8, 9, 10, 11, 12, 13, 14, 15, 16, 17, 18, or 19.

Embodiments of the present invention provide for use of the above proteins and/or nucleic acid sequences, encoding such polypeptides, in the methods and compositions (e.g., expression cassettes, plants, etc.) of the present invention. The isolation of a polynucleotide sequence encoding a NH3 protein may be accomplished by a number of techniques. For instance, oligonucleotide probes based on the NH3 coding sequences disclosed (e.g., as listed in the SEQUENCE LISTING) here can be used to identify the desired NH3 gene in a cDNA or genomic DNA library. To construct genomic libraries, large segments of genomic DNA are generated by random fragmentation, e.g., using restriction endonucleases, and are ligated with vector DNA to form concatemers that can be packaged into the appropriate vector. To prepare a cDNA library, mRNA is isolated from the desired tissue, such as a leaf from a particular plant species, and a cDNA library containing the gene transcript of interest is prepared from the mRNA. Alternatively, cDNA may be prepared from mRNA extracted from other tissues in which the NH3 gene is expressed.

The cDNA or genomic library can then be screened using a probe based upon the sequence of a NH3 gene disclosed here. Probes may be used to hybridize with genomic DNA or cDNA sequences to isolate homologous genes in the same or different plant species. Alternatively, antibodies raised against a polypeptide can be used to screen an mRNA expression library.

Alternatively, the nucleic acid encoding the NH3 protein can be amplified from nucleic acid samples using amplification techniques. For instance, polymerase chain reaction (PCR) technology can be used to amplify the coding sequences of NH3 directly from genomic DNA, from cDNA, from genomic libraries, or cDNA libraries. PCR and other in vitro amplification methods may also be useful, for example, to clone polynucleotide sequences encoding NH3 to be expressed, to make nucleic acids to use as probes for detecting the presence of the desired mRNA in samples, for nucleic acid sequencing, or for other purposes. For a general overview of PCR see *PCR Protocols: A Guide to Methods and Applications* (Innis, M., Gelfand, D., Sninsky, J. and White, T., eds.), Academic Press, San Diego (1990)). Appropriate primers and probes for identifying sequences from plant tissues are generated from comparisons of the sequences provided here with other related genes.

In some embodiments, the partial or entire genome of a number of plants has been sequenced and open reading frames identified. By a BLAST search, one can identify the coding sequence for a NH3 protein in various plants.

III. Recombinant Expression Vectors

Once a polynucleotide sequence encoding a NH3 polypeptide is obtained, it can be used to prepare an expression cassette for expressing the NH3 polypeptide in a transgenic plant, directed by a native or heterologous promoter. Increased expression of the NH3 polypeptide is useful, for example, to produce plants that have enhanced disease resistance, such as resistance to diseases induced by pathogens or resistance to diseases induced by chemicals such as BTH, compared to plants that do not have increased expression of the NH3 polypeptide.

Any of a number of means well known in the art can be used to drive NH3 expression in plants. Any organ can be targeted, such as shoot vegetative organs/structures (e.g.

leaves, stems and tubers), roots, flowers and floral organs/ structures (e.g. bracts, sepals, petals, stamens, carpels, anthers and ovules), seed (including embryo, endosperm, and seed coat) and fruit. Alternatively, expression of the NH3 can be conditioned to only occur under certain conditions (e.g., using an inducible promoter).

To use isolated sequences in the above techniques, recombinant DNA vectors suitable for transformation of plant cells are prepared. Techniques for transforming a wide variety of higher plant species are well known and described in the technical and scientific literature, e.g., Weising et al. *Ann. Rev. Genet.* 22:421-477 (1988). A DNA sequence coding for the desired polypeptide, for example the NH3 polypeptides as described herein, will be combined with transcriptional and translational initiation regulatory sequences which will direct the transcription of the sequence from the gene in the intended tissues of the transformed plant.

For example, a plant promoter fragment may be employed to direct expression of the NH3 polypeptide in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill.

Alternatively, the plant promoter may direct expression of the NH3 polypeptide in a specific tissue (tissue-specific promoters) or may be otherwise under more precise environmental control (inducible promoters). Examples of tissue-specific promoters under developmental control include promoters that initiate transcription only in certain tissues, such as leaves or guard cells (including but not limited to those described in WO/2005/085449; U.S. Pat. No. 6,653, 535; Li et al., *Sci China C Life Sci.* 2005 April; 48(2):181-6; Husebye, et al., *Plant Physiol*, April 2002, Vol. 128, pp. 1180-1188; and Plesch, et al., *Gene*, Volume 249, Number 1, 16 May 2000, pp. 83-89(7)). Examples of environmental conditions that may affect transcription by inducible promoters include anaerobic conditions, elevated temperature, or the presence of light.

If proper protein expression is desired, a polyadenylation region at the 3'-end of the coding region should be included. The polyadenylation region can be derived from a NH3 gene, from a variety of other plant genes, or from T-DNA.

Optionally, the polypeptide may comprise a protein tag that facilitates detection or purification of the polypeptide. The tag may be added to the N-terminal or C-terminal region of the polypeptide or internally within the polypeptide. Examples of suitable tags include, but are not limited to, Myc, FLAG, HA, His, glutathione-S-transferase (GST), tandem affinity purification (TAP), and fluorescent protein (e.g., GFP, YFP, EGFP, RFP, DsRed) tags.

The vector comprising the sequences (e.g., promoters or NH3 coding regions) will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

In some embodiments, the promoter that is operably linked to a polynucleotide encoding a NH3 polypeptide increases the level of expression of NH3 in a transgenic plant into which the promoter operably linked to the polynucleotide encoding the NH3 polypeptide has been introduced. In some embodiments, the level of expression increases from about two-fold to about ten-fold in a transgenic plant comprising the promoter operably linked to the polynucleotide encoding the NH3 polypeptide, compared to a plant lacking the promoter operably linked to the polynucleotide encoding the NH3 polypeptide.

Native Promoters

In some embodiments, expression of a NH3 nucleic acid may be directed by its own native promoter or a portion thereof. In some embodiments, a "portion" of a promoter comprises a continuous length of a promoter sequence that is from about 100 nucleotides in length to about 10,000 nucleotides in length. In some embodiments, a portion of a promoter comprises a continuous length of a promoter sequence that is from about 500 nucleotides in length to about 5,000 nucleotides in length. The term "native" means the naturally occurring promoter sequence that directs naturally occurring NH3 expression in a plant. A native promoter that is operably linked to a polynucleotide of interest, e.g. a NH3 polynucleotide of the present invention, will direct expression of that polynucleotide of interest in those cell and tissue types, or during those environmental conditions and states of development or cell differentiation, in which the native promoter would drive expression under physiological conditions.

A native promoter or promoter element or portion thereof may be located either upstream or downstream of the gene coding sequence which is controlled by the promoter. In some embodiments, the native promoter comprises the nucleotide sequence upstream of the NH3 gene (also called OsNPR3) in rice. In some embodiments, the native promoter comprises the nucleotide sequence of SEQ ID NO:3 or a portion thereof (e.g., about 100, 200, 300, 400, 500, 600, 700, 800, or 900 contiguous nucleotides of SEQ ID NO:3) or a nucleotide sequence substantially similar to SEQ ID NO:3 or a portion thereof (e.g., about 100, 200, 300, 400, 500, 600, 700, 800, or 900 contiguous nucleotides of SEQ ID NO:3).

A native promoter operably linked to a polynucleotide encoding a polypeptide of interest, e.g. a NH3 polypeptide of the present invention, will express the NH3 polynucleotide under those physiological conditions in which the native promoter would normally direct gene expression. The native promoter may be operably linked to an identical or substantially similar polynucleotide as is normally expressed by the native promoter. For example, the native NH3 promoter in rice may be operably linked to a polynucleotide encoding the rice NH3 polypeptide; the native NH3 promoter in maize may be operably linked to a polynucleotide encoding the maize NH3 polypeptide ortholog; the native NH3 promoter in soybean may be operably linked to a polynucleotide encoding the soybean NH3 polypeptide ortholog; the native NH3 promoter in wheat may be operably linked to a polynucleotide encoding the wheat NH3 polypeptide ortholog; etc. Alternatively, the native promoter may be operably linked to a polynucleotide that is not identical, but is substantially similar, to the polynucleotide that is normally expressed by the native promoter. For example, the native NH3 promoter in rice may be operably linked to a polynucleotide encoding the maize NH3 polypeptide ortholog, soybean NH3 polypeptide ortholog, wheat NH3 polypeptide ortholog, etc.; or alternatively, the native NH3 promoter in maize, soybean, wheat, etc., may be operably linked to a polynucleotide encoding the rice NH3 polypeptide such as the polynucleotide of SEQ ID NO:1.

Inducible Promoters

Alternatively, a plant promoter may direct expression of the NH3 polynucleotide under the influence of changing environmental conditions or developmental conditions. Examples of environmental conditions that may effect transcription by inducible promoters include anaerobic conditions, elevated temperature, drought, or the presence of light. Such promoters are referred to herein as "inducible" promoters.

Exemplary inducible promoters include those promoters that are specifically induced upon infection by a virulent pathogen. Selected promoters useful in the invention are discussed in PCT application WO 99/43824, and include promoters from:
- a. lipoxygenases (e.g., Peng et al, J. Biol. Chem. 269: 3755-3761 (1994)),
- b. peroxidases (e.g., Chittoor et al. Molec. Plant-Microbe Interact. 10:861-871 (1997)),
- c. hydroxymethylglutaryl-CoA reductase,
- d. phenylalanine ammonia lyase,
- e. glutathione-S-transferase,
- f. chitinases (e.g., Zhu et al. Mol. Gen. Genet. 226:289-296 (1991)),
- g. genes involved in the plant respiratory burst (e.g., Groom et al. Plant J. 10(3):515-522 (1996)); and
- h. pathogenesis-related (PR) protein promoters.

Alternatively, plant promoters which are inducible upon exposure to plant hormones, such as auxins, are used to express the NH3 polynucleotide. For example, the invention can use the auxin-response elements E1 promoter fragment (AuxREs) in the soybean (*Glycine max* L.) (Liu (1997) *Plant Physiol*. 115:397-407); the auxin-responsive *Arabidopsis* GST6 promoter (also responsive to salicylic acid and hydrogen peroxide) (Chen (1996) *Plant J*. 10: 955-966); the auxin-inducible parC promoter from tobacco (Sakai (1996) 37:906-913); a plant biotin response element (Streit (1997) *Mol. Plant. Microbe Interact*. 10:933-937); and, the promoter responsive to the stress hormone abscisic acid (Sheen (1996) *Science* 274:1900-1902).

Plant promoters inducible upon exposure to chemical reagents that may be applied to the plant, such as herbicides or antibiotics, are also useful for expressing the NH3 polynucleotide. For example, the maize In2-2 promoter, activated by benzenesulfonamide herbicide safeners, can be used (De Veylder (1997) *Plant Cell Physiol*. 38:568-577); application of different herbicide safeners induces distinct gene expression patterns, including expression in the root, hydathodes, and the shoot apical meristem. A NH3 coding sequence can also be under the control of, e.g., a tetracycline-inducible promoter, e.g., as described with transgenic tobacco plants containing the *Avena sativa* L. (oat) arginine decarboxylase gene (Masgrau (1997) *Plant J*. 11:465-473); or, a salicylic acid-responsive element (Stange (1997) *Plant J*. 11:1315-1324; Uknes et al., *Plant Cell* 5:159-169 (1993); Bi et al., *Plant J*. 8:235-245 (1995)).

Examples of useful inducible regulatory elements include copper-inducible regulatory elements (Mett et al., *Proc. Natl. Acad. Sci. USA* 90:4567-4571 (1993); Furst et al., *Cell* 55:705-717 (1988)); tetracycline and chlor-tetracycline-inducible regulatory elements (Gatz et al., *Plant J*. 2:397-404 (1992); Roder et al., *Mol. Gen. Genet*. 243:32-38 (1994); Gatz, *Meth. Cell Biol*. 50:411-424 (1995)); ecdysone inducible regulatory elements (Christopherson et al., *Proc. Natl. Acad. Sci. USA* 89:6314-6318 (1992); Kreutzweiser et al., *Ecotoxicol. Environ. Safety* 28:14-24 (1994)); heat shock inducible regulatory elements (Takahashi et al., *Plant Physiol*. 99:383-390 (1992); Yabe et al., *Plant Cell Physiol*. 35:1207-1219 (1994); Ueda et al., *Mol. Gen. Genet*. 250: 533-539 (1996)); and lac operon elements, which are used in combination with a constitutively expressed lac repressor to confer, for example, IPTG-inducible expression (Wilde et al., *EMBO J*. 11:1251-1259 (1992)). An inducible regulatory element useful in the transgenic plants of the invention also can be, for example, a nitrate-inducible promoter derived from the spinach nitrite reductase gene (Back et al., *Plant Mol. Biol*. 17:9 (1991)) or a light-inducible promoter, such as that associated with the small subunit of RuBP carboxylase or the LHCP gene families (Feinbaum et al., *Mol. Gen. Genet*. 226:449 (1991); Lam and Chua, *Science* 248:471 (1990)).

Tissue-Specific Promoters

Alternatively, the plant promoter may direct expression of the NH3 polypeptide in a specific tissue (tissue-specific promoters). Tissue specific promoters are transcriptional control elements that are only active in particular cells or tissues at specific times during plant development, such as in vegetative tissues or reproductive tissues.

Examples of tissue-specific promoters under developmental control include promoters that initiate transcription only (or primarily only) in certain tissues, such as vegetative tissues, e.g., roots or leaves, or reproductive tissues, such as fruit, ovules, seeds, pollen, pistils, flowers, or any embryonic tissue, or epidermis or mesophyll. Reproductive tissue-specific promoters may be, e.g., ovule-specific, embryo-specific, endosperm-specific, integument-specific, seed and seed coat-specific, pollen-specific, petal-specific, sepal-specific, or some combination thereof. In some embodiments, the promoter is cell-type specific, e.g., guard cell-specific.

Other tissue-specific promoters include seed promoters. Suitable seed-specific promoters are derived from the following genes: MAC1 from maize (Sheridan (1996) *Genetics* 142:1009-1020); Cat3 from maize (GenBank No. L05934, Abler (1993) *Plant Mol. Biol*. 22:10131-1038); vivparous-1 from *Arabidopsis* (Genbank No. U93215); atmyc1 from *Arabidopsis* (Urao (1996) *Plant Mol. Biol*. 32:571-57; Conceicao (1994) *Plant* 5:493-505); napA from *Brassica napus* (GenBank No. J02798, Josefsson (1987) JBL 26:12196-1301); and the napin gene family from *Brassica napus* (Sjodahl (1995) *Planta* 197:264-271).

A variety of promoters specifically active in vegetative tissues, such as leaves, stems, roots and tubers, can also be used to express polynucleotides encoding NH3 polypeptides. For example, promoters controlling patatin, the major storage protein of the potato tuber, can be used, see, e.g., Kim (1994) *Plant Mol. Biol*. 26:603-615; Martin (1997) *Plant J*. 11:53-62. The ORF13 promoter from *Agrobacterium rhizogenes* that exhibits high activity in roots can also be used (Hansen (1997) *Mol. Gen. Genet*. 254:337-343. Other useful vegetative tissue-specific promoters include: the tarin promoter of the gene encoding a globulin from a major taro (*Colocasia esculenta* L. Schott) corm protein family, tarin (Bezerra (1995) *Plant Mol. Biol*. 28:137-144); the curculin promoter active during taro corm development (de Castro (1992) *Plant Cell* 4:1549-1559) and the promoter for the tobacco root-specific gene TobRB7, whose expression is localized to root meristem and immature central cylinder regions (Yamamoto (1991) *Plant Cell* 3:371-382).

Leaf-specific promoters, such as the ribulose biphosphate carboxylase (RBCS) promoters can be used. For example, the tomato RBCS1, RBCS2 and RBCS3A genes are expressed in leaves and light-grown seedlings, only RBCS1 and RBCS2 are expressed in developing tomato fruits (Meier (1997) *FEBS Lett*. 415:91-95). A ribulose bisphosphate carboxylase promoters expressed almost exclusively in mesophyll cells in leaf blades and leaf sheaths at high levels, described by Matsuoka (1994) *Plant J.* 6:311-319, can be used. Another leaf-specific promoter is the light harvesting chlorophyll a/b binding protein gene promoter, see, e.g., Shiina (1997) *Plant Physiol.* 115:477-483; Casal (1998) *Plant Physiol.* 116:1533-1538. The *Arabidopsis thaliana* myb-related gene promoter (Atmyb5) described by Li (1996) *FEBS Lett.* 379:117-121, is leaf-specific. The Atmyb5 promoter is expressed in developing leaf trichomes, stipules, and epidermal cells on the margins of young rosette and cauline leaves, and in immature seeds. Atmyb5 mRNA appears between fertilization and the 16 cell stage of embryo development and persists beyond the heart stage. A leaf promoter identified in maize by Busk (1997) *Plant J.* 11:1285-1295, can also be used.

Another class of useful vegetative tissue-specific promoters are meristematic (root tip and shoot apex) promoters. For example, the "SHOOTMERISTEMLESS" and "SCARECROW" promoters, which are active in the developing shoot or root apical meristems, described by Di Laurenzio (1996) *Cell* 86:423-433; and, Long (1996) *Nature* 379:66-69; can be used. Another useful promoter is that which controls the expression of 3-hydroxy-3-methylglutaryl coenzyme A reductase HMG2 gene, whose expression is restricted to meristematic and floral (secretory zone of the stigma, mature pollen grains, gynoecium vascular tissue, and fertilized ovules) tissues (see, e.g., Enjuto (1995) *Plant Cell.* 7:517-527). Also useful are knl-related genes from maize and other species which show meristem-specific expression, see, e.g., Granger (1996) *Plant Mol. Biol.* 31:373-378; Kerstetter (1994) *Plant Cell* 6:1877-1887; Hake (1995) *Philos. Trans. R. Soc. Lond. B. Biol. Sci.* 350:45-51. For example, the *Arabidopsis thaliana* KNAT1 promoter (see, e.g., Lincoln (1994) *Plant Cell* 6:1859-1876).

One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

In another embodiment, a nucleic acid described in the present invention is expressed through a transposable element. This allows for constitutive, yet periodic and infrequent expression of the constitutively active polypeptide. The invention also provides for use of tissue-specific promoters derived from viruses which can include, e.g., the tobamovirus subgenomic promoter (Kumagai (1995) *Proc. Natl. Acad. Sci. USA* 92:1679-1683) the rice tungro baciliform virus (RTBV), which replicates only in phloem cells in infected rice plants, with its promoter which drives strong phloem-specific reporter gene expression; the cassava vein mosaic virus (CVMV) promoter, with highest activity in vascular elements, in leaf mesophyll cells, and in root tips (Verdaguer (1996) *Plant Mol. Biol.* 31:1129-1139).

IV. Production of Transgenic Plants

As detailed herein, embodiments of the present invention provide for transgenic plants comprising recombinant expression cassettes for expressing a NH3 polypeptide as described herein. In some embodiments, a transgenic plant is generated that contains a complete or partial sequence of a polynucleotide that is derived from a species other than the species of the transgenic plant. It should be recognized that transgenic plants encompass the plant or plant cell in which the expression cassette is introduced as well as progeny of such plants or plant cells that contain the expression cassette, including the progeny that have the expression cassette stably integrated in a chromosome.

In some embodiments, the transgenic plants comprising recombinant expression cassettes for expressing a NH3 polypeptide express NH3 at higher levels than a plant lacking the recombinant expression cassette for expressing a NH3 polypeptide. In some embodiments, the transgenic plants comprising recombinant expression cassettes for expressing a NH3 polypeptide express NH3 at levels that are from about two-fold to about four-fold higher than a plant lacking the recombinant expression cassette for expressing a NH3 polypeptide.

In some embodiments, the transgenic plants comprising recombinant expression cassettes for expressing a NH3 polypeptide express NH3 at a level that results in increased disease resistance compared to a plant lacking the recombinant expression cassette for expressing a NH3 polypeptide, wherein the transgenic plants comprising recombinant expression cassettes for expressing a NH3 polypeptide have about the same growth as a plant lacking the recombinant expression cassette for expressing a NH3 polypeptide. In some embodiments, the transgenic plant comprising a recombinant expression cassette for expressing a NH3 polypeptide has no more than about a 10% reduction in growth compared to a plant lacking the recombinant expression cassette for expressing a NH3 polypeptide. In some embodiments, the transgenic plant comprising a recombinant expression cassette for expressing a NH3 polypeptide does not produce significantly more lesion mimics compared to a plant lacking the recombinant expression cassette for expressing a NH3 polypeptide.

A recombinant expression vector comprising a NH3 coding sequence driven by promoter may be introduced into the genome of the desired plant host by a variety of conventional techniques. For example, the DNA construct may be introduced directly into the genomic DNA of the plant cell using techniques such as electroporation and microinjection of plant cell protoplasts, or the DNA construct can be introduced directly to plant tissue using ballistic methods, such as DNA particle bombardment. Alternatively, the DNA construct may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. While transient expression of NH3 is encompassed by the invention, generally expression of construction of the invention will be from insertion of expression cassettes into the plant genome, e.g., such that at least some plant offspring also contain the integrated expression cassette.

Microinjection techniques are also useful for this purpose. These techniques are well known in the art and thoroughly described in the literature. The introduction of DNA constructs using polyethylene glycol precipitation is described in Paszkowski et al. *EMBO J.* 3:2717-2722 (1984). Electroporation techniques are described in Fromm et al. *Proc. Natl. Acad. Sci. USA* 82:5824 (1985). Ballistic transformation techniques are described in Klein et al. *Nature* 327:70-73 (1987).

*Agrobacterium tumefaciens*-mediated transformation techniques, including disarming and use of binary vectors, are well described in the scientific literature. See, for example, Horsch et al. *Science* 233:496-498 (1984), and Fraley et al. *Proc. Natl. Acad. Sci. USA* 80:4803 (1983).

Transformed plant cells derived by any of the above transformation techniques can be cultured to regenerate a whole plant that possesses the transformed genotype and thus the desired phenotype such as enhanced disease resistance. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467-486 (1987).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The expression cassettes of the invention can be used to confer disease resistance on essentially any plant. Thus, the invention has use over a broad range of plants, including species from the genera *Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, Vitis, Vigna,* and, *Zea.* In some embodiments, the plant is selected from the group consisting of rice, maize, wheat, soybeans, cotton, canola, turfgrass, and alfalfa. In some embodiments, the plant is an ornamental plant. In some embodiments, the plant is a vegetable- or fruit-producing plant. In some embodiments, the plant is a monocot. In some embodiments, the plant is a dicot.

V. Selecting for Plants with Enhanced Disease Resistance

Plants with enhanced resistance can be selected in many ways. One of ordinary skill in the art will recognize that the following methods are but a few of the possibilities. One method of selecting plants with enhanced resistance is to determine resistance of a plant to a specific plant pathogen. Possible pathogens include, but are not limited to, viruses, bacteria, nematodes, fungi or insects (see, e.g., Agrios, *Plant Pathology* (Academic Press, San Diego, Calif.) (1988)). Alternatively, another method of selecting plants with enhanced resistance is to determine resistance of a plant to a specific compound that induces Systemic Acquired Resistance. Such compounds include, but are not limited to, salicylic acid, 2,6-dichloroisonicotinic acid (INA), benzothiadiazole (BTH), and probenazole (see, e.g., Ward et al., 1991; Gorlach et al., 1996; Schweizer et al., 1999; and Morris et al., 1998)). One of skill in the art will recognize that resistance responses of plants vary depending on many factors, including what pathogen, compound, or plant is used. Generally, enhanced resistance is measured by the reduction or elimination of disease symptoms when compared to a control plant. In some cases, however, enhanced resistance can also be measured by the production of the hypersensitive response (HR) of the plant (see, e.g., Staskawicz et al. (1995) *Science* 268(5211): 661-7). Plants with enhanced resistance can produce an enhanced hypersensitive response relative to control plants.

Enhanced resistance can also be determined by measuring the increased expression of a gene operably linked a defense related promoter. Measurement of such expression can be measured by quantifying the accumulation of RNA or subsequent protein product (e.g., using northern or western blot techniques, respectively (see, e.g., Sambrook et al. and Ausubel et al.). A possible alternate strategy for measuring defense gene promoter expression involves operably linking a reporter gene to the promoter. Reporter gene constructs allow for ease of measurement of expression from the promoter of interest. Examples of reporter genes include: β-gal, GUS (see, e.g., Jefferson, R. A., et al., (1987) *EMBO J.* 6:3901-3907), green fluorescent protein, luciferase, and others.

EXAMPLES

The following examples are offered to illustrate, but not limit the claimed invention.

NPR1 (nonexpresser of pathogenesis related genes 1) is the master regulator of salicylic acid-mediated systemic acquired resistance. Overexpression of *Arabidopsis* NPR1 and rice NH1 (NPR1 homolog1)/OsNPR1 in rice results in enhanced resistance. While there are four rice NPR1 paralogs in the rice genome, none have been demonstrated to function in disease resistance. To study rice NPR1 paralog 3, we introduced constructs into rice and tested for effects on resistance to infection by *Xanthomonas oryzae* pv. *oryzae* (Xoo), the causal agent of bacterial blight. While overexpression of NH3 using the maize ubiquitin-1 promoter failed to enhance resistance, introduction of an extra copy of NH3 driven by its own promoter (nNT-NH3) resulted in clear, enhanced resistance. Progeny analysis confirms that the enhanced resistance phenotype, measured by Xoo-induced lesion length, is associated with the NH3 transgene. Bacterial growth curve analysis indicates that bacterial population levels are reduced 10-fold in nNT-NH3 lines compared to control rice lines. The transgenic plants exhibit higher sensitivity to BTH (benzothiadiazole) and INA (2,6-dichloroisonicotinic acid) treatment as measured by increased cell death. Expression analysis of pathogenesis-related (PR) genes showed that nNT-NH3 plants display greatly enhanced induction of PR genes only after treatment with BTH. Our study demonstrates an alternative method to employ a regulatory protein to enhance plant defense. This approach avoids using undesirable constitutive, high-level expression and may prove to be more practical for engineering resistance.

Figure 2:
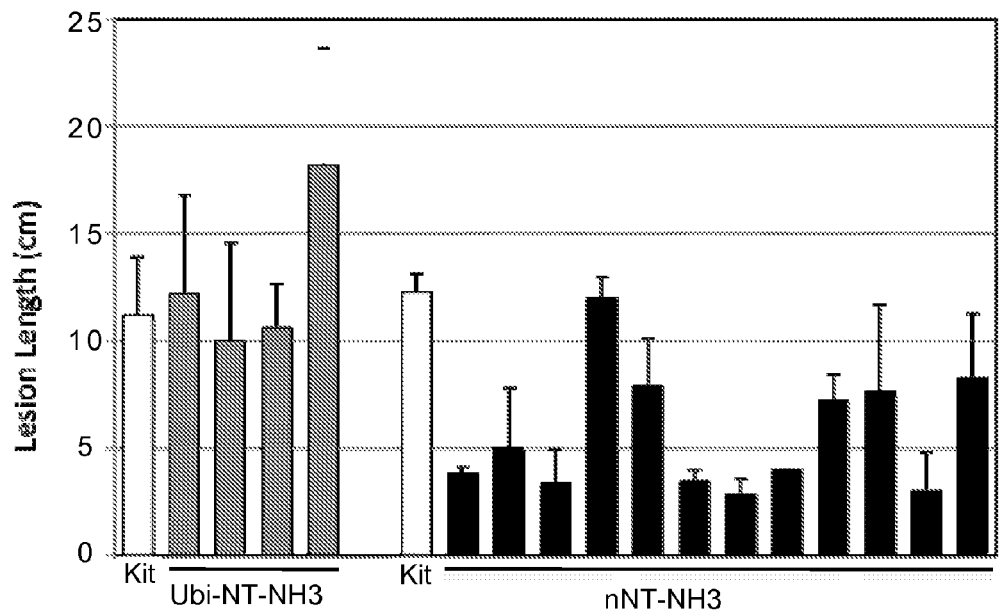
FIG. 2. Lesion length measurements of NH3 transgenic plants. A. Resistance analysis of T0 plants. Four Ubi-NT-NH3 (grey bars) and 12 nNT-NH3 (filled bars) T0 transgenic plants were inoculated with PXO99 and lesion lengths were measured two weeks after inoculation. Wild-type Kitaake (Kit) plants were included as control (open bars). Each bar represents the average and standard deviation of two to five leaves. B. Enhanced resistance and transgene co-segregation analysis. T1 progeny from three T0 lines (#3A, #6A, and #13A) of nNT-NH3 transgenic plants were genotyped by PCR for the presence of the nNT-NH3 transgene. The progeny containing the transgene are presented as filled bars and null segregants, which no longer contain the gene, are as open bars. Kit plants were included as control (open bars). Six weeks old plants were inoculated with PXO99 and lesion lengths measured in two weeks. On average three to four leaves were inoculated. The error bars represent standard deviations.
Figure 2:
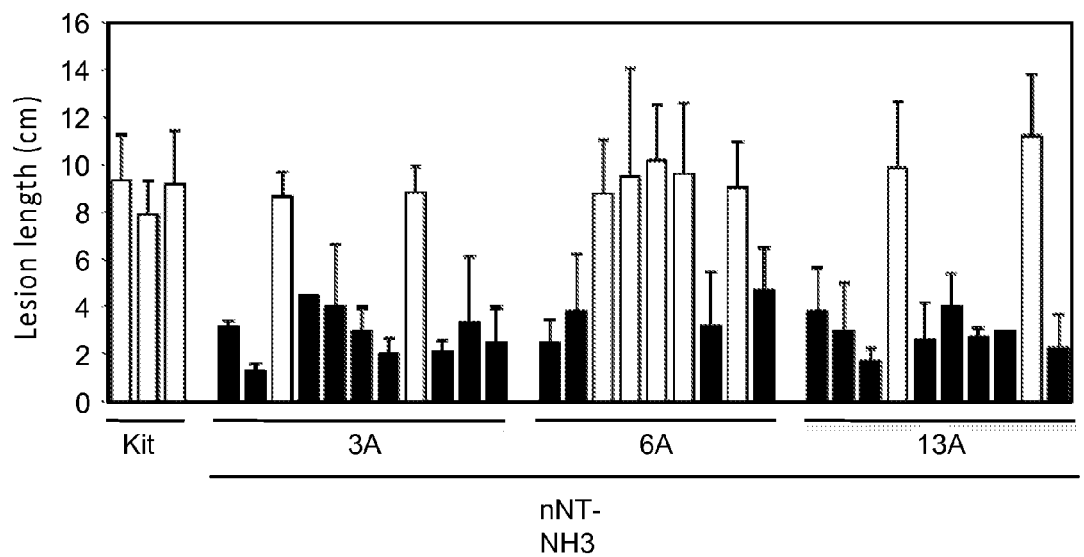
Figure 3:
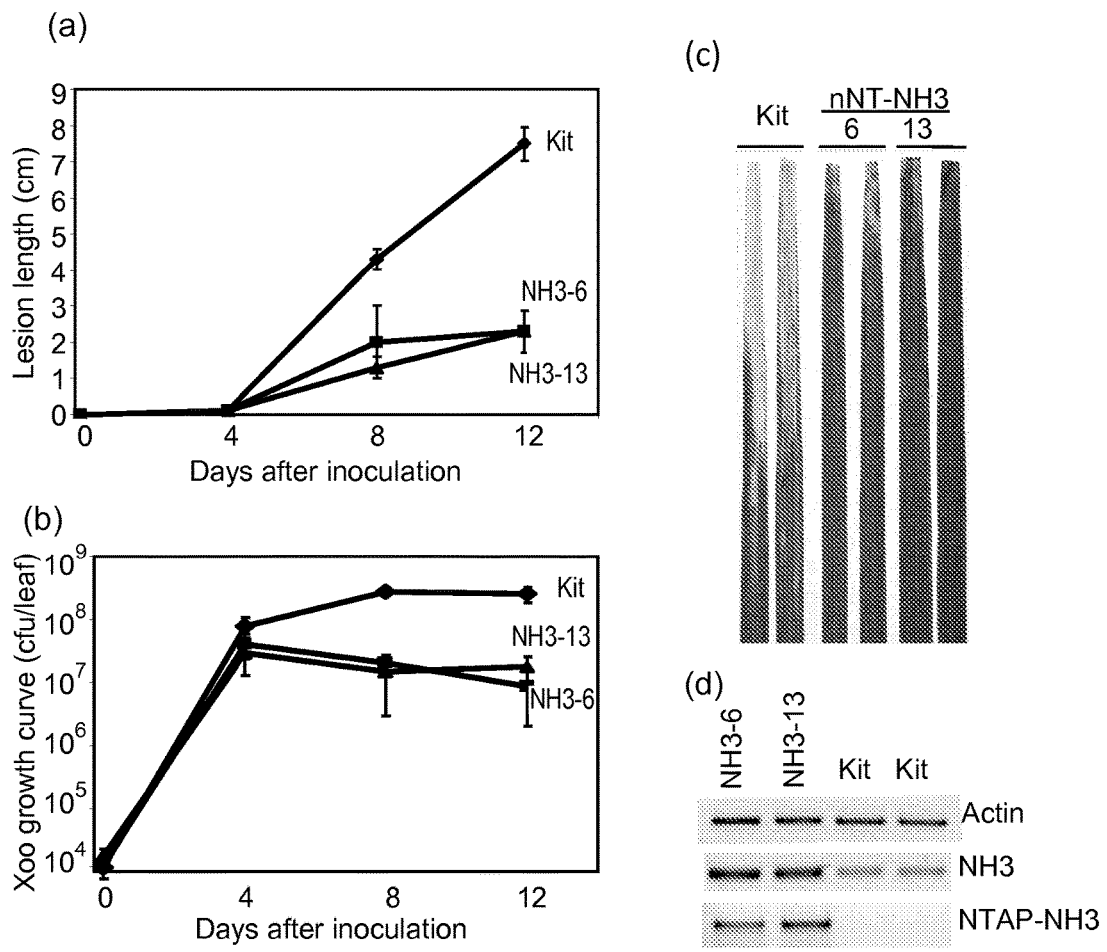
FIG. 3. Analysis of nNT-NH3 lines #6A and #13A. A. Lesion development. Progeny of nNT-NH3 lines #6A and #13A (labeled NH3-6 and NH3-13) were first genotyped. Those containing the nNT-NH3 transgene were pooled to represent the line and inoculated with PXO99. Lesion lengths were measured at days 0, 4, 8, and 12, after inoculation. Each data point represents the average and standard deviation of three leaf samples. B. Bacterial growth curves. Inoculated leaf samples described in (a) were used to extract Xoo for growth curve analysis. C. Leaf lesions caused by Xoo. Two representative leaves, each from Kit control, NH3-6, and NH3-13, two weeks after PXO99 inoculation are shown. D. RT-PCR results. Total RNA samples were extracted from NH3-6, NH3-13, and Kit. An equal amount of RNA was reverse-transcribed and the cDNA was used for RT-PCR. The amounts of input cDNA were further equalized based on expression of actin. The expression of the NH3 genes (including endogenous and the nNT-NH3 transgene) was measured by targeting the NH3 transcripts. The expression of the nNT-NH3 transgene (labeled NTAP-NH3) was measured by using one primer targeting the NTAP tag and the other targeting NH3.

Construct Using the Ubi-1 Promoter to Overexpress NH3 Yielded No Transgenic Plants with Enhanced Resistance Overexpression is a useful tool to study of the possible function of a gene of interest. The Ubi-1 promoter is commonly used for such purpose because of its ability to express a gene to very high levels, especially in monocots, including rice. In an attempt to study possible involvement of rice NH1 paralogs in disease resistance, we tried to overexpress the rice NH3 (also called OsNPR3) gene using the maize Ubi-1 promoter in the Kitaake (Kit) rice variety. A 1.8 kb rice NH3 cDNA was introduced into a Ubi-C1300-based binary vector. We were able to produce many (approximately 20) transgenic green calli and generated more than 10 transgenic rice seedlings. Upon transfer to greenhouse, most of these transgenic rice plants developed lesion mimics and dwarfism and eventually died. Only four plants eventually survived. These plants were challenged with Xoo pathogen PXO99 to test for possible effects on disease resistance. No obvious enhanced disease resistance was observed in these transgenic plants, as shown in FIG. 2A.

Enhanced Disease Resistance is Accomplished by Introduction of a Modified Copy of NH3

In the same attempt to study the function of NH3, we also created a binary construct based on the C1300 vector in which expression of the NH3 cDNA is directed by its own native promoter, contained in a one-kb DNA fragment. An N-terminal tag (NTAP:N-terminus tandem affinity purification) was added to the NH3 protein to potentially facilitate detection of the protein. This construct is designated nNT-NH3. When this construct was introduced into the Kit recipient, 12 transgenic plants were obtained and eventually survived. These plants were subject to challenge by Xoo. Our results (FIG. 2a) showed that about half (7 out of 12) of the T0 transgenic plants exhibit obvious enhanced resistance to Xoo.

Progeny segregation analysis was performed subsequently to test if the observed enhanced resistance phenotype is associated with the nNT-NH3 transgene. The presence of the nNT-NH3 transgene was detected by conducting polymerase-chain-reactions (PCR) targeting the NH3 minigene, which differs from the endogenous NH3 gene in lacking introns. Shown in FIG. 2*b* are progeny segregation analysis results of such three (lines #3A, 6A, and 13A) transgenic lines. The results clearly show that all progeny plants containing the nNT-NH3 gene (closed bars in FIG. 2*b*) are resistant to PXO99. On the contrary, null segregants (open bars), which no longer contain the transgene, are as susceptible to PXO99 as the wild type control Kit plants.

A more detailed analysis of the progeny of lines #6A and 13A was conducted to study the resistance phenotype. Progeny plants were genotyped for the presence of the nNT-NH3 gene. Those that contained the gene (both homozygous and heterozygous) were pooled together to represent lines #6A (labeled NH3-6) and #13A (labeled NH3-13), respectively. FIG. 3*a* shows the lesion development and 3*b* the growth curves of Xoo. Consistent with previous results, FIG. 3*a* shows that NH3-6 and NH3-13 plants clearly developed much shorter lesions compared with the Kit control at day 8 and day 12. Bacterial growth curves in FIG. 3*b* also show clear differences between the NH3-6 and NH3-13 transgenic plants and the Kit control at day 8 and day 12. The bacterial populations in Kit are more than 10 fold higher than those in the transgenic plants. T-tests on NH3-6 vs Kit and NH3-13 vs Kit at day 12 yield p values=0.0036 and 0.0042, respectively, indicating that the differences are highly statistically significant. Two typical leaves (12 days after Xoo inoculation) from each line and the Kit control are shown in FIG. 3*c*. An RT-PCR was conducted to confirm that transgenic lines NH3-6 and NH3-13 express the nNT-NH3 gene. RT-PCR results shown in FIG. 3*d* reveal that the NH3 transcript level is higher in both NH3-6 and NH3-13 (including both native NH3 and NTAP-NH3 transcripts) than in Kit (by approximately 3-fold) and that the NTAP-tagged NH3 is expressed only in the transgenic plants. These results clearly demonstrate that introduction of the nNT-NH3 transgene into wild type rice enhances resistance to the Xoo pathogen.

NH3 Transgenic Plants Show Strong Responses to Plant Defense Activators

We have previously reported that application of BTH to the Ubi-NH1 transgenic plants induces/enhances lesion mimic development (Chern et al., 2005). We tested if the nNT-NH3 transgenic plants would have a similar response to BTH treatment. To our surprise, when sprayed with 10 mM BTH, the nNT-NH3 plants responded to BTH very strongly, leading to extremely severe cell death. As shown in FIG. 4*a*, the severity of the cell death induced by BTH treatment is extremely high, as evidenced by the dry-out of whole leaves within 3-4 days. On the contrary, plants that carry an NTAP control driven by the Ubi-1 promoter (Park et al., 2008) are completely clear of such cell death phenotype. These results suggest that the development of the severe cell death phenotype after BTH application is due to the NH3 transgene.

We then treated the nNT-NH3 plants as well as the Kit control with 1 mM BTH or 1 mM INA to test for effects. When treated with 1 mM BTH, the nNT-NH3 plants developed lesion mimic spots in general together with some leaves showing bleached areas, representing severe cell death, as shown by the two representative leaves in FIG. 4*b* (labeled NH3, BTH). In contrast, when treated with 1 mM BTH, Kit developed no lesion mimic spots at all and was free of bleached areas (see Kit, BTH). Mock nNT-NH3 plants treated with no BTH only occasionally carry some small lesion mimic spots (NH3, mock). When treated with 1 mM INA, the nNT-NH3 plants developed typical lesion-mimic spots, but no bleached areas on leaves (NH3, INA). Treatment with 1 mM INA had little effects on Kit plants (Kit, INA). These results suggest that the nNT-NH3 plants respond to plant defense activators, such as BTH and INA, with clearly elevated sensitivity.

Defense-Related Genes are Induced More Strongly in the NH3 Transgenic Plants

To investigate the BTH- and INA-induced responses at the molecular level, we looked at the transcript expression levels of several rice defense-related genes, including PR1a, PR3, PR10, POX (peroxidase), and NH1. RT-PCR results of these genes for response to BTH treatment are shown in FIG. 5*a* and real-time quantitative PCR results in FIG. 5*b*. The input cDNA amounts were equalized first by using actin as the reference in FIG. 5*a*. Quantitative expression data in FIG. 5*b* are expressed as fold of actin gene expression. As expected, the NH3 levels in the nNT-NH3 plants (filled bar) are elevated by about 3- to 4-fold compared to Kit (open bar) control before treatment. Interestingly, in Kit control plants (open bars), the NH3 transcript levels appear slightly reduced after BTH application, especially at day 4 and day 8. In nNT-NH3 plants, the NH3 levels appear further modestly induced at day 1, but otherwise remain constantly elevated compared to Kit after BTH treatment. Mock treatment appears also has effects on the NH3 levels. In Kit controls, NH1 levels remain relatively constant, except at day 4 and day 8 where the NH1 levels appear slightly reduced. Interestingly in untreated nNT-NH3 plants, the NH1 level is reduced by half compared to Kit and is induced by about 3.5-fold (2-fold compared to untreated Kit) one day after BTH treatment; the NH1 levels then remain at levels compatible to that of untreated Kit control, except at day 8, where it is significantly higher.

Results in FIGS. 5*a* and 5*b* show that expression of defense gene PR1a is at comparable levels in Kit and in nNT-NH3 plants before treatment, both at very low levels. Upon 1 mM BTH treatment, PR1a expression is induced up to 11-fold in Kit. PR1a is induced dramatically more by BTH (up to 244-fold) in the nNT-NH3 plants than in Kit. The PR3 expression level in nNT-NH3 plants is about two fold that in Kit. PR3 expression is slightly (up to 2-fold) induced by BTH in Kit, but strongly induced (up to 10-fold) by BTH in nNT-NH3 plants. The PR10 level in nNT-NH3 plants is lower than in Kit. Similarly, expression of PR10 is slightly induced (up to 2-fold) in Kit but strongly induced (up to 51-fold over untreated nNT-NH3 or 12-fold over untreated Kit) in nNT-NH3 plants. Expression levels of peroxidase genes POX8.1 and POX22.3 in nNT-NH3 are comparable to those in Kit. BTH treatment significantly induces POX8.1 and POX22.3 expression in both Kit and nNT-NH3 plants, but more strongly for POX22.3 in nNT-NH3 plants. However, BTH treatment results in a faster drop in the POX8.1 expression level, leading to a lower level of POX8.1 in nNT-NH3 than in Kit at day 4.

Figure 5A:
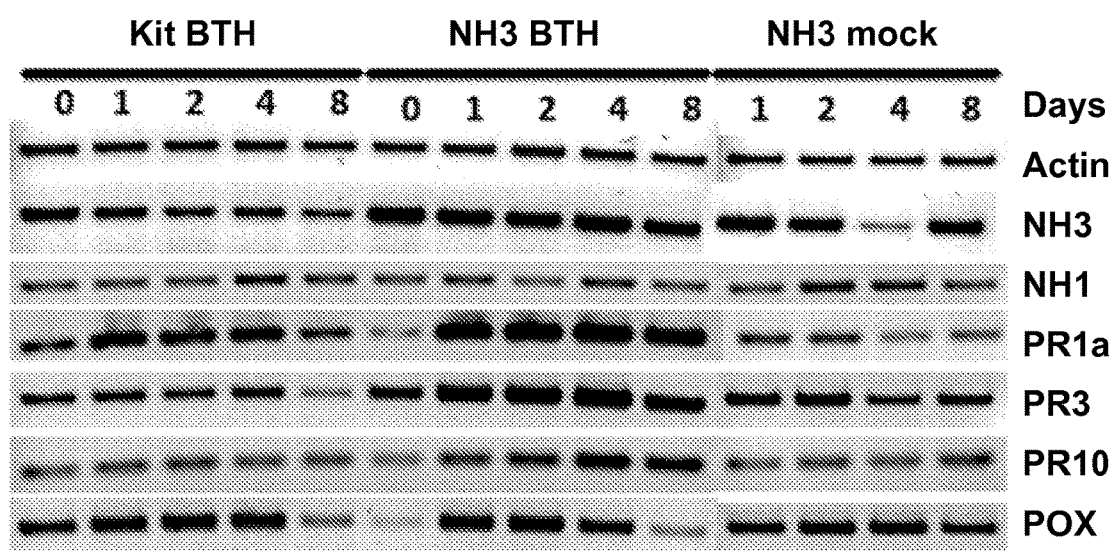
FIG. 5. Effects of introduction of nNT-NH3 on expression of defense-related genes. A. Effects of nNT-NH3 on induction by BTH treatment. Kit control and nNT-NH3 plants were foliar sprayed with 1 mM BTH or with mock solution. Leaf samples were collected at days 0, 1, 2, 4, and 8. Total RNA was extracted and equal amount of RNA was used to synthesize cDNA for RT-PCR. The amounts of cDNA input were further equalized using actin as the reference. The same amount of cDNA was then used in the RT-PCR reactions for NH3 and defense-related genes: NH1, PR1a, PR3, PR10 and peroxidase (POX22.3). B. Quantitative real time RT-PCR. Real time qPCR experiments were performed using the cDNA prepared in A. Open bars represent Kit treated with 1 mM BTH; filled bars represent nNT-NH3 treated with 1 mM BTH; gray bars represent nNT-NH3 with mock treatment. Days after BTH application are depicted under each panel. The targeted gene is indicated in each panel. The numbers on the X-axis in each graph represent the expression levels normalized to actin expression. Each bar represents three technical replications and its standard deviation. C. Effects of nNT-NH3 on induction by INA. Kit control and nNT-NH3 plants were treated with 1 mM INA or mock solution. Leaf samples were collected at days 0, 1, 2, 4, and 8. Total RNA samples were extracted. The amounts of cDNA input were equalized using actin as the reference. RT-PCR reactions were performed for genes NH3, PR1a, PR3, PR10, and peroxidase (POX22.3).
Figure 5B:
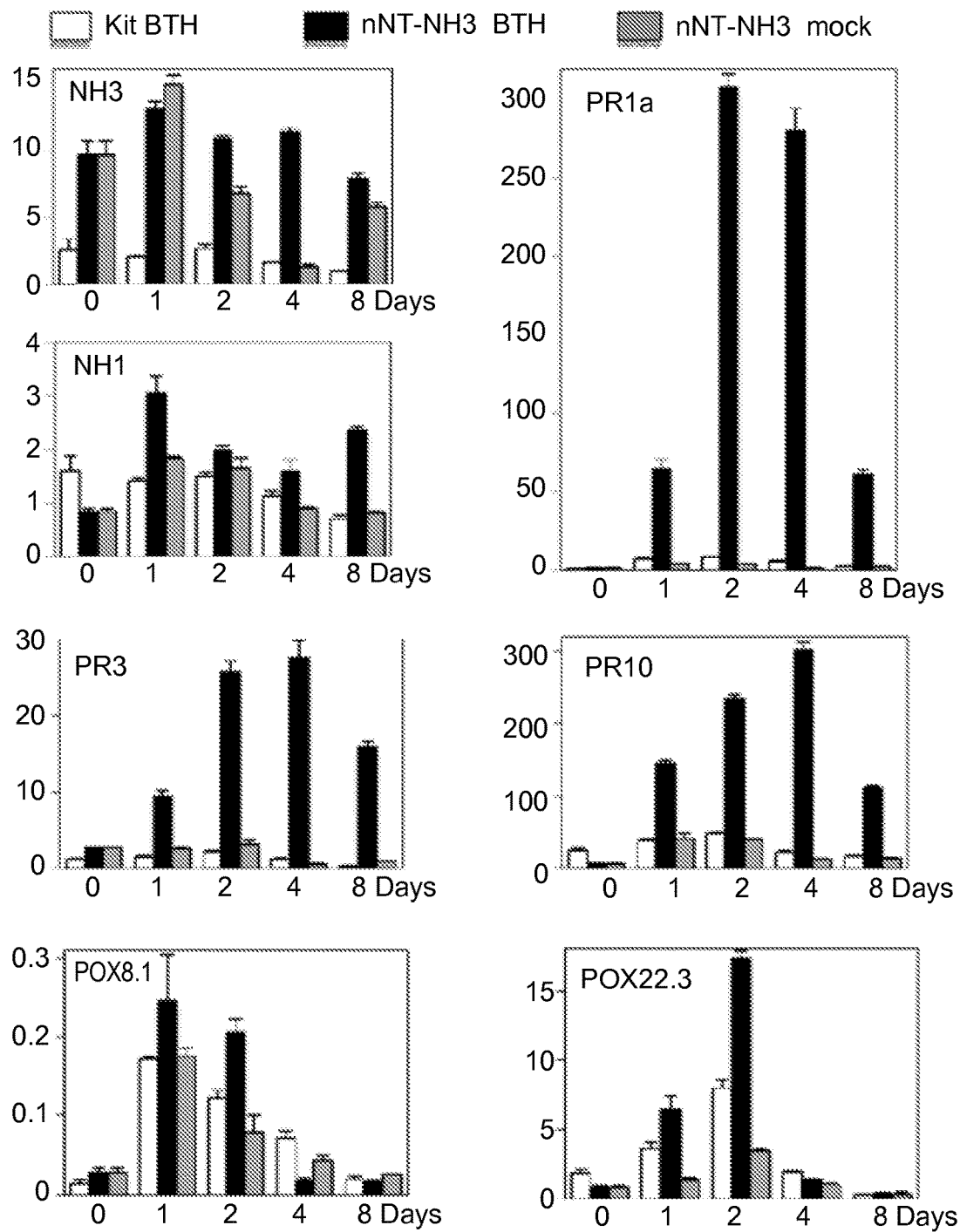
Figure 5C:
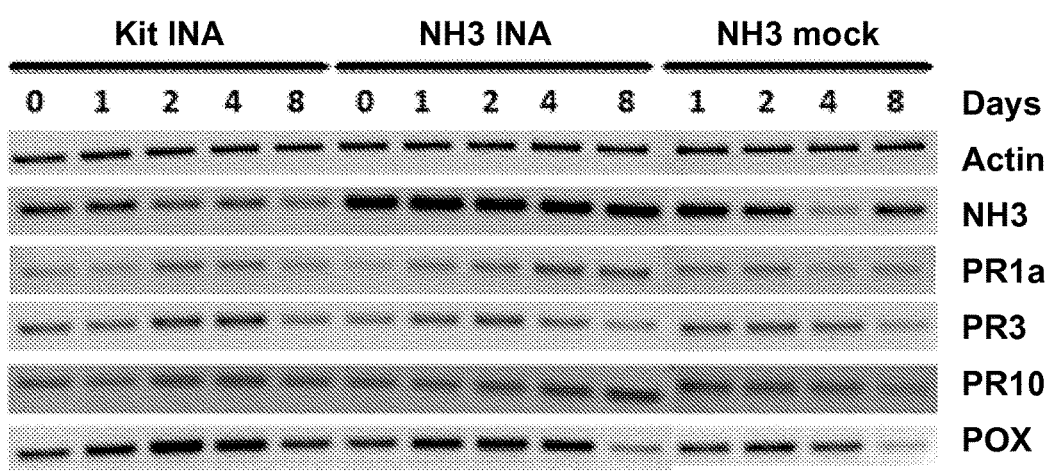

Results in FIG. 5c show that 1 mM INA treatment also slightly reduces the levels of NH3 expression. However, the NH3 levels in the nNT-NH3 plants remain constantly elevated. Treatment with INA slightly induces expression of PR1a, PR3, and PR10 in Kit plants. The elevated levels of NH3 have no obvious effects on induction of these genes by INA. INA also induces expression of POX in Kit and nNT-NH3 plants. The elevated levels of NH3 appear to have similar but mild effects on peroxidase gene expression.

These results suggest that elevated NH3 levels, in general, enhance induction of defense-related genes, but may have the opposite effect on some other genes, such as peroxidases, at certain stages. Nevertheless, these results support the observation that higher levels of NH3 transcript enhance responses to BTH treatment, which induces PR gene expression and disease resistance. More importantly, even at these higher levels of NH3 transcript, the defense-related genes are not highly induced without inducer treatment.

The Enhanced Disease Resistance Phenotype is Due to the NH3 protein itself

Figure 4:
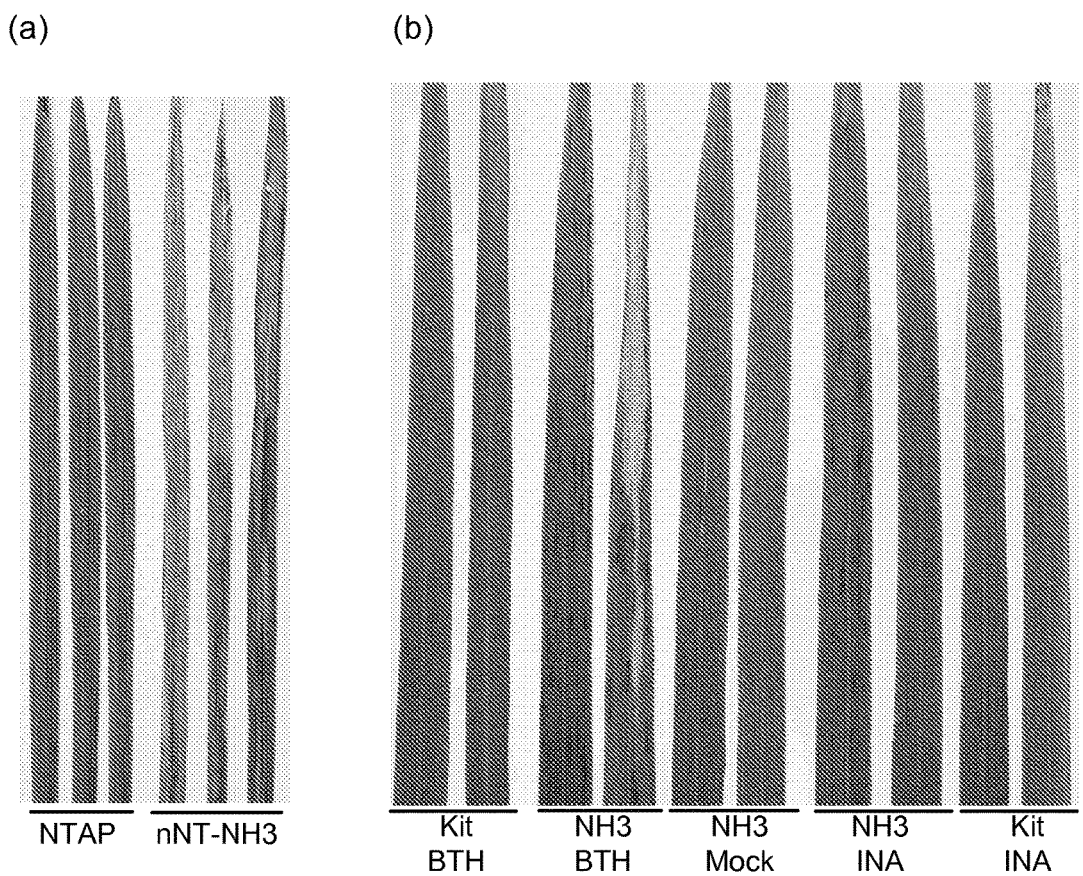
FIG. 4. Responses of nNT-NH3 plants to plant defense activators. A. Responses to 10 mM BTH. nNT-NH3 and NTAP control plants were foliar sprayed with 10 mM BTH. Three representative leaves each from the NTAP control and nNT-NH3 plants one week after the treatment. B. Responses to 1 mM BTH and INA. Plants were foliar sprayed with either 1 mM BTH, 1 mM INA, or mock solution. Two typical leaves from each combination of plant and treatment are shown. Symptoms on leaves were allowed to develop for one week following the treatment.
Figure 6:
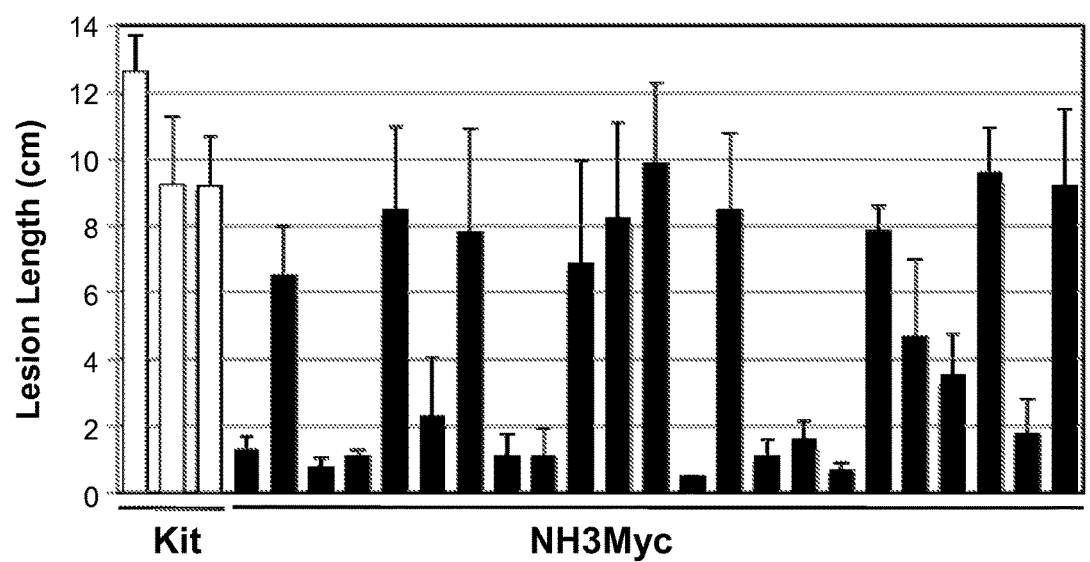
FIG. 6. Lesion length measurement of NH3 Myc transgenic plants. Three Kit control (open bars) and 23 independent NH3Myc (filled bars) T0 transgenic plants were inoculated with PXO99 and lesion length measured two weeks post inoculation. On average four leaves were measured for each plant. The error bars represent standard deviations.

There are no reports so far describing possible involvement of rice NH3 in plant defense or any function of NH3. The enhanced disease resistance effects and elevated responses to BTH and INA, conferred by the nNT-NH3 plants, are most likely due to the function of the NH3 protein itself because control transgenic plants expressing the NTAP tag alone show no such effects (see FIG. 4a above; Park et al., 2008). However, the possibility remains that introducing the NTAP tag to the N-terminus of the NH3 protein may cause the protein to function differently, leading to the observed phenotypes. To rule out this possibility, we created another modified NH3 construct, NH3Myc, which would produce an NH3 protein fused to the c-Myc tag at the C-terminus and its expression driven by the same 1 kb NH3 promoter. We transformed Kit with this construct and generated more than 20 T0 transgenic plants. These plants were challenged with PXO99 along with Kit as control. Approximately half of the NH3Myc transgenic plants show high levels of enhanced resistance to Xoo challenge, as shown in FIG. 6, similar to the case of nNT-NH3 transgenic plants. These results show that the NH3Myc construct has the same function as the nNT-NH3 construct. Because the NH3Myc protein carries a tag different from the TAP tag at a totally different location, these results suggest that the observed effects are from the function of the NH3 protein itself.

Discussion

Despite numerous studies using NPR1 or its orthologs to achieve enhanced disease resistance in many plant species (Cao et al., 1998; Friedrich et al., 2001; Chern et al., 2001; Lin et al., 2004; Chern et al., 2005a; Le et al., 2009), for application purposes, no NPR1 paralogous genes have been shown to be able to enhance disease resistance until now. In Arabidopsis, BOP1 (NPR6) and BOP2 (NPR5) were shown to regulate leaf development. Both Arabidopsis and the rice NPR1-like proteins form three groups, with BOP1 and BOP2 being the most distant members from NPR1. Thus, this group of NPR1-like proteins may function to regulate leaf development rather than defense. In support of this hypothesis, we have shown that increased expression of rice NH4 or NH5, using either their native promoters or the maize Ubi-1 promoter, do not confer enhanced resistance in transgenic plants (M. S. Chern and P. Ronald, unpublished). These observations are consistent with Arabidopsis results supporting the notion that this group of NPR1-like proteins may not be involved in regulating the plant defense response.

Liu et al. (2005) reported that Arabidopsis NPR4 is required for basal resistance to Pseudomonas syringae pv. tomato (Pst) DC3000 and Erysiphe cichoracearum because they observed that the npr4-1 mutant is more susceptible to these two pathogens. However, Zhang et al. (2006) reported that Arabidopsis NPR3 and NPR4 are negative regulators of PR gene expression and disease resistance. Zhang et al. showed that npr3 mutants have slightly increased basal PR-1 expression and the npr3npr4 double mutant shows higher PR-1, PR-2, and PR-5 expression. The double mutant plants display enhanced resistance against virulent bacteria, such as Pst DC3000, and oomycete pathogens (Zhang et al., 2006). The conclusions of these two reports contradict each other. Moreover, other than NPR1 itself, no Arabidopsis NPR1-like genes have been shown to enhance disease resistance when expressed at higher levels.

Yuan et al. (2007) showed that overexpression of OsNPR2 and OsNPR3 in rice had no significant effects on resistance to Xoo. Thus, whether any of the rice NPR1 paralogs is similarly involved in regulating defense responses was in serious doubt. We tried to overexpress NH3 in the Kit rice variety by using the maize Ubi-1 promoter, which has been successfully used in many cases to overexpress a gene in rice (Chern et al., 2001; Chern et al., 2005a; Chern et al., 2005b). We failed to obtain plants carrying enhanced resistance. Instead, most of the transgenic plants died before or after transfer to greenhouse. Presumably ultra high levels of NH3 expression, as driven by the Ubi-1 promoter (whose expression often reaches 10-fold or higher than the endogenous gene), cause toxicity leading to lethality. A similar situation may have occurred in Yuan's overexpression experiment with the OsNPR3 gene when they used the Ubi-1 promoter.

When we used the NH3 native promoter to drive the expression, many of the transgenic plants exhibited enhanced resistance. These native promoter NH3 transgenic plants survived, most likely because they do not express extremely high levels of NH3, but only moderate levels (about 3- to 4-fold higher than the endogenous level) sufficient to enhance resistance. In addition, the native promoter NH3 constructs may express NH3 only in relevant tissues at the right developmental stages and the right timing, minimizing possible detrimental effects. This is supported by the observation that expression of PR genes in nNT-NH3 plants is not highly elevated until induction by BTH (FIGS. 5a and 5b). However, once it is triggered by BTH, PR1a induction reaches as high as 244-fold in the nNT-NH3 plants whereas induction by BTH reaches 11-fold in Kit plants. Thus, the NH3 transgene has little effects before BTH induction but magnifies the BTH effect by 20-fold. Practically, this likely means that less BTH is needed to induce same levels of defense response. In contrast, rice transgenic plants carrying the Ubi-NH1 transgene, which exhibit normal developmental phenotypes, show elevated levels of PR gene expression without induction (Chern et al., 2005). Thus, the use of native promoter to express an extra copy of NH3 clearly carries advantages. In Arabidopsis, the NPR1 transcript level is elevated only two to three-fold after induction (Cao et al., 1997). These levels of NPR1 transcript are high enough to enhance disease resistance significantly. In the results presented here, introduction of an extra copy of NH3 is able to achieve similar levels (3- to 4-fold) of NH3 transcript, leading to enhanced disease resistance. Similarly, we have also used the same strategy to introduce an extra copy of NH1 into Kit rice and observed enhanced resistance (Chern and Ronald, unpublished). Therefore, this strategy may be widely applicable when using regulatory genes, such as NH3 and NH1, to engineer plants with enhanced disease resistance and other desirable traits.

The dramatic cell death responses of the nNT-NH3 plants to BTH are striking. At 1 mM of BTH, these plants start to show bleached areas on leaves, a symptom of severe cell death and strongly activated defense response. At 10 mM of BTH, treated leaves are bleached and dried out completely. These symptoms are more severe than those observed on NH1 over-expression plants treated with the same concentrations of BTH. Thus, NH3 may respond to BTH more dramatically than NH1 in certain ways. Additional molecular characterization is needed to reveal the mechanism leading to the difference in response to BTH.

It is interesting to notice that while the NH1 transcript level is lower in nNT-NH3 than in Kit plants without induction, it is induced to a level twice as high as that in Kit plants one day after BTH treatment (FIG. 5b). In contrast, in Kit plants after application of 1 mM BTH, NH1 expression levels are relatively unchanged. These data suggest that the levels of NH1 and NH3 expression may be highly coordinated in order to maintain a cellular homeostatic state. In support of this notion, our microarray results show that, in the NH1 over-expression plants, NH3 expression is up-regulated by 1.6 fold (unpublished). This data is consistent with the idea that NH3 is involved in plant defense responses. Also in support of a positive role for NH3 in plant defense response is that our microarray data on NRR over-expressing (NRRox) plants show a 2.4 fold down-regulation of NH3 expression (unpublished). NRRox plants exhibit super-susceptibility, evidenced by long lesions and few HR-like spots following Xoo challenge (Chern et al., 2005b). Down-regulation of NH3 expression in NRRox plants may contribute to the super-susceptible phenotype.

Experimental Procedures

Plant Materials, Growth Conditions, and Pathogen Challenge

The Kitaake (Kit) japonica rice (*Oryza sativa* L) cultivar was used for this study. Kit rice is susceptible to the Philippine Xoo strain PXO99AZ. Rice plants were grown in green houses at UC Davis at 27-32° C. under sunlight. For Xoo inoculation, 5-6 weeks old plants were transferred to a growth chamber and inoculated with PXO99AZ by the scissor-dip method (Kauffman et al., 1973). Xoo growth curve measurements were conducted as described before (Chern et al., 2005b). Growth chambers were set at the same temperatures with a day/night time cycle of 14 h/10 h.

Gene Isolation and Plasmid Construction

NH3 cDNA was amplified from a Nipponbare rice cDNA pool with primers NH3TAP1 (5'CACCGAGACGTCCAC-CATAAGCTTCTC3; SEQ ID NO:20) and NH3TAP3 (5'ACTGCAGATTAGACTTAACTGCTG3; SEQ ID NO:21). The NH3 cDNA PCR product was cloned into the pENTR-D vector and confirmed by sequencing. The one-kb NH3 promoter was amplified with primers NH3P-1 (5'TTT-TAAGCTTCGTTGGATGAACTACATTGCTGAT3'; SEQ ID NO:22) and NH3P-2 (5'TTGGATCCAGATCTTATC-CGGAAATTTCGCGCGTGT3; SEQ ID NO:23) and cloned into pBluescript II SK—using HindIII+BamHI. The insert was sequence-confirmed. The NH3 cDNA was cloned into the Gateway-compatible Ubi-NTAP-1300 vector (Rohila et al., 2006) by LR recombination to generate the Ubi-NT-NH3 over-expression construct. To create a native promoter NH3 construct, the NH3 promoter was first cloned into the Ubi-NTAP-1300 vector using HindIII+BglII to replace the Ubi-1 promoter. The resultant plasmid was used to accommodate the NH3 cDNA by recombination, yielding the nNT-NH3 construct.

For the NH3-Myc construction, the same one-kb NH3 promoter fragment (NH3P1.0) was amplified with primers NH3P-3 (5'CACCTCGTTGGATGAACTACATTGCT-GAT3; SEQ ID NO:24) and NH3P-NcoI (5'TCCATG-GCTCTTATCCGGAAATTTCGCGCGTGT3; SEQ ID NO:25) and cloned into the pENTR-D vector. The NH3 cDNA was re-amplified sequentially, first with primers NH3ATG (5'CACCATGGAGACGTCCACCATAAG3; SEQ ID NO:26) and NH3-cMyc (5'GGAGATGAGCTTCT-GCTCCCGTGATAGCTTCCCTTTCTTG3'; SEQ ID NO:27), then with primers NH3ATG and cMyc-SpeI (5'ACTAGTTATTTCTCCAACAGGTCTTCCTCGGA-GATGAGCTTCTGCTC3'; SEQ ID NO:28). The NH3Myc PCR product was cloned into the pENTR-D vector and confirmed by sequencing. The NH3P1.0 fragment was excised with NotI+NcoI and cloned into the NH3Myc/pENTR plasmid, pre-digested with NcoI+NotI, generating the P1-NH3Myc/pENTR construct. This construct was used to transfer the P1-NH3Myc fragment into a Gateway-C1300 vector by recombination, creating P1-NH3Myc/C1300. The P1-NH3Myc construct was used to transform Kit rice, generating NH3Myc transgenic plants.

Treatment with Plant Defense Activators

For 10 mM BTH treatment, the commercial product Actigard (Syngenta) was first used for foliar spray on the rice plants. Pure BTH chemical Acibenzolar-5-methyl (Wako) was subsequently used in place of Actigard. One mM of BTH and INA solutions were prepared in 0.05% Tween 20 for foliar spray.

RNA Extraction and RT-PCR

Leaf samples were collected and frozen immediately in liquid nitrogen. Leaf samples were stored at −80° C. until use. Total RNA was extracted using the Trizol reagent (Sigma) according to the manufacturer's instruction. RNA was reverse-transcribed using reverse transcriptase Superscript (Invitrogen). Approximately 10 μg of RNA was used for each reverse transcription. RT-PCR was first performed with primers targeting an actin gene as the reference. An equal amount of cDNA input was then used for RT-PCR for NH3 or defense-related genes. RT-PCR for NH3 used primers NH3-RT1 (5'GTGCATTGGCGTCTTACAGCA3'; SEQ ID NO:29) and NH3-RT2 (5'GGGAAGTATCGTCGTC-CGAGT3; SEQ ID NO:30). RT-PCR for NTAP-NH3 used primers NH3-2 (5'GTGGCTGCAGCCGTCGTCCA3; SEQ ID NO:31) and NTAP-5 (5'ATGCCCAAGC-CCCAAAGGACTACG3; SEQ ID NO:32). RT-PCR for NH1 used primers NH1-RT1 (5'ACTTAGCTCGGAT-GACGGCAC3; SEQ ID NO:33) and NH1-TAP2 (5'AG-CAATGGTGTTCATCTCCTTGGT3; SEQ ID NO:34). Genes PR1a (Os07g03710) and PR10 (Os12g36830) as markers for plants defense have been described before (Park et al., 2008).

Quantitative real time PCR were performed on a Bio-Rad CFX96 Real-Time System coupled to a C1000 Thermal Cycler (Bio-Rad). For qPCR reactions, the Bio-Rad SsoFast EvaGreen Supermix was used. QPCR primers used are as follows: Actin-Q1 (TCGGCTCTGAATGTACCTCCTA; SEQ ID NO:35) and Actin-Q2 (CACTTGAGTAAAGACT-GTCACTTG; SEQ ID NO:36) for actin gene; NH1-RT3 (CTGATCCGTTTCCCTCGGA; SEQ ID NO:37) and NH1-RT4 (GACCTGTCATTCTCCTCCTTG; SEQ ID NO:38) for the NH1 gene; NH3-RT3 (TGCTACACCTCTGCTG-GTTGA; SEQ ID NO:39) and NH3-RT4 (GACCAG-CAAACTCTTGAGTTGAG; SEQ ID NO:40) for the NH3 gene; PR3-1 (CTTGGACTGCTACAACCAGA; SEQ ID NO:41) and PR3-2 (CATTGTGGGCATTACTGATG; SEQ ID NO:42) for the PR3 gene; POX8.1-1 (CAAACTGGA-TACAAAAGCAAACAC; SEQ ID NO:43) and POX8.1-2 (CATGGGCTTCCTGATCTG; SEQ ID NO:44) for the POX8.1 gene; and POX22.3-1 (ATCGTGTCGACGACGA-CAT; SEQ ID NO:45) and POX22.3-2 (CTCTGCTCCATA-CACTTGATG; SEQ ID NO:46) for the POX22.3 gene. QPCR reactions were run at 56° C. annealing for 12 sec and 95° C. for 8 sec for 40 cycles.

REFERENCES

Boyle, P., Su, E. L., Rochon, A., Shearer, H. L., Murmu., J. Chu, J. Y., Fobert, P. R., and Despres, C. (2009) The BTB/POZ domain of the *Arabidopsis* disease resistance protein NPR1 interacts with the repression domain of TGA2 to negate its function. *Plant Cell* 21, 3700-3713.

Cao, H., Bowling, S. A., Gordon, A. S., and Dong, X. (1994). Characterization of an *Arabidopsis* mutant that is nonresponsive to inducers of systemic acquired resistance. *Plant Cell* 6, 1583-1592.

Cao, H., Glazebrook, J., Clarke, J., Volko, S., and Dong, X. (1997). The *Arabidopsis* npr1 gene that controls systemic acquired resistance encodes a novel protein containing ankyrin repeats. *Cell* 88, 57-63.

Cao, H., Li, X., and Dong, X. (1998). Generation of broad-spectrum disease resistance by overexpression of an essential regulatory gene in systemic acquired resistance. *Proc. Natl. Acad. Sci.* 95, 6531-6536.

Chern, M.-S., Fitzgerald, H. A., Yadav, R. C., Canlas, P. E., Dong, X., and Ronald, P. C. (2001). Evidence for a disease-resistance pathway in rice similar to the NPR1-mediated signaling pathway in *Arabidopsis*. *Plant J.* 27, 101-113.

Chern, M., Fitzgerald, H. A., Canlas, P. E., Navarre, D. A., and Ronald, P. C. (2005a). Over-expression of a rice NPR1 homolog leads to constitutive activation of defense response and hypersensitivity to light. *Mol. Plant. Microbe Interact.* 18, 511-520.

Chern, M., Canlas, P. E., Fitzgerald, H. A., Ronald, P. C. (2005b). Rice NRR, a Negative Regulator of Disease Resistance, Interacts with *Arabidopsis* NPR1 and Rice NH1. *Plant J.* 43, 623-635.

Delaney, T. P., Friedrich, L., and Ryals, J. A. (1995). *Arabidopsis* signal transduction mutant defective in chemically and biologically induced disease resistance. *Proc. Natl. Acad. Sci.* 92, 6602-6606.

Despres, C., DeLong, C., Glaze., S., Liu, E., and Fobert, P. R. (2000) The *Arabidopsis* NPR1/NIM1 protein enhances the DNA binding activity of subgroup of the TGA family og bZIP transcription factors. *Plant Cell* 12, 279-290.

Durrant, W. E. and Dong, X. (2004) Systemic acquired resistance. *Annu. Rev. Phytopathol.* 42, 185-209.

Friedrich, L., Lawton, K., Ruess, W., Masner, P, Speckner, N., Gt Rella, M., Meier, B., Dinher, S., Staub, T., Uknes, S., Metraux, J.-P., Kessman, H., and Ryals, J. (1996). A benzothiadazole derivative induces systemic acquired resistance in tobacco. *Plant J.* 9, 61-70.

Friedrich, L., Lawton, K., Dietrich, R., Willitis, M., Cade, R., and Ryals, J. (2001). NIM1 overexpression in *Arabidopsis* potentiates plant disease resistance and results in enhanced effectiveness of fungicides. *Mol. Plant-Microbe Intercact.* 9, 1114-1124.

Glazebrook, J., Rogers, E. E., and Ausubel, F. M. (1996). Isolation of *Arabidopsis* mutants with enhanced disease susceptibility by direct screening. *Genetics* 143, 973-982.

Gorlach, J., Volrath, S., Knauf-Beiter, G., Hengy, G., Beckhove, U., Kogel, K.-H., Oostendorp, M., Staub, T., Ward, E., Kessmann, H., and Ryals, J. (1996). Benzothiadiazole, a novel class of inducers of systemic acquired resistance, activates gene expression and disease resistance in wheat. *Plant Cell* 8, 629-643.

Jacquemin, J., Laudie, M., and Cooke, R. (2009) A recent duplication revisited: phylogenetic analysis reveals an ancestral duplication highly-conserved throughout the *Oryza* genus and beyond. *BMC Plant Biol.* 9, 146.

Jun, J. H., Ha, C. M., and Fletcher, J. C. (2010) BLADE-ON-PETIOLE1 coordinates organ determinacy and axial polarity in *Arabidopsis* by directly activating asymmetric leaves2. *Plant Cell* 22, 62-76.

Kauffman, H. E., Reddy, A. P. K., Hsieh, S. P. V., and Marca, S. D. (1973) An improved technique for evaluation of resistance of rice varieties to *Xanthomonas oryzae*. *Plant Dis. Rep.* 57, 537-541.

Kinkema, M., Fan, W., and Dong, X. (2000) Nuclear localization of NPR1 is required for activation of PR gene expression. *Plant Cell* 12: 2339-2350.

Le Henanff, G., Heitz, T., Mestre, P., Mutterer, J., Walter, B., and Chong, J. (2009) Characterization of *Vitis vinifera* NPR1 homologs involved in the regulation of pathogenesis-related gene expression. *BMC Plant Biol.* 9, 54.

Lin, W. C., Lu, C. F., Wu, J. W., Cheng, M. L., Lin, Y. M., Yang, N. S., Black, L., Green, S. K., Wang, J. F., and Cheng, C. P. (2004) Transgenic tomato plants expressing the *Arabidopsis* NPR1 gene display enhanced resistance to a spectrum of fungal and bacterial diseases. Transgenic Res. 13, 567-581.

Liu, G., Holub, E. B., Alonso, J. M., Ecker, J. R., and Fobert, P. R. (2005) An *Arabidopsis* NPR1-like gene, NPR4, is required for disease resistance. *Plant J.* 41, 304-318.

Meur, G., Budatha, M., Srinivasan, T., Rajesh Kumar, K. R., Dutta Gupta, A., and Kirti, P. B. (2008) Constitutive expression of *Arabidopsis* NPR1 confers enhanced resistance to the early instars of *Spodoptera litura* in transgenic tobacco. Physio. Plant 133, 765-775.

Morris, S. W., Vernoolij, B., Titatarn, S., Starrett, M., Thomas, S., Wiltse, C. C., Frederiksen, R. A., Bhandhufalck, A., Hulbert, S., and Uknes, S. (1998) Induced resistance responses in maize. *Mol. Plant-Microbe Interact.* 11, 643-658.

Mou, Z., Fan, W., and Dong, X. (2003). Inducers of plant systemic acquired resistance regulate NPR1 function through redox changes. *Cell* 113, 1-10.

Park, C.-J., Peng, Y., Chen, X., Dardick, C., Ruan, D., Bart, R., Canlas, P. E., Pamela C. Ronald, P. C. (2008) Rice XB15, a Protein Phosphatase 2C, Negatively Regulates Cell Death and XA21-Mediated Innate Immunity. *PLoS Biology*, 6(9) e231.

Rohila, J. S., Chen, M., Chen, S., Chen, J., Cerny, R. L., Dardick, C., Canlas, P. E, Xu, X., Gribskov, M., Kanrar, S., Zhu, J. K., Ronald, P., Fromme, M. E. (2006) Protein-protein interactions of tandem affinity purification-tagged protein kinases in rice. *Plant J.* 46, 1-13.

Rohilla, R., Singh, U. S., and Singh, R. L. (2002). Mode of action of acibenzolar-S-methyl against sheath blight of rice, caused by *Rhizoctonia solani* kuhn. *Pest Manag. Sci.* 58, 63-69.

Ryals, J., Weymann, K., Lawton, K., Friedrich, L., Ellis, D., Steiner, H.-Y., Johnson, J., Delaney, T. P., Jesse, T., Vos, P., and Uknes, S. (1997). The *Arabidopsis* NIM1 protein shows homology to the mammalian transcription factor inhibitor IκB. *Plant Cell* 9, 425-439.

Schweizer, P., Schlagenhauf, E., Schaffrath, U., and Dudler, R. (1999). Different patterns of host genes are induced in rice by *Pseudomonas syringae*, a biological inducer of resistance, and the chemical inducer benzothiadiazole (BTH). *Eur. J. Plant Pathol.* 105, 659-665.

Shah, J., Tsui., F., Klessig, D. F. (1997). Characterization of a salicylic acid-insensitive mutant (sai1) of *Arabidopsis thaliana*, identified in a selective screen utilizing the SA-inducible expression of the tms2 gene. *Mol. Plant. Microbe Interact.* 10, 69-78.

Shimono, M., Sugano, S., Nakayama, A., Jiang, C. J., Ono, K., Toki, S., and Takatsuji, H. (2007). Rice WRKY45 plays a crucial role in benzothiadiazole-inducible blast resistance. *Plant Cell* 19, 2064-2076.

Smith, J. A. and Metraux, J.-P. (1991). *Pseudomonas syringae* pathovar syringae induces systemic resistance to *pyricularia oryzae* in rice. *Physiol. and Mol. Plant. Pathol.* 39, 451-461.

Spoel, S. H., Koornneef, A., Claessens, S. M. C., Korzelius, J. P., Van Pelt, J. A. Mueller, M. J., Buchala, A. J., Metraux, J.-P., Brown, R., Kazan, K., Van Loon, L. C., Dong, X., and Pieterse, C. M. J. 2003. NPR1 modulates cross-talk between salicylate- and jasmonate-dependent defense pathways through a novel function in the cytosol. *Plant Cell* 15, 760-770.

Ward, E. R., Uknes, S. J., Williams, S. C., Dincher, S. S., Wiederhold, D. L., Alexader, D. C., Ahl-Goy, P., Metraux, J. P., and Ryals, J. A. (1991) Coordinate gene activity in response to agents that induce systemic acquired resistance. *Plant Cell* 10, 1085-1094.

Yoshioka, K., Nakashita, H., Klessig, D. F., and Yamaguchi, I. (2001) Probenazole induces systemic acquired resistance in *Arabidopsis* with a novel type of action. *Plant J.* 25, 149-157.

Yuan, Y., Zhong, S., Li, Q., Zhu, Z., Lou, Y., Wang, L., Wang, J., Wang, M., Li, Q., Yang, D., and He, Z. (2007). Functional analysis of rice NPR1-like genes reveals that OsNPR1/NH1 is the rice orthologue conferring disease resistance with enhanced herbivore susceptibility. *Plant Biotechnol. J.* 5, 313-324.

Zhang, Y., Cheng, Y. T., Qu, N., Zhao., Q., Bi, D., and Li, X. (2006) Negative regulation of defense response in *Arabidopsis* by two NPR1 paralogs. *Plant J.* 48, 647-656.

Zhang, Y., Fan., W., Kinkema, M., Li, X., and Dong, X. (1999) Interaction of NPR1 with basic leucine zipper protein transcription factors that bind sequences required for salicylic acid induction of the PR-1 gene. *Proc. Natl. Acad. Sci. USA* 96, 6523-6528.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A transgenic rice plant comprising a heterologous expression cassette, the expression cassette comprising a promoter operably linked to a polynucleotide encoding a polypeptide comprising a NPR1 homolog 3 (NH3) polypeptide, wherein the NH3 polypeptide is a polypeptide encoded by SEQ ID NO:1 and wherein the promoter comprises SEQ ID NO:3, wherein the plant expresses the NH3 polypeptide at a higher level than a plant lacking the expression cassette and wherein the plant has enhanced disease resistance compared to the plant lacking the expression cassette.

2. The plant of claim 1, wherein the polynucleotide is at least 70% identical SEQ ID NO:1.

3. The plant of claim 1, wherein the polynucleotide is at least 90% identical to SEQ ID NO:1.

4. The plant of claim 1, wherein the plant expresses the NH3 polypeptide at a level from about two-fold higher to about four-fold higher than the plant lacking the expression cassette.

5. A plant cell from the plant of claim 1, wherein the plant cell comprises the heterologous expression cassette.

6. A seed, flower, leaf, fruit, processed food, or food ingredient from the plant of claim 1, wherein the seed, flower, leaf, fruit, processed food, or food ingredient comprises the heterologous expression cassette.

7. A method of enhancing plant resistance to a pathogen, the method comprising:

introducing a nucleic acid comprising an expression cassette into one or more rice plants, wherein the expression cassette comprises a promoter operably linked to a polynucleotide encoding a NPR1 homolog 3 (NH3) polypeptide; wherein the NH3 polypeptide is a polypeptide encoded by SEQ ID NO:1 and wherein the promoter comprises SEQ ID NO:3, and from the one or more plants into which the nucleic acid comprising the expression cassette has been introduced, selecting a plant having increased resistance to a pathogen or pathogens as compared to the resistance of a plant lacking the expression cassette.

8. The method of claim 7, wherein the polynucleotide encoding the NH3 polypeptide has at least 70% sequence identity to SEQ ID NO:1.

9. The method of claim 8, wherein the polynucleotide encoding the NH3 polypeptide comprises SEQ ID NO:1.

10. The plant of claim 1, wherein the polynucleotide is at least 95% identical to SEQ ID NO:1.

11. The plant of claim 1, wherein the polynucleotide comprises SEQ ID NO:1.

* * * * *

SEQUENCE LISTING

```
<160> NUMBER OF SEQ ID NOS: 46

<210> SEQ ID NO 1
<211> LENGTH: 1799
<212> TYPE: DNA
<213> ORGANISM: Oryza sativa
<220> FEATURE:
<223> OTHER INFORMATION: rice Japonica Group cultivar Nipponbare
      non-expressor of pathogenesis-related genes 1
      (NPR1, NIM1, SAI1) homolog 3 (NH3, OsNPR3) cDNA,
      NPR1 paralog 3, BAC OSJNBa0056E06.6

<400> SEQUENCE: 1
ccatggagac gtccaccata agcttctcct cctcgtcgcc gccgtcccct ccgccgccgc    60
agccggctcc gggcgacatc gacgccgtca gcctcggccg cctcagcagg aacctcgaga   120
acctcctcga ccccgccttt ctcaactgcg ccgacgccga gatcgtcctc gcctccggag   180
gcggcgaccc cggcggcggc gccgtcgtgg gcgtccaccg ctgcatcctc gccgccagga   240
gccgcttctt ctacgaccac ttctcctccg ccccgcccc cgccccgcc accgccggcg    300 acaagccgca gctggacctc gacgggctgg tcccggcgg gcgccacatc ggccgagacg    360
ccctcgtcgc cgttctcagc tacctgtaca ccggccgcct caggtcggcg ccccccgagg   420
ccgccgcctg cctggacgac ggctgcagcc acgacgcgtg ccgcccggcg atcgacttcg   480
tcgtcgagtc cacgtacgcc gcctccggct tccagatctc cgagctcgtc tccctcttcc   540
agcgccgatt atctgatttt gtgaacaaag ctttggctga ggacatactg ccaattcttg   600
tggttgcctc cacctgccat cttccagagc tgctaaatca atgtatccag agggttgcca   660
```

```
actcgaacct ggacaatcgt tacctcgaga agcggcttcc ggatgatctg tacgccaagc    720
tgaaggagtt tcgcgtgcct gatgaaccac acagtggcat tcttgaccct gagcatgaga    780
agagggtcag aaacatccac aaggccttgg attccgatga tgtcgatctt gttggcatgc    840
ttctgaagga gtccccggtc accttggatg atgcattcgc catacactac gctgcggcct    900
actgtgagcc aaaagtgtta gcagaattgc tgaaactgga atctgcaaat gtgaacctga    960
agaactcaag tggatacacg ccgctccaca tggcttgcat gaggcgagaa ccggatatca   1020
ttgtttcgct tatagaaaag ggggcctctg ttctggaaag gacacaggat ggacgtgatg   1080
ctcttaccat ctgcaagaga ttaacaaggg agaaagaccg caacgagaaa tcagaaaaat   1140
gcaaggagag aagcaaggct tacttgtgca ttggcgtctt acagcaagaa ataaagagga   1200
gaccacaaat tttggaggac agatgtctg cagaggagtc aattgctaca cctctgctgg   1260
ttgataattt tcacatgagg ctactaaact tggagaatag agttgccttt gcaagaatat   1320
ttttcccttc ggaagccaaa cttgtgatgc gcatagcaca agctgactca actcaagagt   1380
ttgctggtct cacatctgct aatttcagta aacttaagga ggttgaccta aatgagaccc   1440
ccacaatgca aaacaggagg ttgcgagaac gccttgatgc tttgacaaaa acagttgaac   1500
tcggacgacg atacttccca cattgttcag aagttctcga caagttcctg aatgaagaat   1560
ccaccgattt gatcttgctt gaaagtggca cagcagagga ccagcaaacc aagaggatgc   1620
gcttttctga actcagagag gatgtacgga aggcctttac caaagataag gcagccggcg   1680
ctgcaatatc ttcctcaaca tctgcgtctt catcaccaag gtatgagaca agttaagac    1740
ctggcaacaa gaaagggaag ctatcacggt aatatcagca gttaagtcta atctgcagt    1799
```

<210> SEQ ID NO 2
<211> LENGTH: 583
<212> TYPE: PRT
<213> ORGANISM: Oryza sativa
<220> FEATURE:
<223> OTHER INFORMATION: rice Japonica Group cultivar Nipponbare
      non-expressor of pathogenesis-related genes 1
      (NPR1, NIM1, SAI1) homolog 3 (NH3, OsNPR3), NPR1
      paralog 3, BAC OSJNBa0056E06.6

<400> SEQUENCE: 2

```
Met Glu Thr Ser Thr Ile Ser Phe Ser Ser Ser Pro Ser Pro
 1               5                  10                  15

Pro Pro Pro Gln Pro Ala Pro Gly Asp Ile Asp Ala Val Ser Leu Gly
             20                  25                  30

Arg Leu Ser Arg Asn Leu Glu Asn Leu Leu Asp Pro Ala Phe Leu Asn
         35                  40                  45

Cys Ala Asp Ala Glu Ile Val Leu Ala Ser Gly Gly Gly Asp Pro Gly
     50                  55                  60

Gly Gly Ala Val Val Gly Val His Arg Cys Ile Leu Ala Ala Arg Ser
 65                  70                  75                  80

Arg Phe Phe Tyr Asp His Phe Ser Ser Ala Pro Ala Pro Ala Pro Ala
                 85                  90                  95

Thr Ala Gly Asp Lys Pro Gln Leu Asp Leu Asp Gly Leu Val Pro Gly
            100                 105                 110

Gly Arg His Ile Gly Arg Asp Ala Leu Val Ala Val Leu Ser Tyr Leu
        115                 120                 125

Tyr Thr Gly Arg Leu Arg Ser Ala Pro Pro Glu Ala Ala Ala Cys Leu
    130                 135                 140

Asp Asp Gly Cys Ser His Asp Ala Cys Arg Pro Ala Ile Asp Phe Val
```

-continued

```
            145                 150                 155                 160
        Val Glu Ser Thr Tyr Ala Ala Ser Gly Phe Gln Ile Ser Glu Leu Val
                            165                 170                 175

Ser Leu Phe Gln Arg Arg Leu Ser Asp Phe Val Asn Lys Ala Leu Ala
                            180                 185                 190

Glu Asp Ile Leu Pro Ile Leu Val Ala Ser Thr Cys His Leu Pro
                            195                 200                 205

Glu Leu Leu Asn Gln Cys Ile Gln Arg Val Ala Asn Ser Asn Leu Asp
                            210                 215                 220

Asn Arg Tyr Leu Glu Lys Arg Leu Pro Asp Asp Leu Tyr Ala Lys Leu
        225                 230                 235                 240

Lys Glu Phe Arg Val Pro Asp Glu Pro His Ser Gly Ile Leu Asp Pro
                            245                 250                 255

Glu His Glu Lys Arg Val Arg Asn Ile His Lys Ala Leu Asp Ser Asp
                            260                 265                 270

Asp Val Asp Leu Val Gly Met Leu Leu Lys Glu Ser Pro Val Thr Leu
                            275                 280                 285

Asp Asp Ala Phe Ala Ile His Tyr Ala Ala Tyr Cys Glu Pro Lys
                            290                 295                 300

Val Leu Ala Glu Leu Leu Lys Leu Glu Ser Ala Asn Val Asn Leu Lys
        305                 310                 315                 320

Asn Ser Ser Gly Tyr Thr Pro Leu His Met Ala Cys Met Arg Arg Glu
                            325                 330                 335

Pro Asp Ile Ile Val Ser Leu Ile Glu Lys Gly Ala Ser Val Leu Glu
                            340                 345                 350

Arg Thr Gln Asp Gly Arg Asp Ala Leu Thr Ile Cys Lys Arg Leu Thr
                            355                 360                 365

Arg Glu Lys Asp Arg Asn Glu Lys Ser Glu Lys Cys Lys Glu Arg Ser
                            370                 375                 380

Lys Ala Tyr Leu Cys Ile Gly Val Leu Gln Gln Glu Ile Lys Arg Arg
        385                 390                 395                 400

Pro Gln Ile Leu Glu Asp Gln Met Ser Ala Glu Glu Ser Ile Ala Thr
                            405                 410                 415

Pro Leu Leu Val Asp Asn Phe His Met Arg Leu Leu Asn Leu Glu Asn
                            420                 425                 430

Arg Val Ala Phe Ala Arg Ile Phe Phe Pro Ser Glu Ala Lys Leu Val
                            435                 440                 445

Met Arg Ile Ala Gln Ala Asp Ser Thr Gln Glu Phe Ala Gly Leu Thr
        450                 455                 460

Ser Ala Asn Phe Ser Lys Leu Lys Glu Val Asp Leu Asn Glu Thr Pro
        465                 470                 475                 480

Thr Met Gln Asn Arg Arg Leu Arg Glu Arg Leu Asp Ala Leu Thr Lys
                            485                 490                 495

Thr Val Glu Leu Gly Arg Arg Tyr Phe Pro His Cys Ser Glu Val Leu
                            500                 505                 510

Asp Lys Phe Leu Asn Glu Glu Ser Thr Asp Leu Ile Leu Leu Glu Ser
                            515                 520                 525

Gly Thr Ala Glu Asp Gln Gln Thr Lys Arg Met Arg Phe Ser Glu Leu
                            530                 535                 540

Arg Glu Asp Val Arg Lys Ala Phe Thr Lys Asp Lys Ala Ala Gly Ala
        545                 550                 555                 560

Ala Ile Ser Ser Ser Thr Ser Ala Ser Ser Pro Arg Arg Glu Arg
                            565                 570                 575
```

Arg Gly Arg Ser Arg Arg Ala
            580

<210> SEQ ID NO 3
<211> LENGTH: 1017
<212> TYPE: DNA
<213> ORGANISM: Oryza sativa
<220> FEATURE:
<221> NAME/KEY: promoter
<222> LOCATION: (1)...(1017)
<223> OTHER INFORMATION: rice Japonica Group cultivar Nipponbare
      non-expressor of pathogenesis-related genes 1
      (NPR1, NIM1, SAI1) homolog 3 (NH3, OsNPR) promoter

<400> SEQUENCE: 3

```
tcgttggatg aactacattg ctgatattga tcccaagaaa acaacttct ctaccaatat    60
tctcttccca accaatcaca accctccacc attcactttt tccacctacc tccactacac   120
atccaattac aaccctccac cactcatttc tacctacttt cttaataacc gtgtccaact   180
tcttatattt ttgggcggag gagtactata tttgttatgt tcatgcttca aagtacttac   240
aggcaatatt aatttttta tcatagaaaa atatatttt ttttataaat tgcacccttc    300
gttctatgaa aaactgacct tttgagatta atctacacaa gtattctttt agatttatct   360
ttaaaagtta tcttttattt cggggacgag tgagtaaaga tcaagtagta gtcctacaaa   420
ttctataaaa ttaaaaccac gtgttgcaaa aaaaaataga ataacgtaac tataatgtac   480
tttaagccat actcaagtgc ctaatcatgt tgtactgggt actattccta attcattcgg   540
ttttcgcttc ctttcgtact ggaggggagt atagtctttc acccagtaaa ttctccccca   600
cgacagctca ccctccaa agtcaagtca aggtcgtcgc ctcccacctc ctcctccgat    660
ccggccgccg cggaggcatg cgaccacacc actgtaccac tacaccacct cactgacacg   720
tgggccccac acgccacaca ccacaccagc agccagtcat cgatcgagtc ggcagcaatc   780
cccagcgcgc agaagaggag agagagagag tattcctcgc agaagagacg acgactcttc   840
cgccgacgac gtcacccccg tgacgtgggt tgccccgtca cggcctcgca tcaccacacc   900
tcaccacccc ccacgttctt gtttctttcc catccgcgta tagtagacca cggaggcagc   960
agagctgcag aggagtagcg agagaaaaat acacgcgcga aatttccgga taagagc    1017
```

<210> SEQ ID NO 4
<211> LENGTH: 598
<212> TYPE: PRT
<213> ORGANISM: Sorghum bicolor
<220> FEATURE:
<223> OTHER INFORMATION: sorghum cultivar BTx623 hypothetical protein
      SORBIDRAFT_01g012450 (Sb01g012450)

<400> SEQUENCE: 4

Met Glu Val Ser Thr Ile Ser Phe Ser Ser Pro Ser Ser Ser Pro Pro
1               5                   10                  15

Ser Leu Ser Pro Ser Pro Pro Pro Ser Gln Gln Gln Gln His Gln Pro
            20                  25                  30

Arg Gly Ala Thr Pro Ala Asp Leu Glu Ala Val Gly Leu Arg Arg Leu
        35                  40                  45

Ser Asp Asn Leu Gln Arg Leu Leu Asp Pro Ala Phe Leu Asn Cys Ala
    50                  55                  60

Asp Ala Glu Ile Ala Leu Ala Pro Ala Lys Gly Gly Gly Ala Val Gly
65                  70                  75                  80

Val His Arg Cys Ile Leu Ala Ala Arg Ser Ala Phe Phe Leu His His

```
                    85                  90                  95
Phe Ala Ser Leu Pro Ala Pro Ala Gly Gly Gly Glu Arg Pro Arg
                100                 105                 110

Leu Glu Leu Ala Asp Leu Val Pro Gly Gly Arg His Ile Gly Gln Asp
            115                 120                 125

Ala Leu Val Pro Val Leu Gly Tyr Leu Tyr Thr Gly Arg Leu Lys Ser
        130                 135                 140

Pro Pro Gln Glu Ala Thr Val Cys Met Asp Asp Ala Cys Gly His Gly
145                 150                 155                 160

Thr Cys Arg Pro Ala Ile Asp Phe Val Val Glu Ser Met Tyr Ala Ala
                165                 170                 175

Ser Gly Phe Gln Ile Ser Glu Leu Ile Ser Leu Phe Gln Arg Arg Leu
            180                 185                 190

Ser Asp Phe Val Ser Glu Ala Leu Asp Glu Asp Val Val Pro Ile Ile
        195                 200                 205

His Val Ala Ser Thr Cys Asp Leu Gln Asp Leu Leu Asn Gln Cys Ile
    210                 215                 220

His Arg Val Ala Val Ser Thr Leu Asp Ser Arg Tyr Leu Glu Lys Glu
225                 230                 235                 240

Leu Pro Asp Asp Ile Tyr Cys Arg Ile Lys Glu Ile Arg Arg Ser Thr
                245                 250                 255

Phe His Asp Glu Ser Ser Glu Ser Ala Ile Leu Asp Pro Glu His Asp
            260                 265                 270

Lys Arg Val Arg Asn Ile Leu Lys Ala Leu Asp Ser Asp Asp Val Asp
        275                 280                 285

Leu Val Gly Leu Leu Leu Lys Glu Ser Thr Val Thr Leu Asp Asp Ala
    290                 295                 300

Phe Ala Ile His Tyr Ala Ala Ala Tyr Cys Glu Pro Lys Val Phe Ala
305                 310                 315                 320

Glu Leu Leu Lys Leu Asp Ser Ala Asn Val Asn Arg Lys Ser Asn Ser
                325                 330                 335

Gly Tyr Thr Pro Leu His Ile Ala Cys Met Arg Arg Glu Pro Asp Ile
            340                 345                 350

Ile Leu Ser Leu Val Glu Arg Gly Ala Ser Val Leu Glu Arg Thr Leu
        355                 360                 365

Asp Gly Arg Asp Ala Leu Thr Ile Cys Lys Arg Leu Thr Arg Glu Lys
    370                 375                 380

Asp Cys Asn Arg Lys Leu Glu Lys Tyr Glu Glu Lys Ser Lys Ala Tyr
385                 390                 395                 400

Leu Cys Ile Asp Ile Leu Glu Gln Glu Leu Lys Arg Lys Ser Phe Ile
                405                 410                 415

Leu Asp Pro Ile Ser Ile Glu Glu Ser Ile Ala Thr Pro Leu Leu Val
            420                 425                 430

Asp Asn Phe His Met Arg Leu Ile Asn Leu Glu Asn Arg Val Ala Phe
        435                 440                 445

Ala Arg Ile Phe Phe Pro Ser Glu Ala Lys Leu Val Met Arg Ile Ala
    450                 455                 460

Gln Ala Asp Ser Thr Glu Glu Phe Ala Gly Ile Thr Asn Phe Ser Lys
465                 470                 475                 480

Leu Lys Glu Val Asp Leu Asn Glu Thr Pro Thr Met Gln Asn Arg Arg
                485                 490                 495

Leu Arg Glu Arg Leu Asp Ala Leu Thr Lys Thr Val Glu Leu Gly Arg
            500                 505                 510
```

```
Arg Tyr Phe Pro His Cys Ser Asp Val Leu Asp Lys Phe Leu Asn Glu
    515                 520                 525

Glu Ser Thr Asp Leu Ile Phe Leu Glu Thr Gly Thr Pro Glu Asp Gln
    530                 535                 540

Arg Val Lys Arg Met Arg Phe Ser Glu Leu Lys Glu Asp Val Arg Lys
545                 550                 555                 560

Ala Phe Thr Lys Asp Lys Ala Val Ala Ala Ile Ala Ser Ser Ala
                565                 570                 575

Ser Ser Ser Ser Ser Pro Arg Cys Glu Gly Arg Gly Arg Ser Asn Arg
                580                 585                 590

Lys Leu Arg Pro Ser Arg
            595

<210> SEQ ID NO 5
<211> LENGTH: 574
<212> TYPE: PRT
<213> ORGANISM: Musa sp.
<220> FEATURE:
<223> OTHER INFORMATION: Musa ABB Group plantain cultivar
      Zhongshandajiao NPR1-like protein (NPR1-1)

<400> SEQUENCE: 5

Met Ala Arg Val Pro Thr Met Phe Pro Val Ala Pro Arg Leu Ala Pro
1               5                   10                  15

Arg Leu Leu Arg Gly Ala Gly Gly Trp Asp Gln Pro Arg Gly Leu Ser
                20                  25                  30

Leu Ser Lys Leu Ser Ser Asn Leu Glu His Leu Leu Leu Asp Thr Glu
            35                  40                  45

Phe Asp Cys Thr Asp Ala Glu Ile Ala Val Glu Gly Thr Pro Val Gly
    50                  55                  60

Ile His Arg Cys Ile Leu Ala Ala Arg Ser Arg Phe Phe Arg Asp Leu
65                  70                  75                  80

Phe Ser Arg Glu Gly Ser Gly Gly Asn Arg Gln Glu Gly Lys Pro Arg
                85                  90                  95

Tyr Val Met Asn Glu Leu Val Pro Gly Gly Arg Ile Gly Arg Glu Ala
                100                 105                 110

Leu Met Val Phe Leu Ser Tyr Leu Tyr Thr Gly Lys Leu Arg Ala Ala
            115                 120                 125

Pro Gln Asp Val Ser Ile Cys Val Asp Arg Phe Cys Ala His Asp Ala
    130                 135                 140

Cys Arg Pro Ala Ile Gly Phe Ala Val Glu Leu Leu Tyr Ala Ser Ser
145                 150                 155                 160

Val Phe Gln Ile Ala Glu Leu Val Ser Leu Leu Gln Arg Arg Leu Leu
                165                 170                 175

Asn Phe Val Asp Lys Ala Met Val Glu Asp Val Ile Pro Ile Leu Gln
                180                 185                 190

Val Ala Ser His Ser Lys Leu Asn Gln Leu Leu Ser His Cys Val Gln
            195                 200                 205

Arg Val Ala Arg Ser Asp Leu Asp Asp Ile Ala Leu Glu Lys Glu Leu
    210                 215                 220

Leu Gln Glu Val Ala Glu Ile Arg Leu Leu Arg Arg Glu Ser Gln
225                 230                 235                 240

Pro Lys Glu Ser Thr Ala Thr Val Asp Pro Met Leu Glu Lys Arg Ile
                245                 250                 255

Lys Arg Ile His Arg Ala Leu Asp Ser Asp Asp Val Glu Leu Val Lys
```

```
            260                 265                 270
Leu Leu Leu Asn Glu Ser Gly Val Thr Leu Asp Asp Thr Tyr Ala Leu
            275                 280                 285

His Tyr Ala Ala Ala Tyr Cys Asp Ser Lys Val Ile Ala Glu Leu Leu
            290                 295                 300

Asp Leu Gly Ser Ala Asn Val Asn Leu Lys Asn Asp Arg Gly Tyr Thr
305                 310                 315                 320

Pro Leu His Leu Ala Ala Met Arg Arg Glu Pro Ala Val Ile Val Ser
                    325                 330                 335

Leu Leu Thr Lys Gly Ala Ser Ala Leu Glu Thr Thr Ala Asp Gly Gln
                340                 345                 350

Asn Ala Val Arg Ile Cys Arg Arg Leu Thr Arg Ala Lys Asp Tyr Phe
            355                 360                 365

Thr Arg Thr Glu Gln Gly Gln Glu Ser Asn Lys Asn Lys Ile Cys Ile
            370                 375                 380

Asp Ile Leu Glu Arg Glu Met Met Arg Asn Pro Leu Ala Ala Glu Asp
385                 390                 395                 400

Ser Ala Thr Ser Pro Leu Leu Ala Asp Asp Leu His Met Lys Leu Leu
                    405                 410                 415

Tyr Leu Glu Asn Arg Val Ala Phe Ala Arg Leu Phe Phe Pro Ala Glu
                420                 425                 430

Ala Lys Leu Ala Met Glu Ile Ala His Ala Asn Thr Thr Ser Glu Phe
            435                 440                 445

Thr Gly Ile Ala Lys Ser Arg Ser Ser Asn Leu Arg Asp Val Asp
            450                 455                 460

Leu Asn Glu Thr Pro Val Val Gln Asn Lys Arg Leu Arg Ser Arg Val
465                 470                 475                 480

Asp Ala Leu Ser Lys Thr Val Glu Leu Gly Gln Arg Tyr Phe Pro His
                    485                 490                 495

Cys Ser Gln Val Leu Asp Lys Phe Leu Glu Asp Asp Leu Pro Asp Val
                500                 505                 510

Phe Tyr Leu Gln Lys Gly Thr Pro Asp Glu Gln Lys Val Lys Lys Leu
            515                 520                 525

Arg Phe Cys Glu Leu Lys Glu Asp Val Arg Lys Ala Phe Ser Lys Asp
            530                 535                 540

Lys Ala Gly Ser Leu Leu Leu Gly Leu Ser Ser Ser Ser Ser Thr Ser
545                 550                 555                 560

Ser Pro Lys Ser Glu Glu Lys Tyr His Met Val Ala Arg Asn
                    565                 570

<210> SEQ ID NO 6
<211> LENGTH: 621
<212> TYPE: PRT
<213> ORGANISM: Zea mays
<220> FEATURE:
<223> OTHER INFORMATION: maize regulatory protein NPR1

<400> SEQUENCE: 6

Met Glu Pro Ser Ser Ser Ile Thr Phe Ala Ser Ser Ser Ser Tyr Leu
1               5                   10                  15

Ser Asn Gly Ser Ser Pro Cys Ser Val Ala Leu Pro Pro Gly Pro
            20                  25                  30

Pro Gln Thr Pro Pro Leu Pro Ala Gly Gln Gly Trp Gly Ala Gly Val
            35                  40                  45

Ala Ala Ala Gly Ser Gly Gly Ser Val Glu Ala Val Ser Leu Asn Arg
```

```
        50                  55                  60
Leu Ser Lys Asn Leu Glu Arg Leu Leu Leu Asp Pro Asp Leu Asp Cys
 65                  70                  75                  80

Ser Asp Ala Asp Val Asp Val Pro Asp Gly Gly Pro Val Pro Ile
                 85                  90                  95

His Arg Cys Ile Leu Ala Ala Arg Ser Asp Phe Phe Tyr Asp Leu Phe
                    100                 105                 110

Ala Ala Arg Gly Arg Ala Gly Ala Ala Arg Gly Asp Ala Ala Ala Gly
                115                 120                 125

Ala Gly Val Ala Ala Glu Gly Ala Ala Ser Gly Arg Pro Arg Tyr Lys
                130                 135                 140

Met Glu Asp Leu Val Pro Ala Gly Arg Val Gly Arg Glu Ala Phe Gln
145                 150                 155                 160

Ala Phe Leu Gly Tyr Leu Tyr Thr Gly Lys Leu Arg Pro Ala Pro Val
                    165                 170                 175

Asp Val Val Ser Cys Ala Asp Pro Val Cys His His Asp Ser Cys Pro
                180                 185                 190

Pro Ala Ile Arg Ser Ala Val Glu Leu Met Tyr Ala Ala Cys Thr Phe
                195                 200                 205

Lys Ile Pro Glu Leu Thr Ser Leu Phe Gln Arg Leu Leu Asn Phe
210                 215                 220

Val Asp Lys Thr Leu Val Glu Asp Val Ile Pro Ile Leu Glu Val Ala
225                 230                 235                 240

Ser His Ser Gly Leu Thr Gln Val Ile Asp Lys Cys Ile Gln Arg Ile
                    245                 250                 255

Ala Arg Ser Asp Leu Asp Asp Ile Ser Leu Asp Lys Glu Leu Pro Pro
                260                 265                 270

Glu Ala Val Asp Glu Ile Lys Asn Leu Arg Lys Lys Ser Gln Thr Ala
                275                 280                 285

Asp Gly Asp Thr Phe Ile Ser Asp Pro Val His Glu Lys Arg Val Arg
                290                 295                 300

Arg Ile His Arg Ala Leu Asp Ser Asp Asp Val Glu Leu Val Lys Leu
305                 310                 315                 320

Leu Leu Asn Glu Ser Asp Ile Thr Leu Asp Asp Ala Asn Ala Leu His
                    325                 330                 335

Tyr Ala Ala Ser Tyr Cys Asp Pro Lys Val Val Ser Glu Leu Leu Asp
                340                 345                 350

Leu Ala Met Ala Asn Leu Asn Leu Lys Asn Ser Arg Gly Tyr Thr Ala
                355                 360                 365

Leu His Leu Ala Ala Met Arg Arg Glu Pro Ala Ile Ile Met Cys Leu
                370                 375                 380

Leu Asn Lys Gly Ala Asn Val Ser Gln Leu Thr Ala Asp Gly Ser Ser
385                 390                 395                 400

Ala Ile Gly Ile Cys Arg Arg Leu Thr Arg Ala Lys Asp Tyr Asn Thr
                    405                 410                 415

Lys Met Glu Gln Gly Gln Glu Ser Asn Lys Asp Arg Leu Cys Ile Asp
                420                 425                 430

Ile Leu Glu Arg Glu Met Met Arg Asn Pro Met Ala Val Glu Asp Ala
                435                 440                 445

Val Thr Ser Pro Leu Leu Ala Asp Asp Leu His Met Lys Leu Leu Tyr
                450                 455                 460

Leu Glu Asn Arg Val Ala Phe Ala Arg Leu Phe Phe Pro Ala Glu Ala
465                 470                 475                 480
```

```
Lys Val Ala Met Gln Ile Ala Gln Ala Asp Thr Thr Glu Glu Phe Gly
                485                 490                 495

Gly Ile Val Ala Val Ala Ala Ser Thr Ser Gly Lys Leu Arg Glu Val
            500                 505                 510

Asp Leu Asn Glu Thr Pro Val Thr Gln Asn Lys Arg Leu Arg Ser Arg
        515                 520                 525

Val Asp Ala Leu Met Lys Thr Val Glu Leu Gly Arg Arg Tyr Phe Pro
    530                 535                 540

Asn Cys Ser Gln Val Leu Asp Lys Phe Leu Glu Asp Leu Pro Glu
545                 550                 555                 560

Gly Leu Asp Gln Phe Tyr Leu Gln Arg Gly Thr Ala Asp Glu Gln Lys
                565                 570                 575

Val Lys Arg Met Arg Phe Cys Glu Leu Lys Glu Asp Val Leu Lys Ala
            580                 585                 590

Phe Ser Lys Asp Lys Ala Glu Gly Ser Val Phe Ser Gly Leu Ser Ser
        595                 600                 605

Ser Ser Ser Cys Ser Pro Pro Gln Lys Tyr Ala Gln Arg
    610                 615                 620

<210> SEQ ID NO 7
<211> LENGTH: 595
<212> TYPE: PRT
<213> ORGANISM: Musa sp.
<220> FEATURE:
<223> OTHER INFORMATION: Musa ABB Group plantain cultivar Dongguan
      Dajiao NPR1-like protein

<400> SEQUENCE: 7

Met Pro Asn Pro Thr Glu Pro Ser Ser Ile Ser Phe Ala Ser Ser
 1               5                  10                  15

Ser Tyr Leu Ser Asn Gly Ser Ser Ala Tyr His Val Pro Gly Gly Thr
            20                  25                  30

Ala Pro Ser Pro Ser Pro Pro Ala Ala Pro Glu Gly Gly Thr Asn
        35                  40                  45

Leu Glu Val Leu Ser Leu Ser Lys Leu Ser Ser Asn Leu Glu His Leu
    50                  55                  60

Leu Leu Asp Thr Glu Phe Asp Cys Thr Asp Ala Glu Ile Ala Val Glu
65                  70                  75                  80

Gly Thr Pro Val Gly Ile His Arg Cys Ile Leu Ala Ala Arg Ser Arg
                85                  90                  95

Phe Phe Arg Asp Leu Phe Ser Arg Glu Gly Ser Gly Gly Asn Arg Gln
            100                 105                 110

Glu Gly Lys Pro Arg Tyr Val Met Asn Glu Leu Val Pro Gly Gly Arg
        115                 120                 125

Ile Gly Arg Glu Ala Leu Met Val Phe Leu Ser Tyr Leu Tyr Thr Gly
    130                 135                 140

Lys Leu Arg Ala Ala Pro Gln Asp Val Ser Ile Cys Val Asp Arg Phe
145                 150                 155                 160

Cys Ala His Asp Ala Cys Arg Pro Ala Ile Gly Phe Ala Val Glu Leu
                165                 170                 175

Leu Tyr Ala Ser Ser Val Phe Gln Ile Ala Glu Leu Val Ser Leu Leu
            180                 185                 190

Gln Arg Arg Leu Leu Asn Phe Val Asp Lys Ala Met Val Glu Asp Val
        195                 200                 205

Ile Pro Ile Leu Gln Val Ala Ser His Ser Lys Leu Asn Gln Leu Leu
```

```
                210                 215                 220
Ser His Cys Val Gln Arg Val Ala Arg Ser Asp Leu Asp Val Ser
225                 230                 235                 240

Leu Glu Lys Glu Leu Pro Gln Glu Val Ala Glu Ile Arg Leu Leu
            245                 250                 255

Arg Arg Glu Ser Gln Pro Lys Glu Ser Thr Ala Thr Val Asp Pro Met
                260                 265                 270

Leu Glu Lys Arg Ile Lys Arg Ile His Arg Ala Leu Asp Ser Asp Asp
            275                 280                 285

Val Glu Leu Val Lys Leu Leu Ser Glu Ser Gly Val Thr Leu Asp
290                 295                 300

Asp Ala Tyr Ala Leu His Tyr Ala Ala Ala Tyr Cys Asp Ser Lys Val
305                 310                 315                 320

Val Ala Glu Leu Leu Asp Leu Gly Ser Ala Asn Val Asn Leu Lys Asn
                325                 330                 335

Asp Arg Gly Tyr Thr Pro Leu His Leu Ala Ala Met Arg Arg Glu Pro
            340                 345                 350

Ala Val Ile Val Ser Leu Leu Thr Lys Gly Ala Ser Ala Leu Glu Thr
                355                 360                 365

Thr Ala Asp Gly Gln Asn Ala Val Arg Ile Cys Arg Arg Leu Thr Arg
370                 375                 380

Ala Lys Asp Tyr Phe Thr Arg Thr Glu Gln Gly Gln Glu Ser Asn Lys
385                 390                 395                 400

Asn Lys Ile Cys Ile Asp Ile Leu Glu Arg Glu Met Met Arg Asn Pro
                405                 410                 415

Leu Ala Ala Glu Asp Ser Ala Thr Ser Pro Leu Leu Ala Asp Asp Leu
            420                 425                 430

His Met Lys Leu Leu Tyr Leu Glu Asn Arg Val Ala Phe Ala Arg Leu
                435                 440                 445

Phe Phe Pro Ala Glu Ala Lys Leu Ala Met Glu Ile Ala His Ala Asn
            450                 455                 460

Thr Thr Ser Glu Phe Thr Gly Ile Ala Lys Ser Arg Ser Ser Asn
465                 470                 475                 480

Leu Arg Asp Val Asp Leu Asn Glu Thr Pro Val Val Gln Asn Lys Arg
                485                 490                 495

Leu Arg Ser Arg Val Asp Ala Leu Ser Lys Thr Val Glu Leu Gly Arg
            500                 505                 510

Arg Tyr Phe Pro His Cys Ser Gln Val Leu Asp Lys Phe Leu Glu Asp
            515                 520                 525

Asp Leu Pro Asp Val Phe Tyr Leu Gln Lys Gly Thr Pro Asp Glu Gln
530                 535                 540

Lys Val Lys Lys Leu Arg Phe Cys Glu Leu Lys Glu Asp Val Arg Lys
545                 550                 555                 560

Ala Phe Ser Lys Asp Lys Ala Gly Ser Leu Leu Gly Leu Ser Ser
                565                 570                 575

Ser Ser Ser Thr Ser Ser Pro Lys Ser Glu Glu Lys Tyr His Met Val
            580                 585                 590

Ala Arg Asn
        595

<210> SEQ ID NO 8
<211> LENGTH: 590
<212> TYPE: PRT
<213> ORGANISM: Ricinus communis
```

<220> FEATURE:
<223> OTHER INFORMATION: castor bean cultivar Hale putative regulatory
    protein NPR1, locus RCOM_1160850

<400> SEQUENCE: 8

Met Ala Asn Leu Ser Glu Pro Ser Ser Leu Ser Phe Thr Ser Ser
1               5                   10                  15

Ser His Ala Ser Asn Gly Ser Ile Thr Gln Ala Ile Ser Thr Ser Ser
            20                  25                  30

Gly Phe Glu Ala Arg Ser Ser Leu Glu Val Ile Ser Leu Thr Lys Leu
                35                  40                  45

Ser Ser Asn Leu Glu Lys Leu Leu Ile Asp Ser Ser Cys Asp Tyr Ser
50                  55                  60

```
                385                 390                 395                 400
Glu Arg Glu Met Arg Arg Asn Pro Met Ala Gly Asp Ala Ser Ile Thr
                405                 410                 415

Ser Gln Ala Thr Pro Asp Asp Leu His Met Lys Leu Leu Tyr Leu Glu
                420                 425                 430

Asn Arg Val Ala Phe Ala Arg Leu Phe Phe Pro Ala Glu Ala Lys Val
                435                 440                 445

Ala Met Asp Ile Ala His Ala Gln Thr Thr Ser Glu Phe Ala Gly Leu
                450                 455                 460

Ser Ala Thr Lys Gly Ser Asn Gly Asn Phe Arg Glu Val Asp Leu Asn
465                 470                 475                 480

Glu Thr Pro Ile Met Gln Asn Lys Arg Leu Arg Ser Arg Leu Glu Ala
                485                 490                 495

Leu Met Lys Thr Val Glu Met Gly Arg Arg Tyr Phe Pro Lys Cys Ser
                500                 505                 510

Glu Val Leu Asp Lys Phe Met Glu Asp Asp Leu Pro Asp Leu Phe Tyr
                515                 520                 525

Leu Glu Lys Gly Thr Pro Asp Glu Gln Arg Ile Lys Arg Met Arg Phe
                530                 535                 540

Met Glu Leu Lys Asp Asp Val Gln Lys Ala Phe Asn Lys Asp Lys Ala
545                 550                 555                 560

Glu Arg Ser Val Leu Ser Ser Ser Ser Ser Ser Ser Leu Lys Asp
                565                 570                 575

Gly Thr Asp Lys Leu Ala Glu Glu Leu Pro Asp Ser Met Ser
                580                 585                 590

<210> SEQ ID NO 9
<211> LENGTH: 589
<212> TYPE: PRT
<213> ORGANISM: Populus trichocarpa
<220> FEATURE:
<223> OTHER INFORMATION: black cottonwood (Western balsam polar)
      putative NPR1/NIM1-like regulatory protein, locus tag
      POPTRDRAFT_253241

<400> SEQUENCE: 9

Met Ala Asn Phe Ser Glu Pro Ser Ser Ser Leu Ser Tyr Thr Ser Ser
1               5                   10                  15

Ser His Leu Ser Asn Gly Ser Ile Ser His Asn Ile Ser Asn Ser Ser
                20                  25                  30

Gly Ala Glu Ala Gly Thr Ser Leu Glu Val Ile Ser Leu Asn Lys Leu
                35                  40                  45

Ser Ser Asn Leu Glu Gln Leu Leu Ile Asp Ser Thr Cys Asp Tyr Ser
50                  55                  60

Asp Ala Asp Ile Val Val Glu Gly Thr Ala Ile Gly Val His Arg Cys
65                  70                  75                  80

Ile Leu Gly Ala Arg Ser Lys Phe Phe His Glu Leu Phe Arg Arg Glu
                85                  90                  95

Lys Gly Ser Ser Glu Lys Glu Gly Lys Pro Lys Tyr Cys Met Ser Asp
                100                 105                 110

Leu Leu Pro Cys Gly Lys Val Gly Tyr Glu Ala Phe Leu Ile Phe Leu
                115                 120                 125

Ser Tyr Leu Tyr Thr Gly Lys Leu Lys Pro Ser Pro Met Glu Val Ser
                130                 135                 140

Thr Cys Val Asp Asn Val Cys Ala His Asp Ala Cys Arg Pro Ala Ile
145                 150                 155                 160
```

-continued

```
Asn Phe Ala Val Glu Leu Met Tyr Ala Ser Ser Ile Phe Gln Val Pro
                165                 170                 175
Glu Leu Val Ser Leu Phe Gln Arg Arg Leu Gln Asn Phe Val Gly Lys
            180                 185                 190
Ala Leu Val Glu Asp Met Ile Pro Ile Leu Val Val Ala Phe His Cys
        195                 200                 205
Gln Leu Ser Gln Leu Val Thr Gln Cys Val Asp Arg Ile Ala Arg Ser
    210                 215                 220
Asp Leu Asp Asn Ile Ser Ile Glu Lys Glu Leu Pro His Asp Val Ala
225                 230                 235                 240
Val Glu Ile Lys Leu Leu Arg Arg Lys Ser Ile Ser Asp Glu Glu Asn
                245                 250                 255
Asn Thr Glu Ala Val Asp Ala Leu Arg Glu Lys Arg Ile Lys Arg Ile
            260                 265                 270
His Met Ala Leu Asp Ser Asp Asp Val Glu Leu Val Lys Leu Leu Leu
        275                 280                 285
Thr Glu Ser Asp Ile Thr Leu Asp Asp Ala Asn Ala Leu His Tyr Ala
    290                 295                 300
Ala Ser Tyr Cys Asp Leu Lys Val Val Ser Glu Val Leu Ser Leu Gly
305                 310                 315                 320
Leu Ala Asp Val Asn Leu Arg Asn Ser Arg Gly Tyr Thr Val Leu His
                325                 330                 335
Ile Ala Ala Met Arg Lys Glu Pro Ser Val Ile Val Ser Met Leu Ala
            340                 345                 350
Lys Gly Ala Ser Ala Leu Asp Leu Thr Ser Asp Gly Gln Ser Ala Val
        355                 360                 365
Ser Ile Cys Arg Arg Leu Thr Arg Pro Lys Asp Tyr His Ala Lys Thr
    370                 375                 380
Glu Gln Gly Gln Glu Ala Asn Lys Asp Arg Leu Cys Ile Asp Ile Leu
385                 390                 395                 400
Glu Arg Glu Met Arg Arg Asn Pro Met Ala Gly Ser Ala Ser Ile Thr
                405                 410                 415
Ser His Thr Met Val Asp Asp Leu His Met Lys Leu Leu Tyr Leu Glu
            420                 425                 430
Asn Arg Val Ala Phe Ala Arg Leu Phe Phe Pro Thr Glu Ala Lys Leu
        435                 440                 445
Ala Met Asp Ile Ala His Ala Ala Thr Thr Pro Glu Phe Ala Gly Leu
    450                 455                 460
Ala Ala Ser Lys Gly Ser Asn Gly Asn Leu Arg Glu Val Asp Leu Asn
465                 470                 475                 480
Glu Thr Pro Ile Met Gln Asn Lys Arg Leu Arg Ser Arg Met Glu Ala
                485                 490                 495
Leu Met Lys Thr Ala Val Phe Val Met Met Ala Val Glu Met Gly Arg
            500                 505                 510
Arg Tyr Phe Pro Ser Cys Ser Glu Val Leu Asp Lys Phe Met Glu Asp
        515                 520                 525
Asp Leu Pro Asp Leu Phe Tyr Leu Glu Lys Gly Thr Pro Asp Glu Gln
    530                 535                 540
Arg Ile Lys Arg Thr Arg Phe Met Glu Leu Lys Glu Asp Val His Arg
545                 550                 555                 560
Ala Phe Thr Lys Asp Lys Ala Glu Ile Asn Arg Thr Gly Leu Ser Ser
                565                 570                 575
```

Ser Ser Ser Ser Ser Leu Lys Asp Gly Ile Ser Asn
            580                 585

<210> SEQ ID NO 10
<211> LENGTH: 587
<212> TYPE: PRT
<213> ORGANISM: Vitis vinifera
<220> FEATURE:
<223> OTHER INFORMATION: wine grape cultivar PN40024 predicted
      hypothetical protein LOC100247744, locus tag GSVIVT00031933001

<400> SEQUENCE: 10

Met Ala Asn Ser Ala Glu Pro Ser Ser Leu Ser Phe Thr Ser Ser
 1               5                  10                  15

Ser His Ile Ser Asn Ala Val Thr Ser His Asn Met Ser Ser Ser
             20                  25                  30

Gly Ser Glu Thr Gly Pro Ser Leu Glu Ile Ile Ser Leu Ser Lys Leu
             35                  40                  45

Ser Ser Asn Leu Glu Gln Leu Leu Val Asp Ser Gly Cys Asp Tyr Ser
             50                  55                  60

Asp Ala Glu Ile Ile Val Glu Gly Ile Pro Val Gly Val His Arg Cys
65                   70                  75                  80

Ile Leu Ala Ala Arg Ser Arg Phe Phe Tyr Asp Leu Phe Lys Arg Glu
                 85                  90                  95

Lys Ser Ser Glu Lys Asp Gly Lys Pro Arg Tyr Cys Met Ser Asp
            100                 105                 110

Phe Leu Pro Tyr Gly Lys Val Gly Tyr Glu Ala Phe Leu Ile Phe Leu
            115                 120                 125

Ser Tyr Leu Tyr Thr Gly Lys Leu Lys Ala Ser Pro Leu Glu Val Ser
            130                 135                 140

Thr Cys Val Asp Thr Gly Cys Ala His Asp Ala Cys Arg Pro Ala Ile
145                 150                 155                 160

Asp Phe Ser Val Glu Leu Met Tyr Ala Ser Ala Ile Phe Gln Val Pro
                165                 170                 175

Glu Leu Val Ser Leu Phe Gln Arg Arg Leu Thr Asn Phe Ile Gly Lys
            180                 185                 190

Ala Leu Leu Glu Asp Val Ile Pro Ile Leu Val Val Ala Tyr His Cys
            195                 200                 205

Lys Ser Ser Val Leu Val Asn Gln Cys Val Asp Arg Val Ala Arg Ser
            210                 215                 220

Asp Leu Asp Ser Ile Ser Leu Glu Lys Asp Leu Pro Tyr Glu Val Ala
225                 230                 235                 240

Glu Ser Ile Lys Leu Leu Arg Leu Lys Ser Gln Pro Asp Asp Glu Cys
                245                 250                 255

Asn Thr Val Pro Val Asp Pro Val His Glu Lys Arg Val Arg Arg Ile
            260                 265                 270

Leu Lys Ala Leu Asp Ser Asp Val Glu Leu Val Lys Leu Leu Leu
            275                 280                 285

Ser Glu Ser Gly Ile Thr Leu Asp Glu Ala Tyr Ala Leu His Tyr Ala
            290                 295                 300

Ala Ala Tyr Cys Asp Pro Lys Val Val Ser Glu Val Leu Ser Leu Gly
305                 310                 315                 320

Leu Ala Asp Val Asn Arg His Asn Pro Arg Gly Tyr Thr Val Leu His
                325                 330                 335

Val Ala Ala Met Arg Lys Glu Pro Ser Ile Ile Val Ser Leu Leu Thr
            340                 345                 350

```
Lys Gly Ala His Ala Ser Glu Arg Thr Ser Asp Gly Gln Ser Ala Val
        355                 360                 365

Ser Ile Cys Arg Arg Leu Thr Arg Pro Lys Asp Tyr His Ala Lys Met
    370                 375                 380

Glu Gln Gly Gln Glu Thr Asn Lys Asp Arg Ile Cys Ile Asp Val Leu
385                 390                 395                 400

Glu Arg Glu Met Arg Arg Asn Pro Leu Ala Gly Asp Val Ser Ile Ser
                405                 410                 415

Ser Pro Thr Met Ala Asp Asp Leu His Met Lys Leu Leu Tyr Leu Glu
                420                 425                 430

Asn Arg Val Ala Phe Ala Arg Leu Phe Phe Pro Ser Glu Ala Lys Leu
            435                 440                 445

Ala Met Glu Ile Ala His Ala Glu Thr Thr Ser Glu Phe Ala Gly Leu
        450                 455                 460

Ser Ala Ser Lys Arg Ser Ser Gly Asn Leu Arg Glu Val Asp Leu Asn
465                 470                 475                 480

Glu Thr Pro Ile Met Gln Asn Gln Arg Leu Arg Ser Arg Met Asn Ala
                485                 490                 495

Leu Val Lys Thr Val Glu Met Gly Arg Arg Tyr Phe Pro His Cys Ser
            500                 505                 510

Gln Val Leu Asp Lys Phe Met Glu Asp Asp Leu Pro Asp Leu Phe Tyr
        515                 520                 525

Leu Glu Lys Gly Thr Leu Asp Glu Gln Arg Ile Lys Arg Thr Arg Phe
    530                 535                 540

Met Glu Leu Lys Glu Asp Val Gln Arg Ala Phe Thr Lys Asp Lys Ala
545                 550                 555                 560

Glu Phe Asn Arg Ser Gly Leu Ser Ser Ser Ser Ser Ser Ser Ser Leu
                565                 570                 575

Lys Asp Asn Leu Ser His Lys Ala Arg Lys Leu
                580                 585

<210> SEQ ID NO 11
<211> LENGTH: 590
<212> TYPE: PRT
<213> ORGANISM: Glycine max
<220> FEATURE:
<223> OTHER INFORMATION: soybean NPR1-1 (GmNPR1-1) protein

<400> SEQUENCE: 11

Met Ala Tyr Ser Ala Glu Pro Ser Ser Leu Ser Phe Thr Ser Ser
1               5                   10                  15

Ser His Leu Ser Asn Gly Ser Val Ser His Asn Ile Cys Pro Ser Tyr
            20                  25                  30

Gly Ser Asp Pro Gly Pro Asn Leu Glu Ala Ile Ser Leu Ser Lys Leu
        35                  40                  45

Ser Ser Asn Leu Glu Gln Leu Leu Ile Glu Pro Asp Cys Asp Tyr Ser
    50                  55                  60

Asp Ala Asp Leu Val Val Glu Gly Ile Pro Val Ser Val His Arg Cys
65                  70                  75                  80

Ile Leu Ala Ser Arg Ser Lys Phe Phe His Glu Leu Phe Lys Arg Glu
                85                  90                  95

Lys Gly Ser Ser Glu Lys Glu Gly Lys Leu Lys Tyr Asn Met Asn Asp
            100                 105                 110

Leu Leu Pro Tyr Gly Lys Val Gly Tyr Glu Ala Phe Leu Ile Phe Leu
        115                 120                 125
```

```
Gly Tyr Val Tyr Thr Gly Lys Leu Lys Pro Ser Pro Met Glu Val Ser
            130                 135                 140

Thr Cys Val Asp Asn Val Cys Ala His Asp Ala Cys Arg Pro Ala Ile
145                 150                 155                 160

Asn Phe Ala Val Glu Leu Met Tyr Ala Ser Ser Ile Phe Gln Ile Pro
                165                 170                 175

Glu Leu Val Ser Leu Phe Gln Arg Arg Leu Leu Asn Phe Ile Gly Lys
            180                 185                 190

Ala Leu Val Glu Asp Val Ile Pro Ile Leu Thr Val Ala Phe His Cys
            195                 200                 205

Gln Ser Asn Gln Leu Val Asn Gln Cys Ile Asp Arg Val Ala Arg Ser
210                 215                 220

Asp Leu Asp Gln Ile Ser Ile Asp Gln Glu Leu Pro His Glu Leu Ser
225                 230                 235                 240

Gln Lys Val Lys Leu Leu Arg Arg Lys Pro Gln Gln Asp Val Glu Asn
                245                 250                 255

Asp Ala Ser Val Val Asp Ala Leu Ser Leu Lys Arg Ile Thr Arg Ile
                260                 265                 270

His Lys Ala Leu Asp Ser Asp Val Glu Leu Val Lys Leu Leu Leu
            275                 280                 285

Asn Glu Ser Asp Ile Thr Leu Asp Glu Ala Asn Ala Leu His Tyr Ala
290                 295                 300

Ala Ala Tyr Cys Asp Pro Lys Val Val Ser Glu Val Leu Gly Leu Gly
305                 310                 315                 320

Leu Ala Asn Val Asn Leu Arg Asn Ser Arg Gly Tyr Thr Val Leu His
                325                 330                 335

Ile Ala Ala Met Arg Lys Glu Pro Ser Ile Ile Val Ser Leu Leu Thr
            340                 345                 350

Lys Gly Ala Cys Ala Ser Asp Leu Thr Phe Asp Gly Gln Ser Ala Val
            355                 360                 365

Ser Ile Cys Arg Arg Leu Thr Arg Pro Lys Asp Tyr His Ala Lys Thr
370                 375                 380

Glu Gln Gly Lys Glu Thr Asn Lys Asp Arg Ile Cys Ile Asp Val Leu
385                 390                 395                 400

Glu Arg Glu Met Arg Arg Asn Pro Met Ala Gly Asp Ala Cys Met Ser
                405                 410                 415

Ser His Thr Met Ala Asp Asp Leu His Met Lys Leu Leu Tyr Leu Glu
                420                 425                 430

Asn Arg Val Ala Phe Ala Arg Leu Phe Phe Pro Ser Glu Ala Lys Leu
            435                 440                 445

Ala Met Asp Ile Ala His Ala Glu Thr Thr Ser Glu Phe Ala Gly Leu
450                 455                 460

Ser Ala Ser Asn Ser Lys Gly Ser Asn Gly Asn Leu Arg Glu Val Asp
465                 470                 475                 480

Leu Asn Glu Thr Pro Ile Val Gln Asn Lys Arg Leu Leu Ser Arg Met
                485                 490                 495

Glu Ala Leu Thr Lys Thr Val Glu Met Gly Arg Arg Tyr Phe Pro His
                500                 505                 510

Cys Ser Glu Val Leu Asp Lys Phe Met Glu Asp Leu Pro Asp Leu
            515                 520                 525

Phe Tyr Leu Glu Lys Gly Thr His Glu Glu Gln Arg Ile Lys Arg Thr
530                 535                 540
```

```
Arg Phe Met Glu Leu Lys Asp Asp Val His Lys Ala Phe Asn Lys Asp
545                 550                 555                 560

Lys Ala Glu Phe Ser Arg Ser Gly Ile Ser Ser Ser Ser Ser Ser Ser
            565                 570                 575

Ser Leu Arg Asp Ser Val Val His Tyr Lys Ala Arg Lys Val
        580                 585                 590

<210> SEQ ID NO 12
<211> LENGTH: 621
<212> TYPE: PRT
<213> ORGANISM: Sorghum bicolor
<220> FEATURE:
<223> OTHER INFORMATION: sorghum cultivar BTx623 hypothetical protein
      SORBIDRAFT_03g035720 (Sb03g035720)

<400> SEQUENCE: 12

Met Glu Pro Ser Ser Ser Ile Thr Phe Ala Ser Ser Ser Tyr Leu
 1               5                  10                  15

Ser Asn Gly Ser Ser Pro Cys Ser Val Ala Met Pro Pro Gly Pro
            20                  25                  30

Pro Gln Ala Pro Pro Leu Ala Gly Gly Glu Gly Trp Gly Gly Gly Val
            35                  40                  45

Ala Thr Ala Gly Ser Gly Ser Ser Val Glu Val Ala Ser Leu Asn Arg
50                  55                  60

Leu Ser Lys Asn Leu Glu Arg Leu Leu Leu Asp Arg Asp Leu Asp Cys
65                  70                  75                  80

Ser Asp Ala Asp Val Glu Val Pro Asp Gly Gly Pro Pro Val Pro Ile
                85                  90                  95

His Arg Cys Ile Leu Ala Ala Arg Ser Asp Phe Phe Tyr Asp Leu Phe
            100                 105                 110

Ala Ala Arg Gly Arg Gly Gly Ala Leu Arg Gly Asp Ala Thr Ala Gly
            115                 120                 125

Ala Gly Gly Ala Ala Glu Gly Ala Ala Ser Gly Arg Pro Arg Tyr Lys
130                 135                 140

Met Glu Glu Leu Val Pro Gly Gly Arg Val Gly Arg Glu Ala Phe Gln
145                 150                 155                 160

Ala Phe Leu Gly Tyr Met Tyr Thr Gly Lys Leu Arg Pro Ser Pro Val
                165                 170                 175

Asp Val Val Ser Cys Ala Asp Pro Val Cys Pro His Ser Cys Pro
            180                 185                 190

Pro Ala Ile Arg Ser Ala Val Glu Leu Met Tyr Ala Ala Cys Thr Phe
            195                 200                 205

Lys Ile Pro Glu Leu Thr Ser Leu Phe Gln Arg Arg Leu Leu Asn Phe
210                 215                 220

Val Asp Lys Thr Leu Val Glu Asp Val Ile Pro Ile Leu Lys Val Ala
225                 230                 235                 240

Ser His Ser Gly Leu Thr Gln Val Ile Asp Lys Cys Ile Gln Arg Ile
                245                 250                 255

Ala Arg Ser Asp Leu Asp Ile Ser Leu Asp Lys Glu Leu Pro Pro
            260                 265                 270

Glu Ala Val Glu Glu Ile Lys Asn Leu Arg Lys Lys Ser Gln Thr Ala
            275                 280                 285

Asp Gly Asp Gly Asp Ala Phe Ile Ser Asp Pro Val His Glu Lys Arg
290                 295                 300

Val Arg Arg Ile His Arg Ala Leu Asp Ser Asp Asp Val Glu Leu Val
305                 310                 315                 320
```

-continued

```
Lys Leu Leu Leu Asn Glu Ser Asp Ile Thr Leu Asp Asp Ala Asn Ala
                325                 330                 335

Leu His Tyr Ala Ala Ser Tyr Cys Asp Asn Lys Val Val Ser Glu Leu
            340                 345                 350

Leu Asp Leu Ala Leu Ala Asn Leu Asn Leu Lys Asn Ser Arg Gly Tyr
        355                 360                 365

Thr Ala Leu His Leu Ala Ala Met Arg Arg Glu Pro Ala Ile Ile Met
    370                 375                 380

Cys Leu Leu Asn Lys Gly Ala Asn Val Ser Gln Leu Thr Ala Asp Gly
385                 390                 395                 400

Arg Ser Ala Ile Gly Ile Cys Arg Arg Leu Thr Arg Leu Lys Asp Tyr
                405                 410                 415

Asn Thr Lys Met Glu Gln Gly Gln Glu Ser Asn Lys Asp Arg Leu Cys
            420                 425                 430

Ile Asp Ile Leu Glu Arg Glu Met Met Arg Asn Pro Met Ala Val Glu
        435                 440                 445

Asp Ala Val Thr Ser Pro Leu Leu Ala Asp Asp Leu His Met Lys Leu
    450                 455                 460

Leu Tyr Leu Glu Asn Arg Val Ala Phe Ala Arg Leu Phe Phe Pro Ala
465                 470                 475                 480

Glu Ala Lys Val Ala Met Gln Ile Ala Gln Ala Asp Thr Thr Glu Glu
                485                 490                 495

Phe Gly Gly Ile Val Ala Ala Ser Thr Ser Gly Lys Leu Arg Glu Val
            500                 505                 510

Asp Leu Asn Glu Thr Pro Val Thr Gln Asn Lys Arg Leu Arg Ser Arg
        515                 520                 525

Val Asp Ala Leu Met Lys Thr Val Glu Leu Gly Arg Arg Tyr Phe Pro
    530                 535                 540

Asn Cys Ser Gln Val Leu Asp Lys Phe Leu Glu Asp Leu Pro Asp
545                 550                 555                 560

Gly Leu Asp Gln Phe Tyr Leu Gln Arg Gly Thr Ala Asp Glu Gln Lys
                565                 570                 575

Val Lys Arg Met Arg Phe Cys Glu Leu Lys Glu Asp Val Leu Lys Ala
            580                 585                 590

Phe Ser Lys Asp Lys Ala Asp Ser Ser Met Leu Ser Gly Leu Ser Ser
        595                 600                 605

Ser Ser Ser Cys Ser Pro Pro Gln Lys Ser Ala Lys Arg
    610                 615                 620

<210> SEQ ID NO 13
<211> LENGTH: 591
<212> TYPE: PRT
<213> ORGANISM: Helianthus annuus
<220> FEATURE:
<223> OTHER INFORMATION: sunflower NIM1-like protein 1 (NML1, HaNML1)

<400> SEQUENCE: 13

Met Ala Asn Ser Ser Glu Pro Ser Ser Ser Ile Ser Phe Thr Ser Ser
1               5                   10                  15

Ser His Ile Ser Asn Gly Ala Thr Ser Tyr Asn Ile Pro Pro Pro Ser
            20                  25                  30

Ile Pro Glu Pro Arg Ser Asn Ile Glu Ile Ile Gly Leu Asn Arg Leu
        35                  40                  45

Ser Thr Asn Leu Glu Lys Leu Val Phe Asp Ser Gly Ser Glu Ser Asp
    50                  55                  60
```

```
Cys Asn Tyr Ser Asp Ala Glu Val Val Glu Gly Ile Ser Val Gly
 65                  70                  75                  80

Ile His Arg Cys Ile Leu Ala Thr Arg Ser Thr Phe Phe Ser Asp Leu
                 85                  90                  95

Phe Lys Lys Asn Lys Gly Cys Val Glu Lys Asp Ser Lys Pro Lys Tyr
            100                 105                 110

Asn Met Ser Asp Leu Leu Pro Tyr Gly Ser Val Gly Tyr Asp Ala Phe
        115                 120                 125

Leu Val Phe Leu Ser Tyr Val Tyr Thr Gly Lys Leu Lys Ala Ser Pro
130                 135                 140

Pro Glu Val Ser Thr Cys Val Asp Asp Gly Cys Leu His Asp Ala Cys
145                 150                 155                 160

Trp Pro Ala Ile Asn Phe Ala Val Glu Leu Thr Tyr Ala Ser Ser Val
                165                 170                 175

Phe Gln Val Pro Glu Leu Val Ser Leu Phe Gln Arg Arg Leu Leu Asn
            180                 185                 190

Phe Val Asp Lys Ala Leu Val Glu Asp Val Ile Pro Ile Leu Val Val
        195                 200                 205

Ala Phe His Cys Gln Leu Gln Asn Val Leu Ser Arg Cys Ile Asp Arg
210                 215                 220

Val Val Arg Ser Lys Leu Asp Thr Ile Ser Ile Glu Lys Glu Leu Pro
225                 230                 235                 240

Phe Glu Val Thr Gln Met Ile Lys Ser Ile Asp Asn Ile Ile Gln Glu
                245                 250                 255

Asp Asp Glu His Thr Val Glu Ser Val Val Leu Arg Glu Lys Arg
            260                 265                 270

Ile Lys Ser Ile His Lys Ala Leu Asp Cys Asp Asp Val Glu Leu Val
        275                 280                 285

Lys Met Ile Leu Asp Glu Ser Lys Ile Thr Leu Asp Glu Ala Cys Ala
290                 295                 300

Leu His Tyr Ala Val Met Tyr Cys Asn Gln Glu Val Ala Lys Glu Ile
305                 310                 315                 320

Leu Asn Leu Asn Arg Ala Asp Val Asn Leu Arg Asn Ser Arg Asp Tyr
                325                 330                 335

Thr Val Leu His Val Ala Ala Met Arg Lys Glu Pro Ser Leu Ile Val
            340                 345                 350

Ser Ile Leu Ser Lys Gly Ala Cys Ala Ser Asp Thr Thr Phe Asp Gly
        355                 360                 365

Gln Ser Ala Val Ser Ile Cys Arg Arg Arg Thr Arg Pro Lys Asp Tyr
370                 375                 380

Tyr Val Lys Thr Glu His Gly Gln Glu Thr Asn Lys Asp Arg Ile Cys
385                 390                 395                 400

Ile Asp Val Leu Glu Arg Glu Ile Lys Arg Asn Pro Met Ile Gly Asp
                405                 410                 415

Val Ser Val Cys Ser Ser Ala Val Ala Asp Asp Leu His Met Asn Leu
            420                 425                 430

Leu Tyr Leu Glu Asn Arg Val Ala Phe Ala Arg Leu Leu Phe Pro Ser
        435                 440                 445

Glu Ala Lys Leu Ala Met Glu Ile Ala His Ala Gln Thr Thr Ala Gln
    450                 455                 460

Tyr Pro Gly Leu Leu Ala Ser Lys Gly Ser Asn Gly Asn Leu Arg Glu
465                 470                 475                 480
```

```
Met Asp Leu Asn Glu Thr Pro Leu Val Gln Asn Lys Arg Leu Leu Ser
            485                 490                 495
Arg Met Glu Ala Leu Ser Arg Thr Val Glu Met Gly Arg Tyr Phe
        500                 505                 510
Pro His Cys Ser Glu Val Leu Asp Lys Phe Met Glu Asp Leu Gln
        515                 520                 525
Asp Leu Phe Ile Leu Glu Lys Gly Thr Glu Glu Gln Glu Ile Lys
        530                 535                 540
Arg Thr Arg Phe Met Glu Leu Lys Glu Asp Val Gln Arg Ala Phe Thr
545                 550                 555                 560
Lys Asp Lys Ala Glu Leu His Arg Gly Leu Ser Ser Ser Met Tyr Thr
                565                 570                 575
Pro Thr Val Arg Asn Gly Ser Lys Ser Lys Ala Arg Lys Tyr Ser
        580                 585                 590

<210> SEQ ID NO 14
<211> LENGTH: 590
<212> TYPE: PRT
<213> ORGANISM: Glycine max
<220> FEATURE:
<223> OTHER INFORMATION: soybean NPR1-2 (GmNPR1-2) protein

<400> SEQUENCE: 14

Met Ala Tyr Ser Ala Glu Pro Ser Ser Ser Leu Ser Phe Thr Ser Ser
1               5                   10                  15
Ser His Leu Ser Asn Gly Ser Val Ser His Asn Ile Cys Ser Ser Tyr
                20                  25                  30
Gly Ser Asp Pro Gly Pro Asn Leu Glu Ala Leu Ser Leu Ser Lys Leu
            35                  40                  45
Ser Ser Asn Phe Glu Gln Leu Leu Ile Glu Thr Asp Cys Asp Tyr Ser
        50                  55                  60
Asp Ala Asp Ile Val Val Glu Gly Ile Ser Val Ser Val His Arg Cys
65                  70                  75                  80
Ile Leu Ala Ser Arg Ser Lys Phe Phe His Glu Leu Phe Lys Arg Glu
                85                  90                  95
Lys Gly Ser Ser Glu Lys Glu Gly Lys Leu Lys Tyr Asn Met Ser Asp
            100                 105                 110
Leu Leu Pro Tyr Gly Lys Val Gly Tyr Glu Ala Phe Leu Ile Phe Leu
        115                 120                 125
Gly Tyr Val Tyr Thr Gly Lys Leu Lys Pro Ser Pro Met Glu Val Ser
130                 135                 140
Thr Cys Val Asp Ser Val Cys Ala His Asp Ala Cys Arg Pro Ala Ile
145                 150                 155                 160
Asn Phe Ala Val Glu Leu Met Tyr Ala Ser Tyr Ile Phe Gln Ile Pro
                165                 170                 175
Glu Phe Val Ser Leu Phe Gln Arg Arg Leu Leu Asn Phe Ile Gly Lys
            180                 185                 190
Ala Leu Val Glu Asp Val Ile Pro Ile Leu Thr Val Ala Phe His Cys
        195                 200                 205
Gln Leu Ser Gln Leu Val Asn Gln Cys Ile Asp Arg Val Ala Arg Ser
    210                 215                 220
Asp Leu Asp Gln Ile Ser Ile Asp Gln Glu Leu Pro Asn Glu Leu Ser
225                 230                 235                 240
Gln Lys Val Lys Leu Leu Arg Arg Asn Pro Gln Arg Asp Val Glu Asn
                245                 250                 255
```

Asp Ala Ser Ile Val Asp Ala Leu Ser Leu Lys Arg Ile Thr Arg Ile
            260                 265                 270

His Lys Ala Leu Asp Ser Asp Val Glu Leu Val Lys Leu Leu Leu
    275                 280                 285

Asn Glu Ser Asp Ile Thr Leu Asp Glu Ala Asn Ala Leu His Tyr Ala
290                 295                 300

Ala Ala Tyr Cys Asp Pro Lys Val Val Ser Glu Val Leu Gly Leu Gly
305                 310                 315                 320

Leu Ala Asn Val Asn Leu Arg Asn Ser Arg Gly Tyr Thr Val Leu His
                325                 330                 335

Ile Ala Ala Met Arg Lys Glu Pro Ser Ile Ile Val Ser Leu Leu Thr
            340                 345                 350

Lys Gly Ala Cys Ala Ser Asp Leu Thr Phe Asp Gly Gln Ser Ala Val
            355                 360                 365

Ser Ile Cys Arg Arg Leu Thr Arg Pro Lys Asp Tyr His Ala Lys Thr
370                 375                 380

Glu Gln Gly Lys Glu Thr Asn Lys Asp Arg Ile Cys Ile Asp Val Leu
385                 390                 395                 400

Glu Arg Glu Met Trp Arg Asn Pro Leu Ala Gly Asp Ala Cys Met Ser
                405                 410                 415

Ser His Thr Met Ala Asp Asp Leu His Met Lys Leu Leu Tyr Leu Glu
            420                 425                 430

Asn Arg Val Ala Phe Ala Arg Leu Phe Phe Pro Ser Glu Ala Lys Leu
            435                 440                 445

Ala Met Asp Ile Ala His Ala Glu Thr Thr Ser Glu Phe Ala Gly Leu
450                 455                 460

Ser Ala Ser Asn Ser Lys Gly Ser Asn Gly Asn Leu Arg Glu Val Asp
465                 470                 475                 480

Leu Asn Glu Thr Pro Ile Val Gln Ser Lys Arg Leu Phe Ser Arg Met
                485                 490                 495

Glu Ala Leu Met Lys Thr Val Glu Met Gly Arg Arg Tyr Phe Pro His
            500                 505                 510

Cys Ser Glu Val Leu Asp Lys Phe Met Glu Asp Asp Leu Pro Asp Leu
            515                 520                 525

Phe Tyr Leu Glu Lys Gly Thr Asn Glu Glu Gln Arg Ile Lys Arg Thr
530                 535                 540

Arg Phe Met Glu Leu Lys Asp Asp Val His Lys Ala Phe Asn Met Asp
545                 550                 555                 560

Lys Ala Glu Phe Ser Arg Ser Gly Ile Ser Ser Ser Ser Ser Ser Ser
                565                 570                 575

Ser Leu Arg Asp Ser Val Val His Tyr Lys Ala Arg Lys Val
            580                 585                 590

<210> SEQ ID NO 15
<211> LENGTH: 679
<212> TYPE: PRT
<213> ORGANISM: Populus trichocarpa
<220> FEATURE:
<223> OTHER INFORMATION: black cottonwood (Western balsam polar) ankyrin
      repeat BTB/POZ domain-containing protein, NPR41
      (PtrNPR41)

<400> SEQUENCE: 15

Met Ala Asn Phe Ser Glu Pro Ser Ser Ser Leu Ser Tyr Thr Ser Ser
1               5                   10                  15

Ser His Leu Ser Asn Gly Ser Ile Ser His Asn Ile Ser Asn Ser Ser

```
            20                  25                  30
Gly Ala Glu Ala Gly Thr Ser Leu Glu Val Ile Ser Leu Asn Lys Leu
         35                  40                  45

Ser Ser Asn Leu Glu Gln Leu Leu Ile Asp Ser Thr Cys Asp Tyr Ser
 50                  55                  60

Asp Ala Asp Ile Val Val Glu Gly Thr Ala Ile Gly Val His Arg Cys
 65                  70                  75                  80

Ile Leu Gly Ala Arg Ser Lys Phe Phe His Glu Leu Phe Arg Arg Glu
             85                  90                  95

Lys Gly Ser Ser Glu Lys Glu Gly Lys Pro Lys Tyr Cys Met Ser Asp
            100                 105                 110

Leu Leu Pro Cys Gly Lys Val Gly Tyr Glu Ala Phe Leu Ile Phe Leu
        115                 120                 125

Ser Tyr Leu Tyr Thr Gly Lys Leu Lys Pro Ser Pro Met Glu Val Ser
        130                 135                 140

Thr Cys Val Asp Asn Val Cys Ala His Asp Ala Cys Arg Pro Ala Ile
145                 150                 155                 160

Asn Phe Ala Val Glu Leu Met Tyr Ala Ser Ser Ile Phe Gln Val Pro
            165                 170                 175

Glu Leu Val Ser Leu Phe Gln Leu Val Asn Leu Glu Asn Trp Asp Pro
            180                 185                 190

Thr Cys Phe Thr Ser Phe Ala His Gly Ala Asn Ile Ser Asn Asp Ser
        195                 200                 205

Phe Leu Ala Val Gln Arg Arg Leu Gln Asn Phe Val Gly Lys Ala Leu
        210                 215                 220

Val Glu Asp Met Ile Pro Ile Leu Val Val Ala Phe His Cys Gln Leu
225                 230                 235                 240

Ser Gln Leu Val Thr Gln Cys Val Asp Arg Ile Ala Arg Ser Asp Leu
            245                 250                 255

Asp Asn Ile Ser Ile Glu Lys Glu Leu Pro His Asp Val Ala Val Glu
        260                 265                 270

Ile Lys Leu Leu Arg Arg Lys Ser Ile Ser Asp Glu Glu Asn Asn Thr
        275                 280                 285

Glu Ala Val Asp Ala Leu Arg Glu Lys Arg Ile Lys Arg Ile His Met
        290                 295                 300

Ala Leu Asp Ser Asp Asp Val Glu Leu Val Lys Leu Leu Leu Thr Glu
305                 310                 315                 320

Ser Asp Ile Thr Leu Asp Asp Ala Asn Ala Leu His Tyr Ala Ala Ser
            325                 330                 335

Tyr Cys Asp Leu Lys Val Val Ser Glu Val Leu Ser Leu Gly Leu Ala
            340                 345                 350

Asp Val Asn Leu Arg Asn Ser Arg Gly Tyr Thr Val Leu His Ile Ala
        355                 360                 365

Ala Met Arg Lys Glu Pro Ser Val Ile Val Ser Met Leu Ala Lys Gly
        370                 375                 380

Ala Ser Ala Leu Asp Leu Thr Ser Asp Gly Gln Ser Ala Val Ser Ile
385                 390                 395                 400

Cys Arg Arg Leu Thr Arg Pro Lys Asp Tyr His Ala Lys Thr Glu Gln
            405                 410                 415

Gly Gln Glu Ala Asn Lys Asp Arg Leu Cys Ile Asp Ile Leu Glu Arg
        420                 425                 430

Glu Met Arg Arg Asn Pro Met Ala Gly Ser Ala Ser Ile Thr Ser His
        435                 440                 445
```

```
Thr Met Val Asp Asp Leu His Met Lys Leu Leu Tyr Leu Glu Asn Arg
    450                 455                 460

Ala Phe Ala Arg Leu Phe Phe Pro Thr Glu Ala Lys Leu Ala Met Asp
465                 470                 475                 480

Ile Ala His Ala Ala Thr Thr Pro Glu Phe Ala Gly Leu Ala Ala Ser
                485                 490                 495

Lys Gly Ser Asn Gly Asn Leu Arg Glu Val Asp Leu Asn Glu Thr Pro
                500                 505                 510

Ile Met Gln Asn Lys Arg Leu Arg Ser Arg Met Glu Ala Leu Met Lys
            515                 520                 525

Thr Glu Met Gly Arg Arg Tyr Phe Pro Ser Cys Ser Glu Val Leu Asp
    530                 535                 540

Lys Phe Met Glu Asp Asp Leu Pro Asp Leu Phe Tyr Leu Glu Lys Gly
545                 550                 555                 560

Thr Pro Asp Glu Gln Arg Ile Lys Arg Thr Arg Phe Met Glu Leu Lys
                565                 570                 575

Glu Asp Val His Arg Ala Phe Thr Lys Asp Lys Ala Glu Ile Asn Arg
                580                 585                 590

Thr Gly Leu Ser Ser Ser Ser Ser Ser Ser Leu Lys Asp Ser Lys
    595                 600                 605

Phe Ser Ser Ser Gly Ser Cys Phe His Asn Met Ser Asp Leu Phe Cys
610                 615                 620

Trp Asn Leu Glu Tyr Lys Leu Arg His Gly Phe Leu Val Tyr Arg His
625                 630                 635                 640

Val Ile Gly Leu Pro Val Pro Leu Val Lys Ala Val Lys Ile Pro Lys
                645                 650                 655

Pro Trp His Phe Asp Lys Arg Lys Gly Ser Thr Glu Arg Leu Phe Arg
                660                 665                 670

Thr Gln Tyr Ile Pro Leu Lys
        675

<210> SEQ ID NO 16
<211> LENGTH: 628
<212> TYPE: PRT
<213> ORGANISM: Vitis vinifera
<220> FEATURE:
<223> OTHER INFORMATION: wine grape cultivar Pinot Noir hypothetical
      protein VITISV_004499, clone ENTAV 115
<221> NAME/KEY: VARIANT
<222> LOCATION: (263)...(281)
<223> OTHER INFORMATION: Xaa = any amino acid

<400> SEQUENCE: 16

Met Ala Asn Ser Ala Glu Pro Ser Ser Ser Leu Ser Phe Thr Ser Ser
 1               5                  10                  15

Ser His Ile Ser Asn Ala Val Thr Ser His Asn Met Ser Ser Ser Ser
            20                  25                  30

Gly Ser Glu Thr Gly Pro Ser Leu Glu Ile Ile Ser Leu Ser Lys Leu
        35                  40                  45

Ser Ser Asn Leu Glu Gln Leu Leu Val Asp Ser Gly Cys Asp Tyr Ser
    50                  55                  60

Asp Ala Glu Ile Ile Val Glu Gly Ile Pro Val Gly Val His Arg Cys
65                  70                  75                  80

Ile Leu Ala Ala Arg Ser Arg Phe Phe Tyr Asp Leu Phe Lys Arg Glu
                85                  90                  95

Lys Ser Ser Ser Glu Lys Asp Gly Lys Pro Arg Tyr Cys Met Ser Asp
```

```
            100                 105                 110
Phe Leu Pro Tyr Gly Lys Val Gly Tyr Glu Ala Phe Leu Ile Phe Leu
            115                 120                 125

Ser Tyr Leu Tyr Thr Gly Lys Leu Lys Ala Ser Pro Leu Glu Val Ser
            130                 135                 140

Thr Cys Val Asp Thr Gly Cys Ala His Asp Ala Cys Arg Pro Ala Ile
145                 150                 155                 160

Asp Phe Ser Val Glu Leu Met Tyr Ala Ser Ala Ile Phe Gln Val Pro
            165                 170                 175

Glu Leu Val Ser Leu Phe Gln Val Thr Leu Trp Glu Val Leu Arg Ser
            180                 185                 190

Gly Asp Leu Gln Pro Ile Asp Gly Met Gly Lys Gly Lys Val Arg Val
            195                 200                 205

Glu Trp Met Leu Leu Cys Lys Arg Cys Val Cys Arg Leu Asp Glu Val
            210                 215                 220

Asp Lys Asn Ser Tyr Leu Thr Phe His Ala Leu Leu Glu Asp Val Ile
225                 230                 235                 240

Pro Ile Leu Val Val Ala Tyr His Cys Lys Ser Ser Val Leu Val Asn
                245                 250                 255

Gln Cys Val Asx Arg Val Xaa Arg Ser Asx Leu Asp Ser Ile Ser Leu
            260                 265                 270

Glu Lys Asp Leu Pro Tyr Glu Val Xaa Glu Ser Ile Lys Leu Leu Arg
            275                 280                 285

Leu Lys Ser Gln Pro Asp Asp Glu Cys Asn Thr Val Pro Val Asp Pro
            290                 295                 300

Val His Glu Lys Arg Val Arg Arg Ile Leu Lys Ala Leu Asp Ser Asp
305                 310                 315                 320

Asp Val Glu Leu Val Lys Leu Leu Leu Ser Glu Ser Gly Ile Thr Leu
                325                 330                 335

Asp Glu Ala Tyr Ala Leu His Tyr Ala Ala Ala Tyr Cys Asp Pro Lys
            340                 345                 350

Val Val Ser Glu Val Leu Ser Leu Gly Leu Ala Asp Val Asn Arg His
            355                 360                 365

Asn Pro Arg Gly Tyr Thr Val Leu His Val Ala Ala Met Arg Lys Glu
            370                 375                 380

Pro Ser Ile Ile Val Ser Leu Leu Thr Lys Gly Ala His Ala Ser Glu
385                 390                 395                 400

Arg Thr Ser Asp Gly Gln Ser Ala Val Ser Ile Cys Arg Arg Leu Thr
                405                 410                 415

Arg Pro Lys Asp Tyr His Ala Lys Met Glu Gln Gly Gln Glu Thr Asn
            420                 425                 430

Lys Asp Arg Ile Cys Ile Asp Val Leu Glu Arg Glu Met Arg Arg Asn
                435                 440                 445

Pro Leu Ala Gly Asp Val Ser Ile Ser Ser Pro Thr Met Ala Asp Asp
            450                 455                 460

Leu His Met Lys Leu Leu Tyr Leu Glu Asn Arg Val Ala Phe Ala Arg
465                 470                 475                 480

Leu Phe Phe Pro Ser Glu Ala Lys Leu Ala Met Glu Ile Ala His Ala
                485                 490                 495

Glu Thr Thr Ser Glu Phe Ala Gly Leu Ser Ala Ser Lys Arg Ser Ser
            500                 505                 510

Gly Asn Leu Arg Glu Val Asp Leu Asn Glu Thr Pro Ile Met Gln Asn
            515                 520                 525
```

```
Gln Arg Leu Arg Ser Arg Met Asn Ala Leu Val Lys Thr Val Glu Met
            530                 535                 540

Gly Arg Arg Tyr Phe Pro His Cys Ser Gln Val Leu Asp Lys Phe Met
545                 550                 555                 560

Glu Asp Asp Leu Pro Asp Leu Phe Tyr Leu Glu Lys Gly Thr Leu Asp
                565                 570                 575

Glu Gln Arg Ile Lys Arg Thr Arg Phe Met Glu Leu Lys Glu Asp Val
            580                 585                 590

Gln Arg Ala Phe Thr Lys Asp Lys Ala Glu Phe Asn Arg Ser Gly Leu
        595                 600                 605

Ser Ser Ser Ser Ser Ser Ser Leu Lys Asp Asn Leu Ser His Lys
    610                 615                 620

Ala Arg Lys Leu
625

<210> SEQ ID NO 17
<211> LENGTH: 588
<212> TYPE: PRT
<213> ORGANISM: Nicotiniana glutinosa
<220> FEATURE:
<223> OTHER INFORMATION: tobacco nonexpressor of pathogenesis-related
      genes 3 (NPR3)

<400> SEQUENCE: 17

Met Ala Cys Ser Ala Glu Pro Ser Ser Ile Ser Phe Thr Ser Ser
  1               5                  10                  15

Ser Ile Thr Ser Asn Gly Ser Ile Gly Val Gly Gln Asn Thr His Ala
             20                  25                  30

Tyr Gly Gly Ser Glu Thr Gly Thr Ser Tyr Glu Ile Ile Ser Leu Ser
         35                  40                  45

Lys Leu Ser Asn Ser Leu Glu Gln Leu Leu Ser Asp Ser Ile Thr Asp
     50                  55                  60

Phe Ser Asp Ala Glu Ile Val Val Glu Gly Val Ser Leu Gly Val His
 65                  70                  75                  80

Arg Cys Ile Leu Ala Ala Arg Ser Lys Phe Phe Gln Asp Leu Phe Arg
                 85                  90                  95

Lys Glu Lys Gly Ser Cys Gly Lys Glu Gly Lys Pro Arg Tyr Ser Met
            100                 105                 110

Thr Asp Ile Leu Pro Tyr Gly Lys Val Gly Tyr Glu Ala Phe Leu Thr
        115                 120                 125

Phe Leu Ser Tyr Leu Tyr Ser Gly Lys Leu Lys His Phe Pro Pro Glu
    130                 135                 140

Val Ser Thr Cys Thr Asp Thr Ile Cys Ala His Asp Ser Cys Arg Pro
145                 150                 155                 160

Ala Ile Ser Phe Ser Val Glu Leu Met Tyr Ala Ser Ser Val Phe Gln
                165                 170                 175

Val Pro Glu Leu Val Ser Leu Phe Leu Arg Arg Leu Ile Asn Phe Val
            180                 185                 190

Gly Lys Ala Leu Val Glu Asp Val Ile Pro Ile Leu Arg Val Ala Phe
        195                 200                 205

His Cys Gln Leu Ser Glu Leu Leu Thr His Cys Val Asp Arg Val Ala
    210                 215                 220

Arg Ser Asp Leu Glu Ile Ile Cys Ile Glu Lys Glu Val Pro Phe Glu
225                 230                 235                 240

Val Ala Glu Ser Ile Lys Ser Leu Arg Pro Lys Cys Gln Val Asp Glu
```

```
                        245                 250                 255
Ser Lys Val Leu Pro Val Asp Pro Leu His Glu Lys Arg Lys Asn Arg
            260                 265                 270

Ile Tyr Lys Ala Leu Asp Ser Asp Val Glu Leu Val Lys Leu Leu
            275                 280                 285

Leu Asp Glu Ser Glu Ile Ser Leu Asp Glu Ala Tyr Ala Leu His Tyr
            290                 295                 300

Ala Val Ala Tyr Cys Asp Pro Lys Val Val Thr Asp Val Leu Gly Leu
305                 310                 315                 320

Asp Val Ala Asp Val Asn Leu Arg Asn Thr Arg Gly Tyr Thr Val Leu
                325                 330                 335

His Ile Ala Ala Met Arg Lys Glu Pro Thr Ile Ile Val Ser Leu Leu
            340                 345                 350

Thr Lys Gly Ala His Val Ser Glu Ile Thr Leu Asp Gly Gln Ser Ala
            355                 360                 365

Val Ser Ile Cys Arg Arg Leu Thr Arg Pro Lys Glu Tyr His Ala Lys
370                 375                 380

Thr Glu Gln Gly Gln Glu Ala Asn Lys Asp Arg Val Cys Ile Asp Val
385                 390                 395                 400

Leu Glu Arg Glu Met His His Asn Pro Met Ala Gly Asp Ala Leu Phe
                405                 410                 415

Ser Ser Gln Met Leu Ala Asp Asp Leu His Met Lys Leu His Tyr Leu
            420                 425                 430

Glu Asn Arg Val Ala Phe Ala Arg Leu Leu Phe Pro Leu Glu Ala Arg
            435                 440                 445

Leu Ala Met Gln Ile Ala Asn Ala Glu Thr Ala Ala Glu Phe Ala Gly
450                 455                 460

Arg Leu Ala Ser Lys Ser Ser Gly Asn Leu Arg Glu Val Asp Leu
465                 470                 475                 480

Asn Glu Thr Pro Ile Lys Gln Lys Glu Arg Leu Leu Ser Arg Met Gln
                485                 490                 495

Ala Leu Ser Lys Thr Val Glu Phe Gly Lys Arg Tyr Phe Pro His Cys
            500                 505                 510

Ser Gln Val Leu Asp Lys Phe Met Glu Asp Leu Pro Asp Leu Ile
            515                 520                 525

Phe Leu Glu Met Gly Thr Pro Glu Glu Gln Lys Ile Lys Arg Lys Arg
            530                 535                 540

Phe Lys Glu Leu Lys Asp Asp Val Gln Arg Ala Phe Asn Lys Asp Lys
545                 550                 555                 560

Ala Glu Leu His Ser Ser Gly Leu Ser Ser Ser Cys Ser Ser Ser
                565                 570                 575

Phe Lys Asp Gly Ala Ser Val Lys His Arg Lys Leu
            580                 585

<210> SEQ ID NO 18
<211> LENGTH: 586
<212> TYPE: PRT
<213> ORGANISM: Malus x domestica
<220> FEATURE:
<223> OTHER INFORMATION: apple cultivar Jonathan NPR1-like protein
      (MpNPR1), contains BTB/BOZ domain and ankyrin
      repeat domain

<400> SEQUENCE: 18

Met Ala His Ser Ala Glu Pro Ser Ser Ser Leu Ser Phe Thr Ser Ser
1               5                   10                  15
```

```
Pro His Leu Ser Asn Gly Ser Ile Ser His Asn Leu Ser Cys Ser Gly
         20                  25                  30

Ser Glu Ser Val Pro Ser Leu Glu Val Ile Ser Leu Ser Lys Leu Ser
         35                  40                  45

Ser Ser Leu Glu Gln Leu Leu Ile Asp Pro Gly Cys Asp Tyr Ser Asp
     50                  55                  60

Ala Asp Ile Val Val Glu Gly Ile Pro Val Gly Val His Arg Cys Ile
65                   70                  75                  80

Leu Ala Ser Arg Ser Gly Phe Phe Arg Glu Leu Phe Lys Arg Glu Lys
                 85                  90                  95

Gly Ser Ser Gly Lys Glu Asp Arg Pro Lys Tyr Cys Met Ser Asp Phe
             100                 105                 110

Leu Pro Tyr Gly Asp Val Gly Tyr Glu Ala Phe Leu Val Phe Leu Ser
         115                 120                 125

Tyr Val Tyr Thr Gly Lys Leu Lys Pro Ser Pro Val Glu Val Ser Thr
    130                 135                 140

Cys Val His Asn Val Cys Ala His Asp Ala Cys Arg Pro Ala Ile Asn
145                 150                 155                 160

Phe Val Val Glu Leu Met Tyr Ala Ala Ser Ile Phe Gln Met Pro Asp
                165                 170                 175

Leu Val Ser Ile Phe Glu Arg Arg Leu Leu Asn Phe Val Gly Lys Ala
            180                 185                 190

Leu Ser Asp Asn Val Val Pro Ile Leu Leu Val Ala Phe His Cys Gln
        195                 200                 205

Leu Asn Gln Leu Ile Asp Gln Cys Val Asp Arg Val Ala Arg Ser Asp
    210                 215                 220

Ile Asp Asp Ile Ser Leu Glu Lys Gly Leu Pro Asp Glu Val Val Lys
225                 230                 235                 240

Lys Ile Lys Ile Leu Arg Arg Asn Tyr Gln Gln Asp Ser Asp Pro Asn
            245                 250                 255

Leu Pro Pro Ala Asp Pro Leu His Glu Lys Arg Ile Arg Arg Ile His
        260                 265                 270

Lys Ala Leu Asp Ser Asp Val Glu Leu Val Lys Leu Leu Thr
    275                 280                 285

Glu Ser Asn Ile Thr Leu Asp Glu Ala Asn Ala Leu His Tyr Ala Ala
290                 295                 300

Ala Tyr Cys Asp Pro Lys Val Val Thr Glu Val Leu Ala Leu Gly Leu
305                 310                 315                 320

Ala Asp Val Asn Leu Arg Asn Ser Arg Gly Tyr Thr Val Leu His Ile
            325                 330                 335

Ala Val Met Arg Lys Glu Pro Ser Ile Ile Val Leu Leu Leu Thr Lys
        340                 345                 350

Gly Ala Arg Ala Ser Glu Leu Thr Ser Asp Gly Gln Ser Ala Val Ser
    355                 360                 365

Ile Cys Arg Arg Leu Thr Arg Pro Lys Asp Tyr His Ser Lys Thr Glu
370                 375                 380

Gln Gly Gln Glu Ala Asn Lys Asp Arg Ile Cys Ile Asp Val Leu Glu
385                 390                 395                 400

Arg Glu Met Arg Arg Asn Pro Met Ala Gly Asp Ala Ser Ile Ser Ser
            405                 410                 415

Gln Ile Met Pro Asp Asp Leu His Met Glu Leu Leu Asn Leu Glu Asn
        420                 425                 430
```

```
Arg Val Ala Leu Ala Arg Leu Phe Pro Ala Glu Ala Lys Leu Ala
            435                 440                 445

Met Val Ile Ala His Ala Glu Thr Ser Glu Phe Ala Ala Pro Ser Ser
450                 455                 460

Ser Lys Gly Ser Ser Gly Asn Leu Met Glu Val Asp Leu Asn Glu Thr
465                 470                 475                 480

Pro Thr Val Gln Asn Lys Arg Leu His Ser Arg Leu Glu Ala Leu Met
                485                 490                 495

Lys Thr Val Arg Leu Gly Arg Cys Tyr Phe Pro His Cys Ser Glu Val
                500                 505                 510

Leu Asp Lys Phe Ile Asp Asp Leu Pro His Leu Phe Tyr Leu Glu
            515                 520                 525

Pro Gly Ser Ser Asp Glu Gln Lys Val Lys Arg Arg Arg Phe Met Glu
        530                 535                 540

Leu Lys Glu Glu Val Gln Lys Ala Phe Asp Lys Asp Lys Ala Glu Cys
545                 550                 555                 560

Asn Leu Ser Gly Leu Ser Ser Ser Ser Thr Thr Ser Pro Glu Lys
                565                 570                 575

Ile Gly Ala Asn Gln Lys Val Arg Glu Pro
            580                 585

<210> SEQ ID NO 19
<211> LENGTH: 586
<212> TYPE: PRT
<213> ORGANISM: Pyrus x bretschneideri
<220> FEATURE:
<223> OTHER INFORMATION: Chinese white pear (bai li) cultivar Zaosu NPR-
      1

<400> SEQUENCE: 19

Met Ala His Ser Ala Glu Pro Ser Ser Ser Leu Ser Phe Thr Ser Ser
1               5                   10                  15

Pro His Leu Ser Asn Gly Ser Ile Ser His Asn Leu Ser Cys Ser Gly
                20                  25                  30

Ser Glu Ser Val Pro Ser Leu Glu Val Ile Ser Leu Ser Lys Leu Ser
            35                  40                  45

Ser Ser Leu Glu Gln Leu Leu Ile Asp Pro Gly Cys Asp Tyr Ser Asp
    50                  55                  60

Ala Asp Ile Val Val Glu Gly Ile Pro Val Gly Val His Arg Cys Ile
65                  70                  75                  80

Leu Ala Ser Arg Ser Gly Phe Phe Arg Glu Leu Phe Lys Arg Asp Lys
                85                  90                  95

Gly Ser Ser Gly Lys Glu Asp Arg Pro Lys Tyr Cys Met Ser Asp Phe
                100                 105                 110

Leu Pro Tyr Gly Asp Val Gly Tyr Glu Ala Phe Leu Val Phe Leu Ser
            115                 120                 125

Tyr Val Tyr Thr Gly Lys Leu Lys Pro Ser Pro Val Glu Val Ser Thr
    130                 135                 140

Cys Val His Asn Val Cys Ala His Asp Ala Cys Arg Pro Ala Ile Asn
145                 150                 155                 160

Phe Val Val Glu Leu Met Tyr Ala Ala Ser Ile Phe Gln Met Pro Asp
                165                 170                 175

Leu Val Ser Ile Phe Glu Arg Arg Leu Leu Asn Phe Val Gly Lys Ala
            180                 185                 190

Leu Ser Asp Asn Val Ile Pro Ile Leu Val Val Ala Phe His Cys Gln
    195                 200                 205
```

Leu Asn Gln Leu Ile Asp Gln Cys Ile Asp Arg Val Ala Arg Ser Asp
            210                 215                 220

Ile Asp Asp Ile Ser Leu Glu Lys Gly Leu Pro Asp Glu Val Val Lys
225                 230                 235                 240

Lys Ile Lys Ile Leu Arg Arg Asn Tyr Gln Gln Asp Ser Asp Pro Asn
                245                 250                 255

Leu Pro Pro Ala Asp Pro Leu Leu Glu Lys Arg Ile Arg Ile His
            260                 265                 270

Lys Ala Leu Asp Ser Asp Asp Val Glu Leu Val Lys Leu Leu Leu Thr
275                 280                 285

Glu Ser Asn Ile Thr Leu Asp Glu Ala Asn Ala Leu His Tyr Ala Ala
            290                 295                 300

Ala Tyr Cys Asp Pro Lys Val Val Thr Glu Val Leu Ala Leu Gly Leu
305                 310                 315                 320

Ala Asp Val Asn Leu Arg Asn Ala Arg Gly Tyr Thr Val Leu His Ile
                325                 330                 335

Ala Val Met Arg Lys Glu Pro Ser Ile Ile Val Leu Leu Leu Thr Lys
            340                 345                 350

Gly Ala Arg Ala Ser Glu Leu Thr Ser Asp Gly Gln Ser Ala Val Ser
355                 360                 365

Ile Cys Arg Arg Leu Thr Arg Pro Lys Asp Tyr His Ser Lys Thr Glu
            370                 375                 380

Gln Gly Gln Glu Ala Asn Lys Asp Arg Ile Cys Ile Asp Val Leu Glu
385                 390                 395                 400

Arg Glu Met Arg Arg Asn Pro Met Ala Gly Asp Ala Ser Ile Ser Ser
                405                 410                 415

Gln Ile Met Pro Asp Asp Leu His Met Glu Leu Leu Asn Leu Glu Asn
            420                 425                 430

Arg Val Ala Leu Ala Arg Leu Phe Phe Pro Ala Glu Ala Lys Leu Ala
            435                 440                 445

Met Val Ile Ala His Ala Glu Thr Ser Glu Phe Ala Ala Pro Ser Ser
450                 455                 460

Ser Lys Gly Ser Ser Gly Asn Leu Met Glu Val Asp Leu Asn Glu Thr
465                 470                 475                 480

Pro Thr Val Gln Asn Lys Arg Leu His Ser Arg Leu Glu Ala Leu Met
                485                 490                 495

Lys Thr Val Arg Leu Gly Arg Cys Tyr Phe Pro His Cys Ser Glu Val
            500                 505                 510

Leu Asp Lys Phe Ile Ala Asp Leu Pro Asp Leu Phe Tyr Leu Glu
            515                 520                 525

Pro Gly Ser Ser Asp Glu Gln Lys Val Lys Arg Arg Phe Met Glu
530                 535                 540

Leu Lys Glu Glu Val Gln Lys Ala Phe Asp Lys Asp Lys Ala Glu Cys
545                 550                 555                 560

Asn Leu Ser Gly Leu Ser Ser Ser Ser Thr Ser Pro Glu Lys
                565                 570                 575

Ile Gly Ala Asn Gln Lys Val Arg Glu Pro
            580                 585

<210> SEQ ID NO 20
<211> LENGTH: 27
<212> TYPE: DNA
<213> ORGANISM: Artificial Sequence
<220> FEATURE:

<223> OTHER INFORMATION: synthetic NH3 PCR amplification primer NH3TAP1

<400> SEQUENCE: 20
caccgagacg tccaccataa gcttctc         27

<210> SEQ ID NO 21
<211> LENGTH: 24
<212> TYPE: DNA
<213> ORGANISM: Artificial Sequence
<220> FEATURE:
<223> OTHER INFORMATION: synthetic NH3 PCR amplification primer NH3TAP3

<400> SEQUENCE: 21
actgcagatt agacttaact gctg         24

<210> SEQ ID NO 22
<211> LENGTH: 34
<212> TYPE: DNA
<213> ORGANISM: Artificial Sequence
<220> FEATURE:
<223> OTHER INFORMATION: synthetic NH3 promoter PCR amplification primer
      NH3P-1

<400> SEQUENCE: 22
ttttaagctt cgttggatga actacattgc tgat         34

<210> SEQ ID NO 23
<211> LENGTH: 36
<212> TYPE: DNA
<213> ORGANISM: Artificial Sequence
<220> FEATURE:
<223> OTHER INFORMATION: synthetic NH3 promoter PCR amplification primer
      NH3P-2

<400> SEQUENCE: 23
ttggatccag atcttatccg gaaatttcgc gcgtgt         36

<210> SEQ ID NO 24
<211> LENGTH: 29
<212> TYPE: DNA
<213> ORGANISM: Artificial Sequence
<220> FEATURE:
<223> OTHER INFORMATION: synthetic NH3 promoter fragment PCR
      amplification primer NH3P-3

<400> SEQUENCE: 24
cacctcgttg gatgaactac attgctgat         29

<210> SEQ ID NO 25
<211> LENGTH: 33
<212> TYPE: DNA
<213> ORGANISM: Artificial Sequence
<220> FEATURE:
<223> OTHER INFORMATION: synthetic NH3 promoter fragment PCR
      amplification primer NH3P-NcoI

<400> SEQUENCE: 25
tccatggctc ttatccggaa atttcgcgcg tgt         33

<210> SEQ ID NO 26
<211> LENGTH: 24
<212> TYPE: DNA
<213> ORGANISM: Artificial Sequence
<220> FEATURE:
<223> OTHER INFORMATION: synthetic NH3 cDNA PCR re-amplification primer
      NH3ATG -continued

```
<400> SEQUENCE: 26
caccatggag acgtccacca taag                                          24

<210> SEQ ID NO 27
<211> LENGTH: 40
<212> TYPE: DNA
<213> ORGANISM: Artificial Sequence
<220> FEATURE:
<223> OTHER INFORMATION: synthetic NH3 cDNA PCR re-amplification primer
      NH3-cMyc

<400> SEQUENCE: 27
ggagatgagc ttctgctccc gtgatagctt cccttcttg                          40

<210> SEQ ID NO 28
<211> LENGTH: 47
<212> TYPE: DNA
<213> ORGANISM: Artificial Sequence
<220> FEATURE:
<223> OTHER INFORMATION: synthetic NH3 cDNA PCR re-amplification primer
      cMyc-SpeI

<400> SEQUENCE: 28
actagttatt tctccaacag gtcttcctcg gagatgagct tctgctc                 47

<210> SEQ ID NO 29
<211> LENGTH: 21
<212> TYPE: DNA
<213> ORGANISM: Artificial Sequence
<220> FEATURE:
<223> OTHER INFORMATION: synthetic NH3 RT-PCR primer NH3-RT1

<400> SEQUENCE: 29
gtgcattggc gtcttacagc a                                             21

<210> SEQ ID NO 30
<211> LENGTH: 21
<212> TYPE: DNA
<213> ORGANISM: Artificial Sequence
<220> FEATURE:
<223> OTHER INFORMATION: synthetic NH3 RT-PCR primer NH3-RT2

<400> SEQUENCE: 30
gggaagtatc gtcgtccgag t                                             21

<210> SEQ ID NO 31
<211> LENGTH: 20
<212> TYPE: DNA
<213> ORGANISM: Artificial Sequence
<220> FEATURE:
<223> OTHER INFORMATION: synthetic NTAP-NH3 RT-PCR primer NH3-2

<400> SEQUENCE: 31
gtggctgcag ccgtcgtcca                                               20

<210> SEQ ID NO 32
<211> LENGTH: 24
<212> TYPE: DNA
<213> ORGANISM: Artificial Sequence
<220> FEATURE:
<223> OTHER INFORMATION: synthetic NTAP-NH3 RT-PCR primer NTAP-5

<400> SEQUENCE: 32
atgcccaagc cccaaaggac tacg                                          24
```

<210> SEQ ID NO 33
<211> LENGTH: 21
<212> TYPE: DNA
<213> ORGANISM: Artificial Sequence
<220> FEATURE:
<223> OTHER INFORMATION: synthetic NH1 RT-PCR primer NH1-RT1

<400> SEQUENCE: 33
acttagctcg gatgacggca c                                        21

<210> SEQ ID NO 34
<211> LENGTH: 24
<212> TYPE: DNA
<213> ORGANISM: Artificial Sequence
<220> FEATURE:
<223> OTHER INFORMATION: synthetic NH1 RT-PCR primer NH1-TAP2

<400> SEQUENCE: 34
agcaatggtg ttcatctcct tggt                                     24

<210> SEQ ID NO 35
<211> LENGTH: 22
<212> TYPE: DNA
<213> ORGANISM: Artificial Sequence
<220> FEATURE:
<223> OTHER INFORMATION: synthetic actin reference gene quantitative
      real time QPCR primer Actin-Q1

<400> SEQUENCE: 35
tcggctctga atgtacctcc ta                                       22

<210> SEQ ID NO 36
<211> LENGTH: 24
<212> TYPE: DNA
<213> ORGANISM: Artificial Sequence
<220> FEATURE:
<223> OTHER INFORMATION: synthetic actin reference gene quantitative
      real time QPCR primer Actin-Q2

<400> SEQUENCE: 36
cacttgagta aagactgtca cttg                                     24

<210> SEQ ID NO 37
<211> LENGTH: 19
<212> TYPE: DNA
<213> ORGANISM: Artificial Sequence
<220> FEATURE:
<223> OTHER INFORMATION: synthetic NH1 gene quantitative real time QPCR
      primer NH1-RT3

<400> SEQUENCE: 37
ctgatccgtt tccctcgga                                           19

<210> SEQ ID NO 38
<211> LENGTH: 21
<212> TYPE: DNA
<213> ORGANISM: Artificial Sequence
<220> FEATURE:
<223> OTHER INFORMATION: synthetic NH1 gene quantitative real time QPCR
      primer NH1-RT4

<400> SEQUENCE: 38
gacctgtcat tctcctcctt g                                        21

<210> SEQ ID NO 39
<211> LENGTH: 21
<212> TYPE: DNA

<213> ORGANISM: Artificial Sequence
<220> FEATURE:
<223> OTHER INFORMATION: synthetic NH3 gene quantitative real time QPCR
      primer NH3-RT3

<400> SEQUENCE: 39
tgctacacct ctgctggttg a                                             21

<210> SEQ ID NO 40
<211> LENGTH: 23
<212> TYPE: DNA
<213> ORGANISM: Artificial Sequence
<220> FEATURE:
<223> OTHER INFORMATION: synthetic NH3 gene quantitative real time QPCR
      primer NH3-RT4

<400> SEQUENCE: 40
gaccagcaaa ctcttgagtt gag                                           23

<210> SEQ ID NO 41
<211> LENGTH: 20
<212> TYPE: DNA
<213> ORGANISM: Artificial Sequence
<220> FEATURE:
<223> OTHER INFORMATION: synthetic PR3 gene quantitative real time QPCR
      primer PR3-1

<400> SEQUENCE: 41
cttggactgc tacaaccaga                                               20

<210> SEQ ID NO 42
<211> LENGTH: 20
<212> TYPE: DNA
<213> ORGANISM: Artificial Sequence
<220> FEATURE:
<223> OTHER INFORMATION: synthetic PR3 gene quantitative real time QPCR
      primer PR3-2

<400> SEQUENCE: 42
cattgtgggc attactgatg                                               20

<210> SEQ ID NO 43
<211> LENGTH: 24
<212> TYPE: DNA
<213> ORGANISM: Artificial Sequence
<220> FEATURE:
<223> OTHER INFORMATION: synthetic POX8.1 gene quantitative real time
      QPCR primer POX8.1-1

<400> SEQUENCE: 43
caaactggat acaaaagcaa acac                                          24

<210> SEQ ID NO 44
<211> LENGTH: 18
<212> TYPE: DNA
<213> ORGANISM: Artificial Sequence
<220> FEATURE:
<223> OTHER INFORMATION: synthetic POX8.1 gene quantitative real time
      QPCR primer
      POX8.1-2

<400> SEQUENCE: 44
catgggcttc ctgatctg                                                 18

<210> SEQ ID NO 45
<211> LENGTH: 19
<212> TYPE: DNA

```
<213> ORGANISM: Artificial Sequence
<220> FEATURE:
<223> OTHER INFORMATION: synthetic POX22.3 gene quantitative real time
      QPCR primer
      POX22.3-1

<400> SEQUENCE: 45
atcgtgtcga cgacgacat                                                    19

<210> SEQ ID NO 46
<211> LENGTH: 21
<212> TYPE: DNA
<213> ORGANISM: Artificial Sequence
<220> FEATURE:
<223> OTHER INFORMATION: synthetic POX22.3 gene quantitative real time
      QPCR primer
      POX22.3-2

<400> SEQUENCE: 46
ctctgctcca tacacttgat g                                                 21
```